US006875785B2

(12) United States Patent
Talley et al.

(10) Patent No.: US 6,875,785 B2
(45) Date of Patent: Apr. 5, 2005

(54) HETEROCYCLO SUBSTITUTED HYDROXAMIC ACID DERIVATIVES AS CYCLOOXYGENASE-2 AND 5-LIPOXYGENASE INHIBITORS

(75) Inventors: John J. Talley, Cambridge, MA (US); James A. Sikorski, Atlanta, GA (US); Matthew J. Graneto, Chesterfield, MO (US); Jeffery S. Carter, Chesterfield, MO (US); Bryan H. Norman, Indianapolis, IN (US); Balekudru Devadas, Chesterfield, MO (US); Hwang-Fun Lu, Ballwin, MO (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

(21) Appl. No.: 10/254,701

(22) Filed: Sep. 25, 2002

(65) Prior Publication Data

US 2003/0119886 A1 Jun. 26, 2003

Related U.S. Application Data

(63) Continuation of application No. 09/878,452, filed on Jun. 11, 2001, now Pat. No. 6,512,121, which is a continuation of application No. 08/945,840, filed as application No. PCT/US96/08314 on May 31, 1996, now abandoned, which is a continuation of application No. 08/458,545, filed on Jun. 2, 1995, now abandoned.

(51) Int. Cl.$^7$ .................... A61K 31/421; C07D 413/00; A61P 29/00
(52) U.S. Cl. ........................ 514/374; 548/236; 548/215
(58) Field of Search .............................. 548/236, 215; 514/374

(56) References Cited

U.S. PATENT DOCUMENTS

| | | | |
|---|---|---|---|
| 3,647,858 A | 3/1972 | Hinkley et al. | |
| 3,707,475 A | 12/1972 | Lombardino | |
| 3,743,656 A | 7/1973 | Brown et al. | |
| 3,901,908 A | 8/1975 | Fitzi et al. | |
| 3,984,431 A | 10/1976 | Gueremy et al. | |
| 4,011,328 A | 3/1977 | Pinhas et al. | |
| 4,051,250 A | 9/1977 | Dahm et al. | |
| 4,146,721 A | 3/1979 | Rainer | |
| 4,302,461 A | 11/1981 | Cherkofsky | |
| 4,372,964 A | 2/1983 | Whitney | |
| 4,381,311 A | 4/1983 | Haber | |
| 4,427,693 A | 1/1984 | Haber | |
| 4,472,422 A | 9/1984 | Whitney | |
| 4,503,065 A | 3/1985 | Wilkerson | |
| 4,533,666 A | 8/1985 | Matsumoto et al. | |
| 4,576,958 A | 3/1986 | Wexler | |
| 4,590,205 A | 5/1986 | Haber | |
| 4,632,930 A | 12/1986 | Carini et al. | |
| 4,686,231 A | 8/1987 | Bender et al. | |
| 4,820,827 A | 4/1989 | Haber | |
| 4,822,805 A | 4/1989 | Takasugi et al. | |
| 4,914,121 A | 4/1990 | Sawai et al. | |
| 5,051,518 A | 9/1991 | Murray et al. | |
| 5,098,932 A | 3/1992 | Hamon | |
| 5,134,142 A | 7/1992 | Matsuo et al. | |
| 5,169,875 A | 12/1992 | Nakamura et al. | |
| 5,234,939 A | 8/1993 | Capiris et al. | |
| 5,234,950 A | 8/1993 | Edwards et al. | |
| 5,242,940 A | 9/1993 | Wachter et al. | |
| 5,298,521 A | 3/1994 | Ferro | |
| 5,302,603 A | 4/1994 | Crawley et al. | |
| 5,344,991 A | 9/1994 | Reitz et al. | |
| 5,354,865 A | 10/1994 | Dellaria et al. | |
| 5,356,898 A | 10/1994 | Belliotti et al. | |
| 5,364,877 A | 11/1994 | Bruneau et al. | |
| 5,380,738 A | * 1/1995 | Norman et al. | ............. 514/304 |
| 5,393,790 A | 2/1995 | Reitz et al. | |
| 5,633,272 A | 5/1997 | Talley et al. | |
| 5,668,161 A | 9/1997 | Talley et al. | |
| 5,686,470 A | 11/1997 | Weier et al. | |
| 5,698,584 A | 12/1997 | Black et al. | |
| 5,916,905 A | 6/1999 | Weier et al. | |
| 5,985,902 A | 11/1999 | Talley et al. | |
| 6,512,121 B2 | * 1/2003 | Talley et al. | ................. 548/111 |

FOREIGN PATENT DOCUMENTS

| | | |
|---|---|---|
| EP | 26928 A1 | 4/1981 |
| EP | 372445 B1 | 6/1990 |
| EP | 592664 B1 | 4/1994 |
| WO | WO 92/05162 A1 | 4/1992 |
| WO | WO 92/19604 A1 | 11/1992 |
| WO | WO 93/14082 A1 | 7/1993 |

(Continued)

OTHER PUBLICATIONS

McKearn et al., 2000, CAS:133:84241.*
Stewart et al., "N, O–Bis(phenoxycarbonyl)hydroxylamine: A New Reagent for the Direct Synthesis of Substituted N–Hydroxyureas." J. Org. Chem., 1992, pp. 5020–5023, vol. 57, No. 18.
Gierse et al., "Expression and selective inhibition of the constitutive and inducible forms of human cyclo–oxygenase." Biochemical Journal, 1995, pp. 479–484, vol. 305, No. 2.
Grimmett, "Advances in Imidazole Chemistry," in Advances in Heterocyclic Chemistry, 1970, pp. 104–183, vol. 12, Academic Press, New York and London.
Miyaura et al., "The Palladium–Catalyzed Cross–Coupling Reaction of Phenylboronic Acid With Haloarenes in the Presence of Bases," Synth. Commun., 1981, pp. 513–519, vol. 11, No. 7.
Winter et al., "Carrageenin–Induced Edema in Hing Paw of the Rat as an Assay for Antiinflammatory Drugs," Proc. Soc. Exp. Biol. Med., 1962, pp. 544–546, vol. 111, No. 3.

*Primary Examiner*—Rita Desai
*Assistant Examiner*—Robert Shiao
(74) *Attorney, Agent, or Firm*—Senniger Powers

(57) ABSTRACT

This invention is in the field of antiinflammatory pharmaceutical agents and specifically relates to compounds, compositions and methods for treating disorders mediated by cyclooxygenase-2 or 5-lipoxygenase, such as inflammation.

5 Claims, No Drawings

FOREIGN PATENT DOCUMENTS

| | | |
|---|---|---|
| WO | WO 94/13635 A1 | 6/1994 |
| WO | WO 94/15932 A1 | 7/1994 |
| WO | WO 94/20480 A1 | 9/1994 |
| WO | WO 94/26731 A1 | 11/1994 |
| WO | WO 94/27980 A1 | 12/1994 |
| WO | WO 95/00501 A2 | 1/1995 |
| WO | WO 96/03388 A1 | 2/1996 |
| WO | WO 96/24584 A1 | 8/1996 |
| WO | WO 96/36617 A1 | 11/1996 |
| WO | WO 96/38418 A1 | 12/1996 |
| WO | WO 96/38442 A1 | 12/1996 |
| WO | WO 97/16435 A1 | 5/1997 |
| WO | WO 97/25047 A1 | 7/1997 |
| WO | WO 97/27181 A1 | 7/1997 |
| WO | WO 97/29775 A1 | 8/1997 |
| WO | WO 97/29776 A1 | 8/1997 |
| WO | WO 98/03484 A1 | 1/1998 |
| WO | WO 98/16227 A1 | 4/1998 |
| WO | WO 98/22101 A2 | 5/1998 |

\* cited by examiner

HETEROCYCLO SUBSTITUTED HYDROXAMIC ACID DERIVATIVES AS CYCLOOXYGENASE-2 AND 5-LIPOXYGENASE INHIBITORS

REFERENCE TO RELATED APPLICATIONS

This application is a continuation of Ser. No. 09/878,452, filed Jun. 11, 2001, now U.S. Pat. No. 6,512,121 which is a continuation of Ser. No. 08/945,840, filed Sep. 14, 1998, now abandoned, which is a 371 of PCT/US96/08314, filed May 31, 1996, which is a continuation of Ser. No. 08/458,545, filed Jun. 2, 1995, now abandoned.

FIELD OF THE INVENTION

This invention is in the field of antiinflammatory pharmaceutical agents and specifically relates to compounds, compositions and methods for treating disorders mediated by cyclooxygenase-2 or 5-lipoxygenase, such as inflammation and allergic conditions such as asthma.

BACKGROUND OF THE INVENTION

Prostaglandins play a major role in the inflammation process, and the inhibition of prostaglandin production, especially production of $PGG_2$, $PGH_2$ and $PGE_2$, has been a common target of antiinflammatory drug discovery. However, common non-steroidal antiinflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandins by inhibiting enzymes in the human arachidonic acid/prostaglandin pathway including the enzyme cyclooxygenase (COX). The recent discovery of an inducible enzyme associated with inflammation (named "cyclooxygenase-2 (COX-2)" or "prostaglandin G/H synthase II") provides a viable target of inhibition which more effectively reduces inflammation and produces fewer and less drastic side effects.

In another portion of the arachidonic acid pathway, physiologically active leukotrienes, such as leukotriene $B_4$ ($LTB_4$), leukotriene $C_4$ ($LTC_4$) and leukotriene $D_4$ ($LTD_4$) and other metabolites, are produced by the 5-lipoxygenase-mediated (5-LO) oxidation of arachidonic acid. These leukotrienes have been implicated in various inflammation-related disorders and allergic diseases, and thus compounds which inhibit 5-lipoxygenase are useful in the treatment of disease states in which leukotrienes play an important role.

It is believed that selective dual inhibitors of both cyclooxygenase-2 and 5-lipoxygenase, which affect the two enzymes at low concentrations, will more completely and permanently affect the damage caused by the various diseases and disorders mediated by cyclooxygenase-2 and 5-lipoxygenase but without the gastrointestinal side effects associated with traditional NSAIDs.

The references below that disclose antiinflammatory activity, show continuing efforts to find a safe and effective antiinflammatory agent. The novel compounds disclosed herein are such safe and also effective antiinflammatory agents furthering such efforts. The compounds disclosed herein preferably selectively inhibit cyclooxygenase-2 over cyclooxygenase-1.

Compounds which selectively inhibit cyclooxygenase-2 have been described in U.S. Pat. Nos. 5,380,738, 5,344,991, 5,393,790 and WO documents WO94/15932, WO94/27980, WO95/00501, WO94/13635, WO94/20480, and WO94/26731.

Compounds which inhibit 5-lipoxygenase have been described in U.S. Pat. Nos. 5,364,877, 5,302,603, 5,234,950, 5,098,932 and 5,354,865, among others.

Compounds which inhibit both cyclooxygenase and 5-lipoxygenase have been described in U.S. Pat. Nos. 5,051,518, 5,298,521, 5,242,940, 5,234,939, and 5,356,898, among others. However, these previous mixed inhibitors do not selectively inhibit cyclooxygenase-2 and therefore still cause the gastrointestinal side effects which substantially reduce their usage and effectiveness.

The invention's compounds are found to show usefulness as dual inhibitors of cyclooxygenase-2 and 5-lipoxygenase with minimal side effects.

DESCRIPTION OF THE INVENTION

A class of compounds useful in treating cyclooxygenase-2 and 5-lipoxygenase-mediated disorders is defined by Formula I:

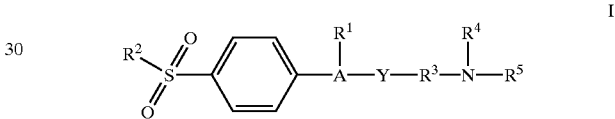

wherein A is a 5- or 6-member ring substituent selected from partially unsaturated or unsaturated heterocyclo and carbocyclic rings, wherein A is optionally substituted with a radical selected from acyl, halo, alkyl, haloalkyl, cyano, nitro, carboxyl, alkoxy, oxo, aminocarbonyl, alkoxycarbonyl, carboxyalkyl, cyanoalkyl, and hydroxyalkyl;

wherein Y is one or more radicals selected from alkyl, alkynyl, alkenyl, hydroxyalkyl, aminoalkyl, alkylaminoalkyl, arylaminoalkyl, acyl, aryl, aralkyl, cycloalkyl, cycloalkylalkyl, heterocyclo and heterocycloalkyl;

wherein $R^1$ is one or more substituents selected from heterocyclo, cycloalkyl, cycloalkenyl and aryl, wherein $R^1$ is optionally substituted at a substitutable position with one or more radicals selected from alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy and alkylthio;

wherein $R^2$ is selected from alkyl and amino;

wherein $R^3$ is a direct bond or a radical selected from

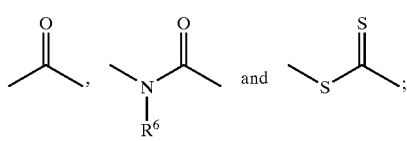

wherein $R^4$ is selected from hydrido, hydroxyl, alkyl, aryl, heterocyclo and cycloalkyl;

wherein $R^5$ is selected from hydrido, alkyl, aryl, heterocyclo and cycloalkyl; and wherein R⁶ is selected from hydrido and hydroxyl; provided R² is amino when A is pyrazolyl;

or a pharmaceutically-acceptable salt thereof.

Compounds of Formula I would be useful for, but not limited to, the treatment of inflammation in a subject, and for treatment of other inflammation-associated disorders, such as, as an analgesic in the treatment of pain and headaches, or as an antipyretic for the treatment of fever. For example, compounds of the invention would be useful to treat arthritis, including but not limited to rheumatoid arthritis, spondyloarthopathies, gouty arthritis, osteoarthritis, systemic lupus erythematosus and juvenile arthritis. Such compounds of the invention would be useful in the treatment of asthma, bronchitis, menstrual cramps, tendinitis, bursitis, skin-related conditions such as psoriasis, eczema, burns and dermatitis, and from post-operative inflammation including from ophthalmic surgery such as cataract surgery and refractive surgery. Compounds of the invention also would be useful to treat gastrointestinal conditions such as inflammatory bowel disease, Crohn's disease, gastritis, irritable bowel syndrome and ulcerative-colitis, and for the prevention or treatment of cancer, such as colorectal cancer. Compounds of the invention would be useful in treating inflammation in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like. The compounds would also be useful in the treatment of ophthalmic diseases, such as retinitis, retinopathies, uveitis, ocular photophobia, and of acute injury to the eye tissue. The compounds would also be useful in the treatment of pulmonary inflammation, such as that associated with viral infections and cystic fibrosis. The compounds would also be useful for the treatment of certain central nervous system disorders such as cortical dementias including Alzheimer's disease. The compounds of the invention are useful as anti-inflammatory agents, such as for the treatment of arthritis, with the additional benefit of having significantly less harmful side effects. These compounds would also be useful in the treatment of allergic rhinitis, respiratory distress syndrome, endotoxin shock syndrome, atherosclerosis and central nervous system damage resulting from stroke, ischemia and trauma. The compounds would also be useful in the treatment of pain, but not limited to postoperative pain, dental pain, muscular pain, and pain resulting from cancer.

Besides being useful for human treatment, these compounds are also useful for treatment of mammals, including horses, dogs, cats, rats, mice, sheep, pigs, etc.

The present compounds may also be used in co-therapies, partially or completely, in place of other conventional antiinflammatories, such as together with steroids, NSAIDs, LTB₄ antagonists and LTA₄ hydrolase inhibitors.

Suitable LTB₄ inhibitors include, among others, ebselen, Bayer Bay-x-1005, Ciba Geigy compound CGS-25019C, Leo Denmark compound ETH-615, Lilly compound LY-293111, Ono compound ONO-4057, Terumo compound TMK-688, Lilly compounds LY-213024, 264086 and 292728, Ono compound ONO-LB457, Searle compound SC-53228, calcitrol, Lilly compounds LY-210073, LY223982, LY233469, and LY255283, ONO compound ONO-LB-448, Searle compounds SC-41930, SC-50605 and SC-51146, and SK&F compound SKF-104493. Preferably, the LTB₄ inhibitors are selected from ebselen, Bayer Bay-x-1005, Ciba Geigy compound CGS-25019C, Leo Denmark compound ETH-615, Lilly compound LY-293111, Ono compound ONO-4057, and Terumo compound TMK-688.

Suitable 5-LO inhibitors include, among others, masoprocol, tenidap, zileuton, pranlukast, tepoxalin, rilopirox, flezelastine hydrochloride, enazadrem phosphate, and bunaprolast.

The present invention preferably includes compounds which selectively inhibit cyclooxygenase-2 over cyclooxygenase-1 as well as inhibit the 5-lipoxygenase enzyme. Preferably, the compounds have a cyclooxygenase-2 $IC_{50}$ of less than about 10 $\mu$M, and also have a selectivity ratio of cyclooxygenase-2 inhibition over cyclooxygenase-1 inhibition of at least 10, and more preferably of at least 100, and inhibit 5-lipoxygenase at less than about 10 $\mu$M. Even more preferably, the compounds have a cyclooxygenase-1 $IC_{50}$ of greater than about 10 $\mu$M, and more preferably of greater than 20 $\mu$M and have a 5-lipoxygenase $IC_{50}$ of less than about 1 $\mu$M. Such preferred selectivity may indicate an ability to reduce the incidence of common NSAID-induced side effects.

A preferred class of compounds consists of those compounds of Formula I wherein A is selected from thienyl, oxazolyl, furyl, pyrrolyl, thiazolyl, imidazolyl, isothiazolyl, isoxazolyl, pyrazolyl, cyclopentenyl, phenyl, and pyridyl, wherein A is optionally substituted with a radical selected from acyl, halo, lower alkyl, lower haloalkyl, oxo, cyano, nitro, carboxyl, lower alkoxy, aminocarbonyl, lower alkoxycarbonyl, lower carboxyalkyl, lower cyanoalkyl, and lower hydroxyalkyl; wherein Y is a radical selected from lower alkyl, lower alkynyl, lower alkenyl, lower hydroxyalkyl, lower aminoalkyl, lower alkylaminoalkyl, lower arylaminoalkyl, lower acyl, aryl, lower aralkyl, lower cycloalkyl, lower cycloalkylalkyl, 5- or 6-membered heterocyclo and lower heterocycloalkyl; wherein R¹ is one or more substituents selected from 5- and 6-membered heterocyclo, lower cycloalkyl, lower cycloalkenyl and aryl selected from phenyl, biphenyl and naphthyl, where R¹ is optionally substituted at a substitutable position with one or more radicals selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, halo, lower alkoxy and lower alkylthio; wherein R² is selected from lower alkyl and amino; wherein R³ is a direct bond or a radical selected from

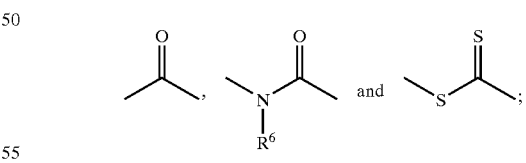

wherein R⁴ is selected from hydrido, hydroxyl, lower alkyl, phenyl, 5- and 6-membered heterocyclo and lower cycloalkyl; wherein R⁵ is selected from hydrido, lower alkyl, phenyl, 5- and 6-membered heterocyclo and lower cycloalkyl; and wherein R⁶ is selected from hydrido and hydroxyl; or a pharmaceutically-acceptable salt thereof.

A class of compounds of particular interest consists of those compounds of Formula I wherein A is a radical selected from thienyl, oxazolyl, furyl, pyrrolyl, thiazolyl, imidazolyl, isoxazolyl, pyrazolyl, cyclopentenyl, phenyl, and pyridyl, wherein A is optionally substituted with a radical selected from formyl, fluoro, chloro, bromo, methyl, trifluoromethyl, oxo, cyano, carboxyl, methoxy, aminocarbonyl, methoxycarbonyl, ethoxycarbonyl, acetyl, carboxypropyl, and hydroxymethyl; wherein Y is a radical selected from ethyl, propyl, isopropyl, butyl, 1-propynyl, 2-propynyl, 1-butyn-3-yl, 1-propenyl, 2-propenyl, acetyl, dihydroxypropyl, hydroxyethyl, 1-amino-ethyl, 1-aminopropyl, 1-(N-methylamino)propyl, 1-(N,N-dimethylamino) propyl, 1-(N-phenylamino)propyl, triazolyl, thienyl, benzyl, phenylethyl, cyclohexylmethyl, cyclopentylethyl, triazolylmethyl, thienylmethyl and phenyl optionally substituted at a substitutable position with one or more radicals selected from fluoro, chloro, bromo, hydroxyl, methyl, and methoxy; wherein $R^1$ is a substituent selected from thienyl, oxazolyl, furyl, pyrrolyl, thiazolyl, imidazolyl, isoxazolyl, pyrazolyl, pyridyl, and phenyl, where $R^1$ is optionally substituted at a substitutable position with one or more radicals selected from methyl, trifluoromethyl, hydroxyl, hydroxymethyl, trifluoromethoxy, nitro, methoxymethyl, fluoro, chloro, bromo, methoxy and methylthio; wherein $R^2$ is methyl or amino; wherein $R^3$ is a direct bond or a radical selected from

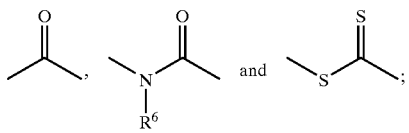

wherein $R^4$ is selected from hydrido, hydroxyl, methyl, and phenyl; wherein $R^5$ is selected from hydrido, methyl, and phenyl; and wherein $R^6$ is selected from hydrido and hydroxyl; or a pharmaceutically-acceptable salt thereof.

Within Formula I there is a subclass of compounds of high interest represented by Formula II:

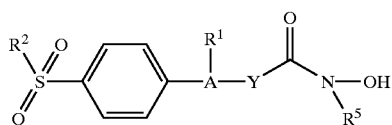

wherein A is a ring substituent selected from thienyl, oxazolyl, furyl, pyrrolyl, thiazolyl, imidazolyl, isothiazolyl, isoxazolyl, pyrazolyl, cyclopentenyl, phenyl, and pyridyl; wherein A is optionally substituted with a radical selected from acyl, halo, hydroxyl, lower alkyl, lower haloalkyl, oxo, cyano, nitro, carboxyl, lower alkoxy, aminocarbonyl, lower alkoxycarbonyl, lower carboxyalkyl, lower cyanoalkyl, and lower hydroxyalkyl; wherein Y is selected from lower alkyl, lower alkenyl and lower alkynyl; wherein $R^1$ is selected from 5- and 6-membered heterocyclo, lower cycloalkyl, lower cycloalkenyl and aryl selected from phenyl, biphenyl and naphthyl, wherein $R^1$ is optionally substituted at a substitutable position with one or more radicals selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, halo, lower alkoxy and lower alkylthio; wherein $R^2$ is selected from lower alkyl and amino; and wherein $R^5$ is selected from hydrido, lower alkyl, phenyl, 5- and 6-membered heterocyclo and lower cycloalkyl; provided $R^2$ is amino when A is pyrazolyl; or a pharmaceutically-acceptable salt thereof.

A class of compounds of particular interest consists of those compounds of Formula II wherein A is selected from thienyl, oxazolyl, furyl, pyrrolyl, thiazolyl, imidazolyl, isoxazolyl, pyrazolyl, cyclopentenyl, phenyl, and pyridyl, wherein A is optionally substituted with a radical selected from formyl, fluoro, chloro, bromo, methyl, trifluoromethyl, oxo, cyano, carboxyl, methoxy, aminocarbonyl, methoxycarbonyl, ethoxycarbonyl, acetyl, carboxypropyl, and hydroxymethyl; wherein Y is a radical selected from methyl, ethyl, isopropyl, propyl, butyl, propenyl, butenyl, propynyl and butynyl; wherein $R^1$ is selected from thienyl, oxazolyl, furyl, pyrrolyl, thiazolyl, imidazolyl, isoxazolyl, pyrazolyl, pyridyl, and phenyl, where $R^1$ is optionally substituted at a substitutable position with one or more radicals selected from methyl, trifluoromethyl, hydroxyl, hydroxymethyl, trifluoromethoxy, methoxymethyl, fluoro, chloro, bromo, methoxy and methylthio; wherein $R^2$ is methyl or amino; and wherein $R^5$ is selected from hydrido, methyl, and phenyl; or a pharmaceutically-acceptable salt thereof.

Within Formula I there is a second subclass of compounds of high interest represented by Formula III:

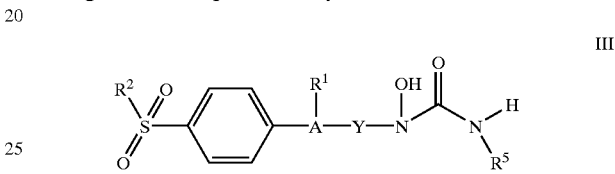

wherein A is a ring substituent selected from thienyl, oxazolyl, furyl, pyrrolyl, thiazolyl, imidazolyl, isothiazolyl, isoxazolyl, pyrazolyl, cyclopentenyl, phenyl, and pyridyl; wherein A is optionally substituted with a radical selected from acyl, halo, hydroxyl, lower alkyl, lower haloalkyl, oxo, cyano, nitro, carboxyl, lower alkoxy, aminocarbonyl, lower alkoxycarbonyl, lower carboxyalkyl, lower cyanoalkyl, and lower hydroxyalkyl; wherein Y is selected from lower alkyl, lower alkenyl and lower alkynyl; wherein $R^1$ is selected from 5- and 6-membered heterocyclo, lower cycloalkyl, lower cycloalkenyl and aryl selected from phenyl, biphenyl and naphthyl, wherein $R^1$ is optionally substituted at a substitutable position with one or more radicals selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, halo, lower alkoxy and lower alkylthio; wherein $R^2$ is selected from lower alkyl and amino; and wherein $R^5$ is selected from hydrido and alkyl; or a pharmaceutically-acceptable salt thereof.

A class of compounds of particular interest consists of those compounds of Formula III wherein A is selected from thienyl, oxazolyl, furyl, pyrrolyl, thiazolyl, imidazolyl, isoxazolyl, pyrazolyl, cyclopentenyl, phenyl, and pyridyl, wherein A is optionally substituted with a radical selected from formyl, fluoro, chloro, bromo, methyl, trifluoromethyl, oxo, cyano, carboxyl, methoxy, aminocarbonyl, methoxycarbonyl, ethoxycarbonyl, acetyl, carboxypropyl, and hydroxymethyl; wherein Y is selected from methyl, ethyl, isopropyl, propyl, butyl, propenyl, butenyl, propynyl and butynyl; wherein $R^1$ is selected from thienyl, oxazolyl, furyl, pyrrolyl, thiazolyl, imidazolyl, isoxazolyl, pyrazolyl, pyridyl, and phenyl, where $R^1$ is optionally substituted at a substitutable position with one or more radicals selected from methyl, trifluoromethyl, hydroxyl, hydroxymethyl, trifluoromethoxy, methoxymethyl, fluoro, chloro, bromo, methoxy and methylthio; wherein $R^2$ is methyl or amino; and wherein $R^5$ is selected from hydrido, and methyl; or a pharmaceutically-acceptable salt thereof.

A class of compounds of particular interest consists of those compounds of Formula I

[4-[(4-aminosulfonyl)phenyl]-5-phenyl-2-oxazolyl]methyl-N-hydroxy-N-methyl-dithiocarbamate;
[4-[(4-aminosulfonyl)phenyl]-5-(4-chlorophenyl)-2-oxazolyl]methyl-N-hydroxy-N-methyl-dithiocarbamate;
[5-[(4-aminosulfonyl)phenyl]-4-phenyl-2-oxazolyl]methyl-N-hydroxy-N-methyl-dithiocarbamate;
[5-[(4-aminosulfonyl)phenyl]-4-(4-chlorophenyl)-2-oxazolyl]methyl-N-hydroxy-N-methyl-dithiocarbamate;
[5-[(4-aminosulfonyl)phenyl]-4-(4-fluorophenyl)-2-oxazolyl]methyl-N-hydroxy-N-methyl-dithiocarbamate;
[5-[(4-aminosulfonyl)phenyl]-4-(4-methoxyphenyl)-2-oxazolyl]methyl-N-hydroxy-N-methyl-dithiocarbamate;
[5-[(4-aminosulfonyl)phenyl]-4-(3-chloro-4-methoxyphenyl)-2-oxazolyl]methyl-N-hydroxy-N-methyl-dithiocarbamate;
[5-[(4-aminosulfonyl)phenyl]-4-(3-fluoro-4-methoxyphenyl)-2-oxazolyl]methyl-N-hydroxy-N-methyl-dithiocarbamate;
[5-[(4-aminosulfonyl)phenyl]-4-(3-chloro-4-fluorophenyl)-2-oxazolyl]methyl-N-hydroxy-N-methyl-dithiocarbamate;
[4-[(4-methylsulfonyl)phenyl]-5-phenyl-2-oxazolyl]methyl-N-hydroxy-N-methyl-dithiocarbamate;
[5-(4-chlorophenyl)-4-[(4-methylsulfonyl)phenyl]-2-oxazolyl]methyl-N-hydroxy-N-methyl-dithiocarbamate;
[5-[(4-methylsulfonyl)phenyl]-4-phenyl-2-oxazolyl]methyl-N-hydroxy-N-methyl-dithiocarbamate;
[4-(4-chlorophenyl)-5-[(4-methylsulfonyl)phenyl]-2-oxazolyl]methyl-N-hydroxy-N-methyl-dithiocarbamate;
[4-[(4-aminosulfonyl)phenyl]-3-phenyl-5-isoxazolyl]propyl-N-hydroxy-N-methyl-dithiocarbamate;
[4-[(4-aminosulfonyl)phenyl]-3-(4-chlorophenyl)-5-isoxazolyl]propyl-N-hydroxy-N-methyl-dithiocarbamate;
[4-[(4-aminosulfonyl)phenyl]-3-(4-fluorophenyl)-5-isoxazolyl]propyl-N-hydroxy-N-methyl-dithiocarbamate;
[4-[(4-aminosulfonyl)phenyl]-3-(4-methoxyphenyl)-5-isoxazolyl]propyl-N-hydroxy-N-methyl-dithiocarbamate;
[4-[(4-aminosulfonyl)phenyl]-3-(3-chloro-4-methoxyphenyl)-5-isoxazolyl]propyl-N-hydroxy-N-methyl-dithiocarbamate;
[4-[(4-aminosulfonyl)phenyl]-3-(3-fluoro-4-methoxyphenyl)-5-isoxazolyl]propyl-N-hydroxy-N-methyl-dithiocarbamate;
[4-[(4-aminosulfonyl)phenyl]-3-(3-chloro-4-fluorophenyl)-5-isoxazolyl]propyl-N-hydroxy-N-methyl-dithiocarbamate;
[4-[(4-methylsulfonyl)phenyl]-3-phenyl-5-isoxazolyl]propyl-N-hydroxy-N-methyl-dithiocarbamate;
[3-(4-chlorophenyl)-4-[(4-methylsulfonyl)phenyl]-5-isoxazolyl]propyl-N-hydroxy-N-methyl-dithiocarbamate;
[4-[(4-aminosulfonyl)phenyl]-3-phenyl-2-thienyl]propyl-N-hydroxy-N-methyl-dithiocarbamate;
[4-[(4-aminosulfonyl)phenyl]-3-(4-chlorophenyl)-2-thienyl]propyl-N-hydroxy-N-methyl-dithiocarbamate;
[4-[(4-aminosulfonyl)phenyl]-3-(4-fluorophenyl)-2-thienyl]propyl-N-hydroxy-N-methyl-dithiocarbamate;
[4-[(4-aminosulfonyl)phenyl]-3-(4-methoxyphenyl)-2-thienyl]propyl-N-hydroxy-N-methyl-dithiocarbamate;
[4-[(4-aminosulfonyl)phenyl]-3-(3-chloro-4-methoxyphenyl)-2-thienyl]propyl-N-hydroxy-N-methyl-dithiocarbamate;
[4-[(4-aminosulfonyl)phenyl]-3-(3-fluoro-4-methoxyphenyl)-2-thienyl]propyl-N-hydroxy-N-methyl-dithiocarbamate;
[4-[(4-aminosulfonyl)phenyl]-3-(3-chloro-4-fluorophenyl)-2-thienyl]propyl-N-hydroxy-N-methyl-dithiocarbamate;
[3-[(4-methylsulfonyl)phenyl]-4-phenyl-5-thienyl]propyl-N-hydroxy-N-methyl-dithiocarbamate;
[4-(4-chlorophenyl)-3-[(4-methylsulfonyl)phenyl]-5-thienyl]propyl-N-hydroxy-N-methyl-dithiocarbamate;
[5-[(4-aminosulfonyl)phenyl]-6-phenyl-3-pyridyl]propyl-N-hydroxy-N-methyl-dithiocarbamate;
[5-[(4-aminosulfonyl)phenyl]-6-(4-chlorophenyl)-3-pyridyl]propyl-N-hydroxy-N-methyl-dithiocarbamate;
[5-[(4-aminosulfonyl)phenyl]-6-(4-fluorophenyl)-3-pyridyl]propyl-N-hydroxy-N-methyl-dithiocarbamate;
[5-[(4-aminosulfonyl)phenyl]-6-(4-methoxyphenyl)-3-pyridyl]propyl-N-hydroxy-N-methyl-dithiocarbamate;
[6-[(4-aminosulfonyl)phenyl]-5-(3-chloro-4-methoxyphenyl)-3-pyridyl]propyl-N-hydroxy-N-methyl-dithiocarbamate;
[6-[(4-aminosulfonyl)phenyl]-5-(3-fluoro-4-methoxyphenyl)-3-pyridyl]propyl-N-hydroxy-N-methyl-dithiocarbamate;
[5-[(4-aminosulfonyl)phenyl]-6-(3-chloro-4-fluorophenyl)-3-pyridyl]propyl-N-hydroxy-N-methyl-dithiocarbamate;
[5-[(4-methylsulfonyl)phenyl]-6-phenyl-3-pyridyl]propyl-N-hydroxy-N-methyl-dithiocarbamate;
[5-(4-chlorophenyl)-6-[(4-methylsulfonyl)phenyl]-3-pyridyl]propyl-N-hydroxy-N-methyl-dithiocarbamate;
[4-[(4-aminosulfonyl)phenyl]-3-phenyl-2-furyl]propyl-N-hydroxy-N-methyl-dithiocarbamate;
[4-[(4-aminosulfonyl)phenyl]-3-(4-chlorophenyl)-2-furyl]propyl-N-hydroxy-N-methyl-dithiocarbamate;
[4-[(4-aminosulfonyl)phenyl]-3-(4-fluorophenyl)-2-furyl]propyl-N-hydroxy-N-methyl-dithiocarbamate;
[5-[(4-aminosulfonyl)phenyl]-4-(4-methoxyphenyl)-2-furyl]propyl-N-hydroxy-N-methyl-dithiocarbamate;
[4-[(4-aminosulfonyl)phenyl]-5-(3-chloro-4-methoxyphenyl)-2-furyl]propyl-N-hydroxy-N-methyl-dithiocarbamate;
[5-[(4-aminosulfonyl)phenyl]-4-(3-fluoro-4-methoxyphenyl)-2-furyl]propyl-N-hydroxy-N-methyl-dithiocarbamate;
[4-[(4-aminosulfonyl)phenyl]-5-(3-chloro-4-fluorophenyl)-2-furyl]propyl-N-hydroxy-N-methyl-dithiocarbamate;
[4-[(4-methylsulfonyl)phenyl]-3-phenyl-2-furyl]propyl-N-hydroxy-N-methyl-dithiocarbamate;
[4-(4-chlorophenyl)-5-[(4-methylsulfonyl)phenyl]-2-furyl]propyl-N-hydroxy-N-methyl-dithiocarbamate;
[4-[(4-aminosulfonyl)phenyl]-5-phenyl-2-oxazolyl]-1-propyl-N-hydroxy-N-methyl-dithiocarbamate;
[4-[(4-aminosulfonyl)phenyl]-5-(4-chlorophenyl)-2-oxazolyl]-1-propyl-N-hydroxy-N-methyl-dithiocarbamate;
[5-[(4-aminosulfonyl)phenyl]-4-phenyl-2-oxazolyl]-1-propyl-N-hydroxy-N-methyl-dithiocarbamate;
[5-[(4-aminosulfonyl)phenyl]-4-(4-chlorophenyl)-2-oxazolyl]-1-propyl-N-hydroxy-N-methyl-dithiocarbamate;
[5-[(4-aminosulfonyl)phenyl]-4-(4-fluorophenyl)-2-oxazolyl]-1-propyl-N-hydroxy-N-methyl-dithiocarbamate;
[5-[(4-aminosulfonyl)phenyl]-4-(4-methoxyphenyl)-2-oxazolyl]-1-propyl-N-hydroxy-N-methyl-dithiocarbamate;
[5-[(4-aminosulfonyl)phenyl]-4-(3-chloro-4-methoxyphenyl)-2-oxazolyl]-1-propyl-N-hydroxy-N-methyl-dithiocarbamate;
[5-[(4-aminosulfonyl)phenyl]-4-(3-fluoro-4-methoxyphenyl)-2-oxazolyl]-1-propyl-N-hydroxy-N-methyl-dithiocarbamate;
[5-[(4-aminosulfonyl)phenyl]-4-(3-chloro-4-fluorophenyl)-2-oxazolyl]-1-propyl-N-hydroxy-N-methyl-dithiocarbamate;

[4-[(4-methylsulfonyl)phenyl]-4-phenyl-2-oxazolyl]-1-propyl-N-hydroxy-N-methyl-dithiocarbamate;
[5-(4-chlorophenyl)-4-[(4-methylsulfonyl)phenyl]-2-oxazolyl]-1-propyl-N-hydroxy-N-methyl-dithiocarbamate;
[5-[(4-methylsulfonyl)phenyl]-4-phenyl-2-oxazolyl]-1-propyl-N-hydroxy-N-methyl-dithiocarbamate;
[4-(4-chlorophenyl)-5-[(4-methylsulfonyl)phenyl]-2-oxazolyl]-1-propyl-N-hydroxy-N-methyl-dithiocarbamate;
3-[4-[(4-aminosulfonyl)phenyl]-5-phenyl-2-oxazolyl]-2-propenyl-N-hydroxy-N-methyl-dithiocarbamate;
3-[4-[(4-aminosulfonyl)phenyl]-5-(4-chlorophenyl)-2-oxazolyl]-2-propenyl-N-hydroxy-N-methyl-dithiocarbamate;
1-[5-[(4-aminosulfonyl)phenyl]-4-phenyl-2-oxazolyl]-2-propenyl-N-hydroxy-N-methyl-dithiocarbamate;
3-[5-[(4-aminosulfonyl)phenyl]-4-(4-chlorophenyl)-2-oxazolyl]-2-propenyl-N-hydroxy-N-methyl-dithiocarbamate;
3-[5-[(4-aminosulfonyl)phenyl]-4-(4-fluorophenyl)-2-oxazolyl]-2-propenyl-N-hydroxy-N-methyl-dithiocarbamate;
3-[5-[(4-aminosulfonyl)phenyl]-4-(4-methoxyphenyl)-2-oxazolyl]-2-propenyl-N-hydroxy-N-methyl-dithiocarbamate;
3-[5-[(4-aminosulfonyl)phenyl]-4-(3-chloro-4-methoxyphenyl)-2-oxazolyl]-2-propenyl-N-hydroxy-N-methyl-dithiocarbamate;
3-[5-[(4-aminosulfonyl)phenyl]-4-(3-fluoro-4-methoxyphenyl)-2-oxazolyl]-2-propenyl-N-hydroxy-N-methyl-dithiocarbamate;
3-[5-[(4-aminosulfonyl)phenyl]-4-(3-chloro-4-fluorophenyl)-2-oxazolyl]-2-propenyl-N-hydroxy-N-methyl-dithiocarbamate;
3-[4-[(4-methylsulfonyl)phenyl]-5-phenyl-2-oxazolyl]-2-propenyl-N-hydroxy-N-methyl-dithiocarbamate;
3-[5-(4-chlorophenyl)-4-[(4-methylsulfonyl)phenyl]-2-oxazolyl]-2-propenyl-N-hydroxy-N-methyl-dithiocarbamate;
3-[5-[(4-methylsulfonyl)phenyl]-4-phenyl-2-oxazolyl]-2-propenyl-N-hydroxy-N-methyl-dithiocarbamate;
3-[4-(4-chlorophenyl)-5-[(4-methylsulfonyl)phenyl]-2-oxazolyl]-2-propenyl-N-hydroxy-N-methyl-dithiocarbamate;
3-[1-[(4-aminosulfonyl)phenyl]-5-phenyl-1H-pyrazol-3-yl]-2-propenyl-N-hydroxy-N-methyl-dithiocarbamate;
3-[(1-[(4-aminosulfonyl)phenyl]-5-(4-chlorophenyl)-1H-pyrazol-3-yl]-2-propenyl-N-hydroxy-N-methyl-dithiocarbamate;
3-[3-[(4-aminosulfonyl)phenyl]-4-phenyl-1H-pyrazol-1-yl]-2-propenyl-N-hydroxy-N-methyl-dithiocarbamate;
3-[3-[(4-aminosulfonyl)phenyl]-4-(4-chlorophenyl)-1H-pyrazol-1-yl]-2-propenyl-N-hydroxy-N-methyl-dithiocarbamate;
3-[1-[(4-aminosulfonyl)phenyl]-5-(4-fluorophenyl)-1H-pyrazol-3-yl]-2-propenyl-N-hydroxy-N-methyl-dithiocarbamate;
3-[1-[(4-aminosulfonyl)phenyl]-5-(4-methoxyphenyl)-1H-pyrazol-3-yl]-2-propenyl-N-hydroxy-N-methyl-dithiocarbamate;
3-[1-[(4-aminosulfonyl)phenyl]-5-(3-chloro-4-methoxyphenyl)-1H-pyrazol-3-yl]-2-propenyl-N-hydroxy-N-methyl-dithiocarbamate;
3-[1-[(4-aminosulfonyl)phenyl]-5-(3-fluoro-4-methoxyphenyl)-1H-pyrazol-3-yl]-2-propenyl-N-hydroxy-N-methyl-dithiocarbamate;
3-[1-[(4-aminosulfonyl)phenyl]-5-(3-chloro-4-fluorophenyl)-1H-pyrazol-3-yl]-2-propenyl-N-hydroxy-N-methyl-dithiocarbamate;
3-[1-[(4-methylsulfonyl)phenyl]-5-phenyl-1H-pyrazol-3-yl]-2-propenyl-N-hydroxy-N-methyl-dithiocarbamate;
3-[5-(4-chlorophenyl)-1-[(4-methylsulfonyl)phenyl]-1H-pyrazol-3-yl]-2-propenyl-N-hydroxy-N-methyl-dithiocarbamate;
3-[4-[(4-methylsulfonyl)phenyl]-3-phenyl-1H-pyrazol-1-yl]-2-propenyl-N-hydroxy-N-methyl-dithiocarbamate;
3-[4-(4-chlorophenyl)-3-[(4-methylsulfonyl)phenyl]-1H-pyrazol-1-yl]-2-propenyl-N-hydroxy-N-methyl-dithiocarbamate;
3-[4-[(4-aminosulfonyl)phenyl]-5-phenyl-2-oxazolyl]-2-propynyl-N-hydroxy-N-methyl-dithiocarbamate;
3-[4-[(4-aminosulfonyl)phenyl]-5-(4-chlorophenyl)-2-oxazolyl]-2-propynyl-N-hydroxy-N-methyl-dithiocarbamate;
3-[5-[(4-aminosulfonyl)phenyl]-4-phenyl-2-oxazolyl]-2-propynyl-N-hydroxy-N-methyl-dithiocarbamate;
3-[5-[(4-aminosulfonyl)phenyl]-4-(4-chlorophenyl)-2-oxazolyl]-2-propynyl-N-hydroxy-N-methyl-dithiocarbamate;
3-[5-[(4-aminosulfonyl)phenyl]-4-(4-fluorophenyl)-2-oxazolyl]-2-propynyl-N-hydroxy-N-methyl-dithiocarbamate;
3-[5-[(4-aminosulfonyl)phenyl]-4-(4-methoxyphenyl)-2-oxazolyl]-2-propynyl-N-hydroxy-N-methyl-dithiocarbamate;
3-[5-[(4-aminosulfonyl)phenyl]-4-(3-chloro-4-methoxyphenyl)-2-oxazolyl]-2-propynyl-N-hydroxy-N-methyl-dithiocarbamate;
3-[5-[(4-aminosulfonyl)phenyl]-4-(3-fluoro-4-methoxyphenyl)-2-oxazolyl].-2-propynyl-N-hydroxy-N-methyl-dithiocarbamate;
3-[5-[(4-aminosulfonyl)phenyl]-4-(3-chloro-4-fluorophenyl)-2-oxazolyl]-2-propynyl-N-hydroxy-N-methyl-dithiocarbamate;
3-[4-[(4-methylsulfonyl)phenyl]-5-phenyl-2-oxazolyl]-2-propynyl-N-hydroxy-N-methyl-dithiocarbamate;
3-[5-(4-chlorophenyl)-4-[(4-methylsulfonyl)phenyl]-2-oxazolyl]-2-propynyl-N-hydroxy-N-methyl-dithiocarbamate;
3-[5-[(4-methylsulfonyl)phenyl]-4-phenyl-2-oxazolyl]-2-propynyl-N-hydroxy-N-methyl-dithiocarbamate;
3-[4-(4-chlorophenyl)-5-[(4-methylsulfonyl)phenyl]-2-oxazolyl]-2-propynyl-N-hydroxy-N-methyl-dithiocarbamate;
3-[1-[(4-aminosulfonyl)phenyl]-5-phenyl-1H-pyrazol-3-yl]-2-propynyl-N-hydroxy-N-methyl-dithiocarbamate;
3-[1-[(4-aminosulfonyl)phenyl]-5-(4-chlorophenyl)-1H-pyrazol-3-yl]-2-propynyl-N-hydroxy-N-methyl-dithiocarbamate;
3-[3-[(4-aminosulfonyl)phenyl]-4-phenyl-1H-pyrazol-1-yl]-2-propynyl-N-hydroxy-N-methyl-dithiocarbamate;
3-[3-[(4-aminosulfonyl)phenyl]-4-(4-chlorophenyl)-1H-pyrazol-1-yl]-2-propynyl-N-hydroxy-N-methyl-dithiocarbamate;
3-[1-[(4-aminosulfonyl)phenyl]-5-(4-fluorophenyl)-1H-pyrazol-3-yl]-2-propynyl-N-hydroxy-N-methyl-dithiocarbamate;
3-[1-[(4-aminosulfonyl)phenyl]-5-(4-methoxyphenyl)-1H-pyrazol-3-yl]-2-propynyl-N-hydroxy-N-methyl-dithiocarbamate;
3-[1-[(4-aminosulfonyl)phenyl]-5-(3-chloro-4-methoxyphenyl)-1H-pyrazol-3-yl]-2-propynyl-N-hydroxy-N-methyl-dithiocarbamate;

3-[1-[(4-aminosulfonyl)phenyl]-5-(3-fluoro-4-methoxyphenyl)-1H-pyrazol-3-yl]-2-propynyl-N-hydroxy-N-methyl-dithiocarbamate;

3-[1-[(4-aminosulfonyl)phenyl]-5-(3-chloro-4-fluorophenyl)-1H-pyrazol-3-yl]-2-propynyl-N-hydroxy-N-methyl-dithiocarbamate;

3-[1-[(4-methylsulfonyl)phenyl]-5-phenyl-1H-pyrazol-3-yl]-2-propynyl-N-hydroxy-N-methyl-dithiocarbamate;

3-[5-(4-chlorophenyl)-1-[(4-methylsulfonyl)phenyl]-1H-pyrazol-3-yl]-2-propynyl-N-hydroxy-N-methyl-dithiocarbamate;

3-[4-[(4-methylsulfonyl)phenyl]-3-phenyl-1H-pyrazol-1-yl]-2-propynyl-N-hydroxy-N-methyl-dithiocarbamate;

3-[4-(4-chlorophenyl)-3-[(4-methylsulfonyl)phenyl]-1H-pyrazol-1-yl]-2-propynyl-N-hydroxy-N-methyl-dithiocarbamate;

3-[1-[(4-aminosulfonyl)phenyl]-5-phenyl-1H-pyrazol-3-yl]-1-methyl-2-propynyl-N-hydroxy-N-methyl-dithiocarbamate;

3-[1-[(4-aminosulfonyl)phenyl]-5-(4-chlorophenyl)-1H-pyrazol-3-yl]-1-methyl-2-propynyl-N-hydroxy-N-methyl-dithiocarbamate;

3-[3-[(4-aminosulfonyl)phenyl]-4-phenyl-1H-pyrazol-1-yl]-1-methyl-2-propynyl-N-hydroxy-N-methyl-dithiocarbamate;

3-[3-[(4-aminosulfonyl)phenyl]-4-(4-chlorophenyl)-1H-pyrazol-1-yl]-1-methyl-2-propynyl-N-hydroxy-N-methyl-dithiocarbamate;

3-[1-[(4-aminosulfonyl)phenyl]-5-(4-fluorophenyl)-1H-pyrazol-3-yl]-1-methyl-2-propynyl-N-hydroxy-N-methyl-dithiocarbamate;

3-[1-[(4-aminosulfonyl)phenyl]-5-(4-methoxyphenyl)-1H-pyrazol-3-yl]-1-methyl-2-propynyl-N-hydroxy-N-methyl-dithiocarbamate;

3-[1-[(4-aminosulfonyl)phenyl]-5-(3-chloro-4-methoxyphenyl)-1H-pyrazol-3-yl]-1-methyl-2-propynyl-N-hydroxy-N-methyl-dithiocarbamate;

3-[1-[(4-aminosulfonyl)phenyl]-5-(3-fluoro-4-methoxyphenyl)-1H-pyrazol-3-yl]-1-methyl-2-propynyl-N-hydroxy-N-methyl-dithiocarbamate;

3-[1-[(4-aminosulfonyl)phenyl]-5-(3-chloro-4-fluorophenyl)-1H-pyrazol-3-yl]-1-methyl-2-propynyl-N-hydroxy-N-methyl-dithiocarbamate;

3-[1-[(4-methylsulfonyl)phenyl]-5-phenyl-1H-pyrazol-3-yl]-1-methyl-2-propynyl-N-hydroxy-N-methyl-dithiocarbamate;

3-[5-(4-chlorophenyl)-1-[(4-methylsulfonyl)phenyl]-1H-pyrazol-3-yl]-1-methyl-2-propynyl-N-hydroxy-N-methyl-dithiocarbamate;

3-[4-[(4-methylsulfonyl)phenyl]-3-phenyl-1H-pyrazol-1-yl]-1-methyl-2-propynyl-N-hydroxy-N-methyl-dithiocarbamate;

3-[4-(4-chlorophenyl)-3-[(4-methylsulfonyl)phenyl]-1H-pyrazol-1-yl]-1-methyl-2-propynyl-N-hydroxy-N-methyl-dithiocarbamate;

[[4-[(4-aminosulfonyl)phenyl]-3-phenyl-5-isoxazolyl]-1-methyl-2-propenyl]-N-hydroxy-N-methyl-dithiocarbamate;

3-[[4-[(4-aminosulfonyl)phenyl]-3-(4-chlorophenyl)-5-isoxazolyl]-1-methyl-2-propenyl]-N-hydroxy-N-methyl-dithiocarbamate;

3-[[4-[(4-aminosulfonyl)phenyl]-3-(4-fluorophenyl)-5-isoxazolyl]-1-methyl-2-propenyl]-N-hydroxy-N-methyl-dithiocarbamate;

3-[[4-[(4-aminosulfonyl)phenyl]-3-(4-methoxyphenyl)-5-isoxazolyl]-1-methyl-2-propenyl]-N-hydroxy-N-methyl-dithiocarbamate;

3-[[4-[(4-aminosulfonyl)phenyl]-3-(3-chloro-4-methoxyphenyl)-5-isoxazolyl]-1-methyl-2-propenyl]-N-hydroxy-N-methyl-dithiocarbamate;

3-[[4-[(4-aminosulfonyl)phenyl]-3-(3-fluoro-4-methoxyphenyl)-5-isoxazolyl]-1-methyl-2-propenyl]-N-hydroxy-N-methyl-dithiocarbamate;

3-[[4-[(4-aminosulfonyl)phenyl]-3-(3-chloro-4-fluorophenyl)-5-isoxazolyl]-1-methyl-2-propenyl]-N-hydroxy-N-methyl-dithiocarbamate;

3-[[4-[(4-methylsulfonyl)phenyl]-3-phenyl-5-isoxazolyl]-1-methyl-2-propenyl]-N-hydroxy-N-methyl-dithiocarbamate;

3-[[3-(4-chlorophenyl)-4-[(4-methylsulfonyl)phenyl]-5-isoxazolyl]-1-methyl-2-propenyl]-N-hydroxy-N-methyl-dithiocarbamate;

3-[[4-[(4-aminosulfonyl)phenyl]-3-phenyl-2-thienyl]-1-methyl-2-propenyl]-N-hydroxy-N-methyl-dithiocarbamate;

3-[[4-[(4-aminosulfonyl)phenyl]-3-(4-chlorophenyl)-2-thienyl]-1-methyl-2-propenyl]-N-hydroxy-N-methyl-dithiocarbamate;

3-[[4-[(4-aminosulfonyl)phenyl]-3-(4-fluorophenyl)-2-thienyl]-1-methyl-2-propenyl]-N-hydroxy-N-methyl-dithiocarbamate;

3-[[4-[(4-aminosulfonyl)phenyl]-3-(4-methoxyphenyl)-2-thienyl]-1-methyl-2-propenyl]-N-hydroxy-N-methyl-dithiocarbamate;

3-[[4-[(4-aminosulfonyl)phenyl]-3-(3-chloro-4-methoxyphenyl)-2-thienyl]-1-methyl-2-propenyl]-N-hydroxy-N-methyl-dithiocarbamate;

3-[[4-[(4-aminosulfonyl)phenyl]-3-(3-fluoro-4-methoxyphenyl)-2-thienyl]-1-methyl-2-propenyl]-N-hydroxy-N-methyl-dithiocarbamate;

3-[[4-[(4-aminosulfonyl)phenyl]-3-(3-chloro-4-fluorophenyl)-2-thienyl]-1-methyl-2-propenyl]-N-hydroxy-N-methyl-dithiocarbamate;

3-[[3-[(4-methylsulfonyl)phenyl]-4-phenyl-5-thienyl]-1-methyl-2-propenyl]-N-hydroxy-N-methyl-dithiocarbamate;

3-[[4-(4-chlorophenyl)-3-[(4-methylsulfonyl)phenyl]-5-thienyl]-1-methyl-2-propenyl]-N-hydroxy-N-methyl-dithiocarbamate;

3-[[5-[(4-aminosulfonyl)phenyl]-6-phenyl-3-pyridyl]-1-methyl-2-propenyl]-N-hydroxy-N-methyl-dithiocarbamate;

3-[[5-[(4-aminosulfonyl)phenyl]-6-(4-chlorophenyl)-3-pyridyl]-1-methyl-2-propenyl]-N-hydroxy-N-methyl-dithiocarbamate;

3-[[5-[(4-aminosulfonyl)phenyl]-6-(4-fluorophenyl)-3-pyridyl]-1-methyl-2-propenyl]-N-hydroxy-N-methyl-dithiocarbamate;

3-[[5-[(4-aminosulfonyl)phenyl]-6-(4-methoxyphenyl)-3-pyridyl]-1-methyl-2-propenyl]-N-hydroxy-N-methyl-dithiocarbamate;

3-[[6-[(4-aminosulfonyl)phenyl]-5-(3-chloro-4-methoxyphenyl)-3-pyridyl]-1-methyl-2-propenyl]-N-hydroxy-N-methyl-dithiocarbamate;

3-[[6-[(4-aminosulfonyl)phenyl]-5-(3-fluoro-4-methoxyphenyl)-3-pyridyl]-1-methyl-2-propenyl]-N-hydroxy-N-methyl-dithiocarbamate;

3-[[5-[(4-aminosulfonyl)phenyl]-6-(3-chloro-4-fluorophenyl)-3-pyridyl]-1-methyl-2-propenyl]-N-hydroxy-N-methyl-dithiocarbamate;

3-[[5-[(4-methylsulfonyl)phenyl]-6-phenyl-3-pyridyl]-1-methyl-2-propenyl]-N-hydroxy-N-methyl-dithiocarbamate;

3-[[5-(4-chlorophenyl)-6-[(4-methylsulfonyl)phenyl]-3-pyridyl]-1-methyl-2-propenyl]-N-hydroxy-N-methyl-dithiocarbamate;

3-[[4-[(4-aminosulfonyl)phenyl]-3-phenyl-2-furyl]-1-methyl-2-propenyl]-N-hydroxy-N-methyl-dithiocarbamate;
3-[[4-[(4-aminosulfonyl)phenyl]-3-(4-chlorophenyl)-2-furyl]-1-methyl-2-propenyl]-N-hydroxy-N-methyl-dithiocarbamate;
3-[[4-[(4-aminosulfonyl)phenyl]-3-(4-fluorophenyl)-2-furyl]-1-methyl-2-propenyl]-N-hydroxy-N-methyl-dithiocarbamate;
3-[[5-[(4-aminosulfonyl)phenyl]-4-(4-methoxyphenyl)-2-furyl]-1-methyl-2-propenyl]-N-hydroxy-N-methyl-dithiocarbamate;
3-[[4-[(4-aminosulfonyl)phenyl]-5-(3-chloro-4-methoxyphenyl)-2-furyl]-1-methyl-2-propenyl]-N-hydroxy-N-methyl-dithiocarbamate;
3-[[5-[(4-aminosulfonyl)phenyl]-4-(3-fluoro-4-methoxyphenyl)-2-furyl]-1-methyl-2-propenyl]-N-hydroxy-N-methyl-dithiocarbamate;
3-[[4-[(4-aminosulfonyl)phenyl]-5-(3-chloro-4-fluorophenyl)-2-furyl]-1-methyl-2-propenyl]-N-hydroxy-N-methyl-dithiocarbamate;
3-[[4-[(4-methylsulfonyl)phenyl]-3-phenyl-2-furyl]-1-methyl-2-propenyl]-N-hydroxy-N-methyl-dithiocarbamate;
3-[[4-(4-chlorophenyl)-5-[(4-methylsulfonyl)phenyl]-2-furyl]-1-methyl-2-propenyl]-N-hydroxy-N-methyl-dithiocarbamate;
3-[[4-[(4-aminosulfonyl)phenyl]-5-phenyl-2-oxazolyl]-1-methyl-2-propenyl]-N-hydroxy-N-methyl-dithiocarbamate;
3-[[4-[(4-aminosulfonyl)phenyl]-5-(4-chlorophenyl)-2-oxazolyl]-1-methyl-2-propenyl]-N-hydroxy-N-methyl-dithiocarbamate;
3-[[5-[(4-aminosulfonyl)phenyl]-4-phenyl-2-oxazolyl]-1-methyl-2-propenyl]-N-hydroxy-N-methyl-dithiocarbamate;
3-[[5-[(4-aminosulfonyl)phenyl]-4-(4-chlorophenyl)-2-oxazolyl]-1-methyl-2-propenyl]-N-hydroxy-N-methyl-dithiocarbamate;
3-[[5-[(4-aminosulfonyl)phenyl]-4-(4-fluorophenyl)-2-oxazolyl]-1-methyl-2-propenyl]-N-hydroxy-N-methyl-dithiocarbamate;
3-[[5-[(4-aminosulfonyl)phenyl]-4-(4-methoxyphenyl)-2-oxazolyl]-1-methyl-2-propenyl]-N-hydroxy-N-methyl-dithiocarbamate;
3-[[5-[(4-aminosulfonyl)phenyl]-4-(3-chloro-4-methoxyphenyl)-2-oxazolyl]-1-methyl-2-propenyl]-N-hydroxy-N-methyl-dithiocarbamate;
3-[[5-[(4-aminosulfonyl)phenyl]-4-(3-fluoro-4-methoxyphenyl)-2-oxazolyl]-1-methyl-2-propenyl]-N-hydroxy-N-methyl-dithiocarbamate;
3-[[5-[(4-aminosulfonyl)phenyl]-4-(3-chloro-4-fluorophenyl)-2-oxazolyl]-1-methyl-2-propenyl]-N-hydroxy-N-methyl-dithiocarbamate;
3-[[4-[(4-methylsulfonyl)phenyl]-4-phenyl-2-oxazolyl]-1-methyl-2-propenyl]-N-hydroxy-N-methyl-dithiocarbamate;
3-[[5-(4-chlorophenyl)-4-[(4-methylsulfonyl)phenyl]-2-oxazolyl]-1-methyl-2-propenyl]-N-hydroxy-N-methyl-dithiocarbamate;
3-[[5-[(4-methylsulfonyl)phenyl]-4-phenyl-2-oxazolyl]-1-methyl-2-propenyl]-N-hydroxy-N-methyl-dithiocarbamate;
3-[[4-(4-chlorophenyl)-5-[(4-methylsulfonyl)phenyl]-2-oxazolyl]-1-methyl-2-propenyl]-N-hydroxy-N-methyl-dithiocarbamate;
3-[4-[(4-aminosulfonyl)phenyl]-5-phenyl-2-oxazolyl]phenyl-N-hydroxy-N-methyl-dithiocarbamate;
3-[4-[(4-aminosulfonyl)phenyl]-5-(4-chlorophenyl)-2-oxazolyl]phenyl-N-hydroxy-N-methyl-dithiocarbamate;
3-[5-[(4-aminosulfonyl)phenyl]-4-phenyl-2-oxazolyl]phenyl-N-hydroxy-N-methyl-dithiocarbamate;
4-[5-[(4-aminosulfonyl)phenyl]-4-(4-chlorophenyl)-2-oxazolyl]phenyl-N-hydroxy-N-methyl-dithiocarbamate;
4-[5-[(4-aminosulfonyl)phenyl]-4-(4-fluorophenyl)-2-oxazolyl]phenyl-N-hydroxy-N-methyl-dithiocarbamate;
4-[5-[(4-aminosulfonyl)phenyl]-4-(4-methoxyphenyl)-2-oxazolyl]phenyl-N-hydroxy-N-methyl-dithiocarbamate;
4-[5-[(4-aminosulfonyl)phenyl]-4-(3-chloro-4-methoxyphenyl)-2-oxazolyl]phenyl-N-hydroxy-N-methyl-dithiocarbamate;
4-[5-[(4-aminosulfonyl)phenyl]-4-(3-fluoro-4-methoxyphenyl)-2-oxazolyl]phenyl-N-hydroxy-N-methyl-dithiocarbamate;
4-[5-[(4-aminosulfonyl)phenyl]-4-(3-chloro-4-fluorophenyl)-2-oxazolyl]phenyl-N-hydroxy-N-methyl-dithiocarbamate;
4-[4-[(4-methylsulfonyl)phenyl]-5-phenyl-2-oxazolyl]phenyl-N-hydroxy-N-methyl-dithiocarbamate;
4-[5-(4-chlorophenyl)-4-[(4-methylsulfonyl)phenyl]-2-oxazolyl]phenyl-N-hydroxy-N-methyl-dithiocarbamate;
3-[5-[(4-methylsulfonyl)phenyl]-4-phenyl-2-oxazolyl]phenyl-N-hydroxy-N-methyl-dithiocarbamate;
3-[4-(4-chlorophenyl)-5-[(4-methylsulfonyl)phenyl]-2-oxazolyl]phenyl-N-hydroxy-N-methyl-dithiocarbamate;
4-[1-[(4-aminosulfonyl)phenyl]-5-phenyl-1H-pyrazol-3-yl]phenyl-N-hydroxy-N-methyl-dithiocarbamate;
4-[1-[(4-aminosulfonyl)phenyl]-5-(4-chlorophenyl)-1H-pyrazol-3-yl]phenyl-N-hydroxy-N-methyl-dithiocarbamate;
4-[3-[(4-aminosulfonyl)phenyl]-4-phenyl-1H-pyrazol-1-yl]phenyl-N-hydroxy-N-methyl-dithiocarbamate;
3-[3-[(4-aminosulfonyl)phenyl]-4-(4-chlorophenyl)-1H-pyrazol-1-yl]phenyl-N-hydroxy-N-methyl-dithiocarbamate;
3-[1-[(4-aminosulfonyl)phenyl]-5-(4-fluorophenyl)-1H-pyrazol-3-yl]phenyl-N-hydroxy-N-methyl-dithiocarbamate;
4-[1-[(4-aminosulfonyl)phenyl]-5-(4-methoxyphenyl)-1H-pyrazol-3-yl]phenyl-N-hydroxy-N-methyl-dithiocarbamate;
4-[1-[(4-aminosulfonyl)phenyl]-5-(3-chloro-4-methoxyphenyl)-1H-pyrazol-3-yl]phenyl-N-hydroxy-N-methyl-dithiocarbamate;
3-[1-[(4-aminosulfonyl)phenyl]-5-(3-fluoro-4-methoxyphenyl)-1H-pyrazol-3-yl]phenyl-N-hydroxy-N-methyl-dithiocarbamate;
4-[1-[(4-aminosulfonyl)phenyl]-5-(3-chloro-4-fluorophenyl)-1H-pyrazol-3-yl]phenyl-N-hydroxy-N-methyl-dithiocarbamate;
4[-1-[(4-methylsulfonyl)phenyl]-5-phenyl-1H-pyrazol-3-yl]phenyl-N-hydroxy-N-methyl-dithiocarbamate;
4-[5-(4-chlorophenyl)-1-[(4-methylsulfonyl)phenyl]-1H-pyrazol-3-yl]phenyl-N-hydroxy-N-methyl-dithiocarbamate;
3-[4-[(4-methylsulfonyl)phenyl]-3-phenyl-1H-pyrazol-1-yl]phenyl-N-hydroxy-N-methyl-dithiocarbamate;
3-[4-(4-chlorophenyl)-3-[(4-methylsulfonyl)phenyl]-1H-pyrazol-1-yl]phenyl-N-hydroxy-N-methyl-dithiocarbamate;
5-[4-[(4-aminosulfonyl)phenyl]-5-phenyl-2-oxazolyl]1,2,3-triazol-4-ylmethyl-N-hydroxy-N-methyl-dithiocarbamate;
5-[4-[(4-aminosulfonyl)phenyl]-5-(4-chlorophenyl)-2-oxazolyl]1,2,3-triazol-4-ylmethyl-N-hydroxy-N-methyl-dithiocarbamate;

5-[5-[(4-aminosulfonyl)phenyl]-4-phenyl-2-oxazolyl]1,2,3-triazol-4-ylmethyl-N-hydroxy-N-methyl-dithiocarbamate;
5-[5-[(4-aminosulfonyl)phenyl]-4-(4-chlorophenyl)-2-oxazolyl]1,2,3-triazol-4-ylmethyl-N-hydroxy-N-methyl-dithiocarbamate;
5-[5-[(4-aminosulfonyl)phenyl]-4-(4-fluorophenyl)-2-oxazolyl]1,2,3-triazol-4-ylmethyl-N-hydroxy-N-methyl-dithiocarbamate;
5-[5-[(4-aminosulfonyl)phenyl]-4-(4-methoxyphenyl)-2-oxazolyl]1,2,3-triazol-4-ylmethyl-N-hydroxy-N-methyl-dithiocarbamate;
5-[5-[(4-aminosulfonyl)phenyl]-4-(3-chloro-4-methoxyphenyl)-2-oxazolyl]1,2,3-triazol-4-ylmethyl-N-hydroxy-N-methyl-dithiocarbamate;
5-[5-[(4-aminosulfonyl)phenyl]-4-(3-fluoro-4-methoxyphenyl)-2-oxazolyl]1,2,3-triazol-4-ylmethyl-N-hydroxy-N-methyl-dithiocarbamate;
5-[5-[(4-aminosulfonyl)phenyl]-4-(3-chloro-4-fluorophenyl)-2-oxazolyl]1,2,3-triazol-4-ylmethyl-N-hydroxy-N-methyl-dithiocarbamate;
5-[4-[(4-methylsulfonyl)phenyl]-5-cyclohexyl-2-oxazolyl]1,2,3-triazol-4-ylmethyl-N-hydroxy-N-methyl-dithiocarbamate;
5-[5-(4-chlorophenyl)-4-[(4-methylsulfonyl)phenyl]-2-oxazolyl]1,2,3-triazol-4-ylmethyl-N-hydroxy-N-methyl-dithiocarbamate;
5-[5-[(4-methylsulfonyl)phenyl]-4-cyclohexenyl-2-oxazolyl]1,2,3-triazol-4-ylmethyl-N-hydroxy-N-methyl-dithiocarbamate;
5-[4-(4-chlorophenyl)-5-[(4-methylsulfonyl)phenyl]-2-oxazolyl]1,2,3-triazol-4-ylmethyl-N-hydroxy-N-methyl-dithiocarbamate;
3-[4-[(4-aminosulfonyl)phenyl]-5-phenyl-2-oxazolyl]cyclohexyl-N-hydroxy-N-methyl-dithiocarbamate;
3-[4-[(4-aminosulfonyl)phenyl]-5-(4-chlorophenyl)-2-oxazolyl]cyclohexyl-N-hydroxy-N-methyl-dithiocarbamate;
3-[5-[(4-aminosulfonyl)phenyl]-4-phenyl-2-oxazolyl]cyclohexyl-N-hydroxy-N-methyl-dithiocarbamate;
4-[5-[(4-aminosulfonyl)phenyl]-4-(4-chlorophenyl)-2-oxazolyl]cyclohexyl-N-hydroxy-N-methyl-dithiocarbamate;
4-[5-[(4-aminosulfonyl)phenyl]-4-(4-fluorophenyl)-2-oxazolyl]cyclohexyl-N-hydroxy-N-methyl-dithiocarbamate;
4-[5-[(4-aminosulfonyl)phenyl]-4-(4-methoxyphenyl)-2-oxazolyl]cyclohexyl-N-hydroxy-N-methyl-dithiocarbamate;
4-[5-[(4-aminosulfonyl)phenyl]-4-(3-chloro-4-methoxyphenyl)-2-oxazolyl]cyclohexyl-N-hydroxy-N-methyl-dithiocarbamate;
4-[5-[(4-aminosulfonyl)phenyl]-4-(3-fluoro-4-methoxyphenyl)-2-oxazolyl]cyclohexyl-N-hydroxy-N-methyl-dithiocarbamate;
4-[5-[(4-aminosulfonyl)phenyl]-4-(3-chloro-4-fluorophenyl)-2-oxazolyl]cyclohexyl-N-hydroxy-N-methyl-dithiocarbamate;
4-[4-[(4-methylsulfonyl)phenyl]-5-cyclohexyl-2-oxazolyl]cyclohexyl-N-hydroxy-N-methyl-dithiocarbamate;
4-[5-(4-chlorophenyl)-4-[(4-methylsulfonyl)phenyl]-2-oxazolyl]cyclohexyl-N-hydroxy-N-methyl-dithiocarbamate;
3-[5-[(4-methylsulfonyl)phenyl]-4-cyclohexenyl-2-oxazolyl]cyclohexyl-N-hydroxy-N-methyl-dithiocarbamate;
3-[4-(4-chlorophenyl)-5-[(4-methylsulfonyl)phenyl]-2-oxazolyl]cyclohexyl-N-hydroxy-N-methyl-dithiocarbamate;
4-[(4-aminosulfonyl)phenyl]-5-(3,4-dichlorophenyl)-N-hydroxy-2-oxazolebutanamide;
4-[(4-aminosulfonyl)phenyl]-N-hydroxy-N-methyl-5-phenyl-2-oxazolebutanamide;
4-[(4-aminosulfonyl)phenyl]-5-(4-chlorophenyl)-N-hydroxy-2-oxazolebutanamide;
5-[(4-aminosulfonyl)phenyl]-N-hydroxy-N-methyl-4-phenyl-2-oxazolebutanamide;
5-[(4-aminosulfonyl)phenyl]-4-(4-chlorophenyl)-N-hydroxy-2-oxazolebutanamide;
5-[(4-aminosulfonyl)phenyl]-4-(4-fluorophenyl)-N-hydroxy-N-methyl-2-oxazolebutanamide;
5-[(4-aminosulfonyl)phenyl]-4-(4-methoxyphenyl)-N-hydroxy-2-oxazolebutanamide;
5-[(4-aminosulfonyl)phenyl]-4-(3-chloro-4-methoxyphenyl)-N-hydroxy-2-oxazolebutanamide;
5-[(4-aminosulfonyl)phenyl]-4-(3-fluoro-4-methoxyphenyl)-N-hydroxy-N-methyl-2-oxazolebutanamide;
5-[(4-aminosulfonyl)phenyl]-4-(3-chloro-4-fluorophenyl)-N-hydroxy-2-oxazolebutanamide;
N-hydroxy-N-methyl-4-[(4-methylsulfonyl)phenyl]-5-phenyl-2-oxazolebutanamide;
5-(4-chlorophenyl)-N-hydroxy-N-methyl-4-[(4-methylsulfonyl)phenyl]-2-oxazolebutanamide;
5-[(4-methylsulfonyl)phenyl]-N-hydroxy-N-methyl-4-phenyl-2-oxazolebutanamide;
4-(4-chlorophenyl)-5-[(4-methylsulfonyl)phenyl]-N-hydroxy-2-oxazolebutanamide;
1-[(4-aminosulfonyl)phenyl]-N-hydroxy-N-methyl-5-phenyl-3-pyrazolebutanamide;
1-[(4-aminosulfonyl)phenyl]-5-(4-chlorophenyl)-N-hydroxy-N-methyl-3-pyrazolebutanamide;
1-[(4-aminosulfonyl)phenyl]-5-(4-fluorophenyl)-N-hydroxy-N-methyl-3-pyrazolebutanamide;
1-[(4-aminosulfonyl)phenyl]-5-(4-methylphenyl)-N-hydroxy-N-methyl-3-pyrazolebutanamide;
1-[(4-aminosulfonyl)phenyl]-5-(3-chloro-4-methylphenyl)-N-hydroxy-3-pyrazolebutanamide;
1-[(4-aminosulfonyl)phenyl]-5-(3-fluoro-4-methylphenyl)-N-hydroxy-3-pyrazolebutanamide;
1-[(4-aminosulfonyl)phenyl]-5-(3-chloro-4-fluorophenyl)-N-hydroxy-3-pyrazolebutanamide;
4-[(4-aminosulfonyl)phenyl]-N-hydroxy-3-phenyl-5-isoxazole-N-methyl-butanamide;
4-[(4-aminosulfonyl)phenyl]-3-(4-chlorophenyl)-N-hydroxy-5-isoxazole-N-methyl-butanamide;
4-[(4-aminosulfonyl)phenyl]-3-(4-fluorophenyl)-N-hydroxy-5-isoxazole-N-methyl-butanamide;
4-[(4-aminosulfonyl)phenyl]-3-(4-methoxyphenyl)-N-hydroxy-5-isoxazole-butanamide;
4-[(4-aminosulfonyl)phenyl]-3-(3-chloro-4-methoxyphenyl)-N-hydroxy-5-isoxazole-butanamide;
4-[(4-aminosulfonyl)phenyl]-3-(3-fluoro-4-methoxyphenyl)-N-hydroxy-5-isoxazole-butanamide;
4-[(4-aminosulfonyl)phenyl]-3-(3-chloro-4-fluorophenyl)-N-hydroxy-5-isoxazole-butanamide;
4-[(4-methylsulfonyl)phenyl]-N-hydroxy-3-phenyl-5-isoxazole-N-methyl-butanamide;
3-(4-chlorophenyl)-N-hydroxy-N-methyl-4-[(4-methylsulfonyl)phenyl]-5-isoxazolebutanamide;
4-[(4-aminosulfonyl)phenyl]-3-(3,4-dichlorophenyl)-N-hydroxy-5-isoxazole-N-methyl-butanamide;
4-[(4-aminosulfonyl)phenyl]-3-(3-fluorophenyl)-N-hydroxy-5-isoxazole-N-methyl-butanamide;
4-[(4-aminosulfonyl)phenyl]-3-(3-fluorophenyl)-N-hydroxy-5-isoxazole-butanamide;

4-[(4-aminosulfonyl)phenyl]-3-(3,4-dichlorophenyl)-N-hydroxy-5-isoxazole-butanamide;
3-(3-fluorophenyl)-4-[(4-methylsulfonyl)phenyl]-N-hydroxy-5-isoxazole-N-methyl-butanamide;
3-(3,4-dichlorophenyl)-N-hydroxy-4-[(4-methylsulfonyl)phenyl]-5-isoxazolebutanamide;
4-[(4-aminosulfonyl)phenyl]-N-hydroxy-N-methyl-3-phenyl-2-thiophenebutanamide;
4-[(4-aminosulfonyl)phenyl]-3-(4-chlorophenyl)-N-hydroxy-N-methyl-2-thiophenebutanamide;
4-[(4-aminosulfonyl)phenyl]-3-(4-fluorophenyl)-N-hydroxy-N-methyl-2-thiophenebutanamide;
[4-[(4-aminosulfonyl)phenyl]-3-(4-methoxyphenyl)-N-hydroxy-N-methyl-2-thiophenebutanamide;
[4-[(4-aminosulfonyl)phenyl]-3-(3-chloro-4-methoxyphenyl)-N-hydroxy-2-thiophenebutanamide;
[4-[(4-aminosulfonyl)phenyl]-3-(3-fluoro-4-methoxyphenyl)-N-hydroxy-2-thiophenebutanamide;
[4-[(4-aminosulfonyl)phenyl]-3-(3-chloro-4-fluorophenyl)-N-hydroxy-2-thiophenebutanamide;
[3-[(4-methylsulfonyl)phenyl]-N-hydroxy-N-methyl-4-phenyl-5-thiophenebutanamide;
[4-(4-chlorophenyl)-N-hydroxy-N-methyl-3-[(4-methylsulfonyl)phenyl]-5-thiophenebutanamide;
[5-[(4-aminosulfonyl)phenyl]-N-hydroxy-N-methyl-6-phenyl-3-pyridinebutanamide;
[5-[(4-aminosulfonyl)phenyl]-6-(4-chlorophenyl)-N-hydroxy-3-pyridinebutanamide;
[5-[(4-aminosulfonyl)phenyl]-6-(4-fluorophenyl)-N-hydroxy-N-methyl-3-pyridinebutanamide;
[5-[(4-aminosulfonyl)phenyl]-6-(4-methoxyphenyl)-N-hydroxy-N-methyl-3-pyridinebutanamide;
[6-[(4-aminosulfonyl)phenyl]-5-(3-chloro-4-methoxyphenyl)-N-hydroxy-3-pyridinebutanamide;
[6-[(4-aminosulfonyl)phenyl]-5-(3-fluoro-3-fluoro-4-methoxyphenyl)-N-hydroxy-3-pyridinebutanamide;
[5-[(4-aminosulfonyl)phenyl]-6-(3-chloro-4-fluorophenyl)-N-hydroxy-N-methyl-3-pyridinebutanamide;
[5-[(4-methylsulfonyl)phenyl]-N-hydroxy-N-methyl-6-phenyl-3-pyridinebutanamide;
[5-(4-chlorophenyl)-N-hydroxy-6-[(4-methylsulfonyl)phenyl]-3-pyridinebutanamide;
[4-[(4-aminosulfonyl)phenyl]-N-hydroxy-N-methyl-3-phenyl-2-furanbutanamide;
[4-[(4-aminosulfonyl)phenyl]-3-(4-chlorophenyl)-N-hydroxy-2-furanbutanamide;
[4-[(4-aminosulfonyl)phenyl]-3-(4-fluorophenyl)-N-hydroxy-N-methyl-2-furanbutanamide;
[5-[(4-aminosulfonyl)phenyl]-N-hydroxy-4-(4-methoxyphenyl)-2-furanbutanamide;
[4-[(4-aminosulfonyl)phenyl]-5-(3-chloro-4-methoxyphenyl)-N-hydroxy-2-furanbutanamide;
[5-[(4-aminosulfonyl)phenyl]-4-(3-fluoro-4-methoxyphenyl)-N-hydroxy-2-furanbutanamide;
[4-[(4-aminosulfonyl)phenyl]-5-(3-chloro-4-fluorophenyl)-N-hydroxy-N-methyl-2-furanbutanamide;
[4-[(4-methylsulfonyl)phenyl]-N-hydroxy-3-phenyl-2-furanbutanamide;
[4-(4-chlorophenyl)-N-hydroxy-N-methyl-5-[(4-methylsulfonyl)phenyl]-2-furanbutanamide;
4-[(4-aminosulfonyl)phenyl]-N-hydroxy-N-methyl-5-phenyl-2-oxazolepropanamide;
4-[(4-aminosulfonyl)phenyl]-5-(4-chlorophenyl)-N-hydroxy-N-methyl-2-oxazolepropanamide;
5-[(4-aminosulfonyl)phenyl]-N-hydroxy-N-methyl-4-phenyl-2-oxazolepropanamide;
5-[(4-aminosulfonyl)phenyl]-4-(4-chlorophenyl)-N-hydroxy-N-methyl-2-oxazolepropanamide;
5-[(4-aminosulfonyl)phenyl]-4-(4-fluorophenyl)-N-hydroxy-N-methyl-2-oxazolepropanamide;
5-[(4-aminosulfonyl)phenyl]-4-(4-methoxyphenyl)-N-hydroxy-N-methyl-2-oxazolepropanamide;
5-[(4-aminosulfonyl)phenyl]-4-(3-chloro-4-methoxyphenyl)-N-hydroxy-N-methyl-2-oxazolepropanamide;
5-[(4-aminosulfonyl)phenyl]-4-(3-fluoro-4-methoxyphenyl)-N-hydroxy-N-methyl-2-oxazolepropanamide;
5-[(4-aminosulfonyl)phenyl]-4-(3-chloro-4-fluorophenyl)-N-hydroxy-N-methyl-2-oxazolepropanamide;
N-hydroxy-N-methyl-4-[(4-methylsulfonyl)phenyl]-5-phenyl-2-oxazolepropanamide;
5-(4-chlorophenyl)-N-hydroxy-N-methyl-4-[(4-methylsulfonyl)phenyl]-2-oxazolepropanamide;
5-[(4-methylsulfonyl)phenyl]-N-hydroxy-N-methyl-4-phenyl-2-oxazolepropanamide;
4-(4-chlorophenyl)-5-[(4-methylsulfonyl)phenyl]-N-hydroxy-N-methyl-2-oxazolepropanamide;
1-[(4-aminosulfonyl)phenyl]-N-hydroxy-N-methyl-5-phenyl-3-pyrazolepropanamide;
1-[(4-aminosulfonyl)phenyl]-5-(4-chlorophenyl)-N-hydroxy-N-methyl-3-pyrazolepropanamide;
1-[(4-aminosulfonyl)phenyl]-5-(4-fluorophenyl)-N-hydroxy-N-methyl-3-pyrazolepropanamide;
1-[(4-aminosulfonyl)phenyl]-5-(4-methylphenyl)-N-hydroxy-N-methyl-3-pyrazolepropanamide;
1-[(4-aminosulfonyl)phenyl]-5-(3-chloro-4-methylphenyl)-N-hydroxy-N-methyl-3-pyrazolepropanamide;
1-[(4-aminosulfonyl)phenyl]-5-(3-fluoro-4-methylphenyl)-N-hydroxy-N-methyl-3-pyrazolepropanamide;
1-[(4-aminosulfonyl)phenyl]-5-(3-chloro-4-fluorophenyl)-N-hydroxy-N-methyl-3-pyrazolepropanamide;
4-[(4-aminosulfonyl)phenyl]-N-hydroxy-3-phenyl-5-isoxazole-N-methyl-propanamide;
4-[(4-aminosulfonyl)phenyl]-3-(4-chlorophenyl)-N-hydroxy-5-isoxazole-N-methyl-propanamide;
4-[(4-aminosulfonyl)phenyl]-3-(4-fluorophenyl)-N-hydroxy-5-isoxazole-N-methyl-propanamide;
4-[(4-aminosulfonyl)phenyl]-3-(4-methoxyphenyl)-N-hydroxy-5-isoxazole-N-methyl-propanamide;
4-[(4-aminosulfonyl)phenyl]-3-(3-chloro-4-methoxyphenyl)-N-hydroxy-5-isoxazole-N-methyl-propanamide;
4-[(4-aminosulfonyl)phenyl]-3-(3-fluoro-4-methoxyphenyl)-N-hydroxy-5-isoxazole-N-methyl-propanamide;
4-[(4-aminosulfonyl)phenyl]-3-(3-chloro-4-fluorophenyl)-N-hydroxy-5-isoxazole-N-methyl-propanamide;
4-[(4-methylsulfonyl)phenyl]-N-hydroxy-3-phenyl-5-isoxazole-N-methyl-propanamide;
3-(4-chlorophenyl)-N-hydroxy-N-methyl-4-[(4-methylsulfonyl)phenyl]-5-isoxazolepropanamide;
4-[(4-aminosulfonyl)phenyl]-N-hydroxy-N-methyl-3-phenyl-2-thiophenepropanamide;
4-[(4-aminosulfonyl)phenyl]-3-(4-chlorophenyl)-N-hydroxy-N-methyl-2-thiophenepropanamide;
4-[(4-aminosulfonyl)phenyl)-3-(4-fluorophenyl)-N-hydroxy-N-methyl-2-thiophenepropanamide;
[4-[(4-aminosulfonyl)phenyl]-3-(4-methoxyphenyl)-N-hydroxy-N-methyl-2-thiophenepropanamide;
[4-[(4-aminosulfonyl)phenyl]-3-(3-chloro-4-methoxyphenyl)-N-hydroxy-N-methyl-2-thiophenepropanamide;
[4-[(4-aminosulfonyl)phenyl]-3-(3-fluoro-4-methoxyphenyl)-N-hydroxy-N-methyl-2-thiophenepropanamide;

[4-[(4-aminosulfonyl)phenyl]-3-(3-chloro-4-fluorophenyl)-N-hydroxy-N-methyl-2-thiophenepropanamide;
[3-[(4-methylsulfonyl)phenyl]-N-hydroxy-N-methyl-4-phenyl-5-thiophenepropanamide;
[4-(4-chlorophenyl)-N-hydroxy-N-methyl-3-[(4-methylsulfonyl)phenyl]-5-thiophenepropanamide;
[5-[(4-aminosulfonyl)phenyl]-N-hydroxy-N-methyl-6-phenyl-3-pyridinepropanamide;
[5-[(4-aminosulfonyl)phenyl]-6-(4-chlorophenyl)-N-hydroxy-N-methyl-3-pyridinepropanamide;
[5-[(4-aminosulfonyl)phenyl]-6-(4-fluorophenyl)-N-hydroxy-N-methyl-3-pyridinepropanamide;
[5-[(4-aminosulfonyl)phenyl]-6-(4-methoxyphenyl)-N-hydroxy-N-methyl-3-pyridinepropanamide;
[6-[(4-aminosulfonyl)phenyl]-5-(3-chloro-4-methoxyphenyl)-N-hydroxy-N-methyl-3-pyridinepropanamide;
[6-[(4-aminosulfonyl)phenyl]-5-(3-fluoro-3-fluoro-4-methoxyphenyl)-N-hydroxy-N-methyl-3-pyridinepropanamide;
[5-[(4-aminosulfonyl)phenyl]-6-(3-chloro-4-fluorophenyl)-N-hydroxy-N-methyl-3-pyridinepropanamide;
[5-[(4-methylsulfonyl)phenyl]-N-hydroxy-N-methyl-6-phenyl-3-pyridinepropanamide;
[5-(4-chlorophenyl)-N-hydroxy-N-methyl-6-[(4-methylsulfonyl)phenyl]-3-pyridinepropanamide;
[4-[(4-aminosulfonyl)phenyl]-N-hydroxy-N-methyl-3-phenyl-2-furanpropanamide;
[4-[(4-aminosulfonyl)phenyl]-3-(4-chlorophenyl)-N-hydroxy-N-methyl-2-furanpropanamide;
[4-[(4-aminosulfonyl)phenyl]-3-(4-fluorophenyl)-N-hydroxy-N-methyl-2-furanpropanamide;
[5-[(4-aminosulfonyl)phenyl]-N-hydroxy-4-(4-methoxyphenyl)-N-methyl-2-furanpropanamide;
[4-[(4-aminosulfonyl)phenyl]-5-(3-chloro-4-methoxyphenyl)-N-hydroxy-N-methyl-2-furanpropanamide;
[5-[(4-aminosulfonyl)phenyl]-4-(3-fluoro-4-methoxyphenyl)-N-hydroxy-N-methyl-2-furanpropanamide;
[4-[(4-aminosulfonyl)phenyl]-5-(3-chloro-4-fluorophenyl)-N-hydroxy-N-methyl-2-furanpropanamide;
[4-[(4-methylsulfonyl)phenyl]-N-hydroxy-N-methyl-3-phenyl-2-furanpropanamide;
[4-(4-chlorophenyl)-N-hydroxy-N-methyl-5-[(4-methylsulfonyl)phenyl]-2-furanpropanamide;
4-[(4-aminosulfonyl)phenyl]-N-hydroxy-N-methyl-5-phenyl-2-oxazole-ethanamide;
4-[(4-aminosulfonyl)phenyl]-5-(4-chlorophenyl)-N-hydroxy-N-methyl-2-oxazole-ethanamide;
5-[(4-aminosulfonyl)phenyl]-N-hydroxy-N-methyl-4-phenyl-2-oxazole-ethanamide;
5-[(4-aminosulfonyl)phenyl]-4-(4-chlorophenyl)-N-hydroxy-N-methyl-2-oxazole-ethanamide;
5-[(4-aminosulfonyl)phenyl]-4-(4-fluorophenyl)-N-hydroxy-N-methyl-2-oxazole-ethanamide;
5-[(4-aminosulfonyl)phenyl]-4-(4-methoxyphenyl)-N-hydroxy-N-methyl-2-oxazole-ethanamide;
5-[(4-aminosulfonyl)phenyl]-4-(3-chloro-4-methoxyphenyl)-N-hydroxy-N-methyl-2-oxazole-ethanamide;
5-[(4-aminosulfonyl)phenyl]-4-(3-fluoro-4-methoxyphenyl)-N-hydroxy-N-methyl-2-oxazole-ethanamide;
5-[(4-aminosulfonyl)phenyl]-4-(3-chloro-4-fluorophenyl)-N-hydroxy-N-methyl-2-oxazole-ethanamide;
4-[(4-methylsulfonyl)phenyl]-N-hydroxy-N-methyl-5-phenyl-2-oxazole-ethanamide;
5-(4-chlorophenyl)-4-[(4-methylsulfonyl)phenyl]-N-hydroxy-N-methyl-2-oxazole-ethanamide;
5-[(4-methylsulfonyl)phenyl]-N-hydroxy-N-methyl-4-phenyl-2-oxazole-ethanamide;
4-(4-chlorophenyl)-5-[(4-methylsulfonyl)phenyl]-N-hydroxy-N-methyl-2-oxazole-ethanamide;
[1-(4-(aminosulfonyl)phenyl]-5-(4-chlorophenyl)-1H-pyrazol-3-yl]-N-hydroxy-N-methyl-ethanamide;
1-[4-[(4-aminosulfonyl)phenyl]-5-phenyl-2-oxazolyl]-N-hydroxy-N-methyl-2-propenamide;
1-[4-[(4-aminosulfonyl)phenyl]-5-(4-chlorophenyl)-2-oxazolyl]-N-hydroxy-N-methyl-2-propenamide;
1-[5-[(4-aminosulfonyl)phenyl]-4-phenyl-2-oxazolyl]-N-hydroxy-N-methyl-2-propenamide;
1-[5-[(4-aminosulfonyl)phenyl]-4-(4-chlorophenyl)-2-oxazolyl]-N-hydroxy-N-methyl-2-propenamide;
1-[5-[(4-aminosulfonyl)phenyl]-4-(4-fluorophenyl)-2-oxazolyl]-N-hydroxy-N-methyl-2-propenamide;
1-[5-[(4-aminosulfonyl)phenyl]-4-(4-methoxyphenyl)-2-oxazolyl]-N-hydroxy-N-methyl-2-propenamide;
1-[5-[(4-aminosulfonyl)phenyl]-4-(3-chloro-4-methoxyphenyl)-2-oxazolyl]-N-hydroxy-N-methyl-2-propenamide;
1-[5-[(4-aminosulfonyl)phenyl]-4-(3-fluoro-4-methoxyphenyl)-2-oxazolyl]-N-hydroxy-N-methyl-2-propenamide;
1-[5-[(4-aminosulfonyl)phenyl]-4-(3-chloro-4-fluorophenyl)-2-oxazolyl]-N-hydroxy-N-methyl-2-propenamide;
1-[4-(4-methylsulfonyl)phenyl]-5-phenyl-2-oxazolyl]-N-hydroxy-N-methyl-2-propenamide;
1-[5-(4-chlorophenyl)-4-[(4-methylsulfonyl)phenyl]-2-oxazolyl]-N-hydroxy-N-methyl-2-propenamide;
1-[5-[(4-methylsulfonyl)phenyl]-4-phenyl-2-oxazolyl]-N-hydroxy-N-methyl-2-propenamide;
1-[4-(4-chlorophenyl)-5-[(4-methylsulfonyl)phenyl]-2-oxazolyl]-N-hydroxy-N-methyl-2-propenamide;
1-[(1-(4-aminosulfonyl)phenyl]-5-phenyl-1H-pyrazol-3-yl]-N-hydroxy-N-methyl-2-propenamide;
1-[1-[(4-aminosulfonyl)phenyl]-5-(4-chlorophenyl)-1H-pyrazol-3-yl]-N-hydroxy-N-methyl-2-propenamide;
1-[3-[(4-aminosulfonyl)phenyl]-4-phenyl-1H-pyrazol-1-yl]-N-hydroxy-N-methyl-2-propenamide;
1-[3-[(4-aminosulfonyl)phenyl]-4-(4-chlorophenyl)-1H-pyrazol-1-yl]-N-hydroxy-N-methyl-2-propenamide;
1-[1-[(4-aminosulfonyl)phenyl]-5-(4-fluorophenyl)-1H-pyrazol-3-yl]-N-hydroxy-N-methyl-2-propenamide;
1-[1-[(4-aminosulfonyl)phenyl]-5-(4-methoxyphenyl)-1H-pyrazol-3-yl]-N-hydroxy-N-methyl-2-propenamide;
1-[1-[(4-aminosulfonyl)phenyl]-5-(3-chloro-4-methoxyphenyl)-1H-pyrazol-3-yl]-N-hydroxy-N-methyl-2-propenamide;
1-[1-[(4-aminosulfonyl)phenyl]-5-(3-fluoro-4-methoxyphenyl)-1H-pyrazol-3-yl]-N-hydroxy-N-methyl-2-propenamide;
1-[1-[(4-aminosulfonyl)phenyl]-5-(3-chloro-4-fluorophenyl)-1H-pyrazol-3-yl]-7N-hydroxy-N-methyl-2-propenamide;
1-[1-[(4-methylsulfonyl)phenyl]-5-phenyl-1H-pyrazol-3-yl]-N-hydroxy-N-methyl-2-propenamide;
1-[5-(4-chlorophenyl)-1-[(4-methylsulfonyl)phenyl]-1H-pyrazol-3-yl]-N-hydroxy-N-methyl-2-propenamide;
1-[4-[(4-methylsulfonyl)phenyl]-3-phenyl-1H-pyrazol-1-yl]-N-hydroxy-N-methyl-2-propenamide;
1-[4-(4-chlorophenyl)-3-[(4-methylsulfonyl)phenyl]-1H-pyrazol-1-yl]-N-hydroxy-N-methyl-2-propenamide;
1-[4-[(4-aminosulfonyl)phenyl]-5-phenyl-2-oxazolyl]-N-hydroxy-N-methyl-2-propynamide;

1-[4-[(4-aminosulfonyl)phenyl]-5-(4-chlorophenyl)-2-oxazolyl]-N-hydroxy-N-methyl-2-propynamide;
1-[5-[(4-aminosulfonyl)phenyl]-4-phenyl-2-oxazolyl]-N-hydroxy-N-methyl-2-propynamide;
1-[5-[(4-aminosulfonyl)phenyl]-4-(4-chlorophenyl)-2-oxazolyl]-N-hydroxy-N-methyl-2-propynamide;
1-[5-[(4-aminosulfonyl)phenyl]-4-(4-fluorophenyl)-2-oxazolyl]-N-hydroxy-N-methyl-2-propynamide;
1-[5-[(4-aminosulfonyl)phenyl]-4-(4-methoxyphenyl)-2-oxazolyl]-N-hydroxy-N-methyl-2-propynamide;
1-[5-[(4-aminosulfonyl)phenyl]-4-(3-chloro-4-methoxyphenyl)-2-oxazolyl]-N-hydroxy-N-methyl-2-propynamide;
1-[5-[(4-aminosulfonyl)phenyl]-4-(3-fluoro-4-methoxyphenyl)-2-oxazolyl]-N-hydroxy-N-methyl-2-propynamide;
1-[5-[(4-aminosulfonyl)phenyl]-4-(3-chloro-4-fluorophenyl)-2-oxazolyl]-N-hydroxy-N-methyl-2-propynamide;
1-[4-[(4-methylsulfonyl)phenyl]-5-phenyl-2-oxazolyl]-N-hydroxy-N-methyl-2-propynamide;
1-[5-(4-chlorophenyl)-4-[(4-methylsulfonyl)phenyl]-2-oxazolyl]-N-hydroxy-N-methyl-2-propynamide;
1-[5-[(4-methylsulfonyl)phenyl]-4-phenyl-2-oxazolyl]-N-hydroxy-N-methyl-2-propynamide;
1-[4-(4-chlorophenyl)-5-[(4-methylsulfonyl)phenyl]-2-oxazolyl]-N-hydroxy-N-methyl-2-propynamide;
1-[1-[(4-aminosulfonyl)phenyl]-5-phenyl-1H-pyrazol-3-yl]-N-hydroxy-N-methyl-2-propynamide;
1-[1-[(4-aminosulfonyl)phenyl]-5-(4-chlorophenyl)-1H-pyrazol-3-yl]-N-hydroxy-N-methyl-2-propynamide;
1-[3-[(4-aminosulfonyl)phenyl]-4-phenyl-1H-pyrazol-1-yl]-N-hydroxy-N-methyl-2-propynamide;
1-[3-[(4-aminosulfonyl)phenyl]-4-(4-chlorophenyl)-1H-pyrazol-1-yl]-N-hydroxy-N-methyl-2-propynamide;
1-1-[(4-aminosulfonyl)phenyl]-5-(4-fluorophenyl)-1H-pyrazol-3-yl]-N-hydroxy-N-methyl-2-propynamide;
1-[1-[(4-aminosulfonyl)phenyl]-5-(4-methoxyphenyl)-1H-pyrazol-3-yl]-N-hydroxy-N-methyl-2-propynamide;
1-[1-[(4-aminosulfonyl)phenyl]-5-(3-chloro-4-methoxyphenyl)-1H-pyrazol-3-yl]-N-hydroxy-N-methyl-2-propynamide;
1-[1-[(4-aminosulfonyl)phenyl]-5-(3-fluoro-4-methoxyphenyl)-1H-pyrazol-3-yl]-N-hydroxy-N-methyl-2-propynamide;
1-[1-[(4-aminosulfonyl)phenyl]-5-(3-chloro-4-fluorophenyl)-1H-pyrazol-3-yl]-N-hydroxy-N-methyl-2-propynamide;
1-[1-[(4-methylsulfonyl)phenyl]-5-phenyl-1H-pyrazol-3-yl]-N-hydroxy-N-methyl-2-propynamide;
1-[5-(4-chlorophenyl)-1-[(4-methylsulfonyl)phenyl]-1H-pyrazol-3-yl]-N-hydroxy-N-methyl-2-propynamide;
1-[4-[(4-methylsulfonyl)phenyl]-3-phenyl-1H-pyrazol-1-yl]-N-hydroxy-N-methyl-2-propynamide;
1-[4-(4-chlorophenyl)-3-[(4-methylsulfonyl)phenyl]-1H-pyrazol-1-yl]-N-hydroxy-N-methyl-2-propynamide;
2-methyl-3-[4-[(4-aminosulfonyl)phenyl]-N-hydroxy-N-methyl-5-phenyl-2-oxazolyl]-2-propynamide;
2-methyl-3-[4-[(4-aminosulfonyl)phenyl]-5-(4-chlorophenyl)-N-hydroxy-N-methyl-2-oxazolyl]-2-propynamide;
2-methyl-3-[5-[(4-aminosulfonyl)phenyl]-N-hydroxy-N-methyl-4-phenyl-2-oxazolyl]-2-propynamide;
2-methyl-3-[5-[(4-aminosulfonyl)phenyl]-4-(4-chlorophenyl)-N-hydroxy-N-methyl-2-oxazolyl]-2-propynamide;
2-methyl-3-[5-[(4-aminosulfonyl)phenyl]-4-(4-fluorophenyl)-N-hydroxy-N-methyl-2-oxazolyl]-2-propynamide;
2-methyl-3-[5-[(4-aminosulfonyl)phenyl]-4-(4-methoxyphenyl)-N-hydroxy-N-methyl-2-oxazolyl]-2-propynamide;
2-methyl-3-[5-[(4-aminosulfonyl)phenyl]-4-(3-chloro-4-methoxyphenyl)-N-hydroxy-N-methyl-2-oxazolyl]-2-propynamide;
2-methyl-3-[5-[(4-aminosulfonyl)phenyl]-4-(3-fluoro-4-methoxyphenyl)-N-hydroxy-N-methyl-2-oxazolyl]-2-propynamide;
2-methyl-3-[5-[(4-aminosulfonyl)phenyl]-4-(3-chloro-4-fluorophenyl)-N-hydroxy-N-methyl-2-oxazolyl]-2-propynamide;
2-methyl-3-[N-hydroxy-N-methyl-4-[(4-methylsulfonyl)phenyl]-5-phenyl-2-oxazolyl]-2-propynamide;
2-methyl-3-[5-(4-chlorophenyl)-N-hydroxy-N-methyl-4-[(4-methylsulfonyl)phenyl]-2-oxazolyl]-2-propynamide;
2-methyl-3-[5-[(4-methylsulfonyl)phenyl]-N-hydroxy-N-methyl-4-phenyl-2-oxazolyl]-2-propynamide;
2-methyl-3-(4-(4-chlorophenyl)-5-[(4-methylsulfonyl)phenyl]-N-hydroxy-N-methyl-2-oxazolyl]-2-propynamide;
2-methyl-3-[1-[(4-aminosulfonyl)phenyl]-N-hydroxy-N-methyl-5-phenyl-1H-pyrazol-3-yl]-2-propynamide;
2-methyl-3-[1-[(4-aminosulfonyl)phenyl]-5-(4-chlorophenyl)-N-hydroxy-N-methyl-1H-pyrazol-3-yl]-2-propynamide;
2-methyl-3-[1-[(4-aminosulfonyl)phenyl]-5-(4-fluorophenyl)-N-hydroxy-N-methyl-1H-pyrazol-3-yl]-2-propynamide;
2-methyl-3-(1-[(4-aminosulfonyl)phenyl]-5-(4-methylphenyl)-N-hydroxy-N-methyl-1H-pyrazol-3-yl]-2-propynamide;
2-methyl-3-[1-[(4-aminosulfonyl)phenyl]-5-(3-chloro-4-methylphenyl)-N-hydroxy-N-methyl-1H-pyrazol-3-yl]-2-propynamide;
2-methyl-3-[1-[(4-aminosulfonyl)phenyl]-5-(3-fluoro-4-methylphenyl)-N-hydroxy-N-methyl-1H-pyrazol-3-yl]-2-propynamide;
2-methyl-3-[1-[(4-aminosulfonyl)phenyl]-5-(3-chloro-4-fluorophenyl)-N-hydroxy-N-methyl-1H-pyrazol-3-yl]-2-propynamide;
2-methyl-3-[4-[(4-aminosulfonyl)phenyl]-N-hydroxy-3-phenyl-5-isoxazolyl]-N-methyl-2-propynamide;
2-methyl-3-[4-[(4-aminosulfonyl)phenyl]-3-(4-chlorophenyl)-N-hydroxy-5-isoxazolyl]-N-methyl-2-propynamide;
2-methyl-3-[4-[(4-aminosulfonyl)phenyl]-3-(4-fluorophenyl)-N-hydroxy-5-isoxazolyl]-N-methyl-2-propynamide;
2-methyl-3-[4-[(4-aminosulfonyl)phenyl]-3-(4-methoxyphenyl)-N-hydroxy-5-isoxazolyl]-N-methyl-2-propynamide;
2-methyl-3-[4-[(4-aminosulfonyl)phenyl]-3-(3-chloro-4-methoxyphenyl)-N-hydroxy-5-isoxazolyl]-N-methyl-2-propynamide;
2-methyl-3-[4-[(4-aminosulfonyl)phenyl]-3-(3-fluoro-4-methoxyphenyl)-N-hydroxy-5-isoxazolyl]-N-methyl-2-propynamide;
2-methyl-3-[4-[(4-aminosulfonyl)phenyl]-3-(3-chloro-4-fluorophenyl)-N-hydroxy-5-isoxazolyl]-N-methyl-2-propynamide;
2-methyl-3-[4-[(4-methylsulfonyl)phenyl]-N-hydroxy-3-phenyl-5-isoxazolyl]-N-methyl-2-propynamide;
2-methyl-3-[3-(4-chlorophenyl)-N-hydroxy-N-methyl-4-[(4-methylsulfonyl)phenyl]-5-isoxazolyl]-2-propynamide;
2-methyl-3-[4-[(4-aminosulfonyl)phenyl]-N-hydroxy-N-methyl-3-phenyl-2-thienyl]-2-propynamide;

2-methyl-3-[4-[(4-aminosulfonyl)phenyl]-3-(4-chlorophenyl)-N-hydroxy-N-methyl-2-thienyl]-2-propynamide;
2-methyl-3-[4-[(4-aminosulfonyl)phenyl]-3-(4-fluorophenyl)-N-hydroxy-N-methyl-2-thienyl]-2-propynamide;
2-methyl-3-[[4-[(4-aminosulfonyl)phenyl]-3-(4-methoxyphenyl)-N-hydroxy-N-methyl-2-thienyl]-2-propynamide;
2-methyl-3-[[4-[(4-aminosulfonyl)phenyl]-3-(3-chloro-4-methoxyphenyl)-N-hydroxy-N-methyl-2-thienyl]-2-propynamide;
2-methyl-3-[[4-[(4-aminosulfonyl)phenyl]-3-(3-fluoro-4-methoxyphenyl)-N-hydroxy-N-methyl-2-thienyl]-2-propynamide;
2-methyl-3-[[4-[(4-aminosulfonyl)phenyl]-3-(3-chloro-4-fluorophenyl)-N-hydroxy-N-methyl-2-thienyl]-2-propynamide;
2-methyl-3-[[3-[(4-methylsulfonyl)phenyl]-N-hydroxy-N-methyl-4-phenyl-5-thienyl]-2-propynamide;
2-methyl-3-[[4-(4-chlorophenyl)-N-hydroxy-N-methyl-3-[(4-methylsulfonyl)phenyl]-5-thienyl]-2-propynamide;
2-methyl-3-[[5-[(4-aminosulfonyl)phenyl]-N-hydroxy-N-methyl-6-phenyl-3-pyridyl]-2-propynamide;
2-methyl-3-[[5-[(4-aminosulfonyl)phenyl]-6-(4-chlorophenyl)-N-hydroxy-N-methyl-3-pyridyl]-2-propynamide;
2-methyl-3-[[5-[(4-aminosulfonyl)phenyl]-6-(4-fluorophenyl)-N-hydroxy-N-methyl-3-pyridyl]-2-propynamide;
2-methyl-3-[[5-[(4-aminosulfonyl)phenyl]-6-(4-methoxyphenyl)-N-hydroxy-N-methyl-3-pyridyl]-2-propynamide;
2-methyl-3-[[6-[(4-aminosulfonyl)phenyl]-5-(3-chloro-4-methoxyphenyl)-N-hydroxy-N-methyl-3-pyridyl]-2-propynamide;
2-methyl-3-[[6-[(4-aminosulfonyl)phenyl]-5-(3-fluoro-3-fluoro-4-methoxyphenyl)-N-hydroxy-N-methyl-3-pyridyl]-2-propynamide;
2-methyl-3-[[5-[(4-aminosulfonyl)phenyl]-6-(3-chloro-4-fluorophenyl)-N-hydroxy-N-methyl-3-pyridyl]-2-propynamide;
2-methyl-3-[[5-[(4-methylsulfonyl)phenyl]-N-hydroxy-N-methyl-6-phenyl-3-pyridyl]-2-propynamide;
2-methyl-3-[[5-(4-chlorophenyl)-N-hydroxy-N-methyl-6-[(4-methylsulfonyl)phenyl]-3-pyridyl]-2-propynamide;
2-methyl-3-[[4-[(4-aminosulfonyl)phenyl]-N-hydroxy-N-methyl-3-phenyl-2-furyl]-2-propynamide;
2-methyl-3-[[4-[(4-aminosulfonyl)phenyl]-3-(4-chlorophenyl)-N-hydroxy-N-methyl-2-furyl]-2-propynamide;
2-methyl-3-[[4-[(4-aminosulfonyl)phenyl]-3-(4-fluorophenyl)-N-hydroxy-N-methyl-2-furyl]-2-propynamide;
2-methyl-3-[[5-[(4-aminosulfonyl)phenyl]-N-hydroxy-4-(4-methoxyphenyl)-N-methyl-2-furyl]-2-propynamide;
2-methyl-3-[[4-[(4-aminosulfonyl)phenyl]-5-(3-chloro-4-methoxyphenyl)-N-hydroxy-N-methyl-2-furyl]-2-propynamide;
2-methyl-3-[[5-[(4-aminosulfonyl)phenyl]-4-(3-fluoro-4-methoxyphenyl)-N-hydroxy-N-methyl-2-furyl]-2-propynamide;
2-methyl-3-[[4-[(4-aminosulfonyl)phenyl]-5-(3-chloro-4-fluorophenyl)-N-hydroxy-N-methyl-2-furyl]-2-propynamide;
2-methyl-3-[[4-[(4-methylsulfonyl)phenyl]-N-hydroxy-N-methyl-3-phenyl-2-furyl]-2-propynamide;
2-methyl-3-[[4-(4-chlorophenyl)-N-hydroxy-N-methyl-5-[(4-methylsulfonyl)phenyl]-2-furyl]-2-propynamide;
[4-[(4-aminosulfonyl)phenyl]-5-phenyl-2-oxazolyl]-N-hydroxy-N-methyl-2-benzamide;
[4-[(4-aminosulfonyl)phenyl]-5-(4-chlorophenyl)-2-oxazolyl]-N-hydroxy-N-methyl-2-benzamide;
[5-[(4-aminosulfonyl)phenyl]-4-phenyl-2-oxazolyl]-N-hydroxy-N-methyl-2-benzamide;
[5-[(4-aminosulfonyl)phenyl]-4-(4-chlorophenyl)-2-oxazolyl]-N-hydroxy-N-methyl-2-benzamide;
[5-[(4-aminosulfonyl)phenyl]-3-(4-fluorophenyl)-2-oxazolyl]-N-hydroxy-N-methyl-2-benzamide;
[5-[(4-aminosulfonyl)phenyl]-3-(4-methoxyphenyl)-2-oxazolyl]-N-hydroxy-N-methyl-2-benzamide;
[5-[(4-aminosulfonyl)phenyl]-3-(3-chloro-4-methoxyphenyl)-2-oxazolyl]-N-hydroxy-N-methyl-2-benzamide;
[5-[(4-aminosulfonyl)phenyl]-4-(3-fluoro-4-methoxyphenyl)-2-oxazolyl]-N-hydroxy-N-methyl-2-benzamide;
[5-[(4-aminosulfonyl)phenyl]-4-(3-chloro-4-fluorophenyl)-2-oxazolyl]-N-hydroxy-N-methyl-2-benzamide;
[4-[(4-methylsulfonyl)phenyl]-5-phenyl-2-oxazolyl]-N-hydroxy-N-methyl-2-benzamide;
[5-(4-chlorophenyl)-4-[(4-methylsulfonyl)phenyl]-2-oxazolyl]-N-hydroxy-N-methyl-3-benzamide;
[5-[(4-methylsulfonyl)phenyl]-4-phenyl-2-oxazolyl]-N-hydroxy-N-methyl-3-benzamide;
[4-(4-chlorophenyl)-5-[(4-methylsulfonyl)phenyl]-2-oxazolyl]-N-hydroxy-N-methyl-2-benzamide;
[1-[(4-aminosulfonyl)phenyl]-5-phenyl-1H-pyrazol-3-yl]-N-hydroxy-N-methyl-2-benzamide;
[1-[(4-aminosulfonyl)phenyl]-5-(4-chlorophenyl)-1H-pyrazol-3-yl]-N-hydroxy-N-methyl-2-benzamide;
[3-[(4-aminosulfonyl)phenyl]-4-phenyl-1H-pyrazol-1-yl]-N-hydroxy-N-methyl-2-benzamide;
[3-[(4-aminosulfonyl)phenyl]-4-(4-chlorophenyl)-1H-pyrazol-1-yl]-N-hydroxy-N-methyl-3-benzamide;
[1-[(4-aminosulfonyl)phenyl]-5-(4-fluorophenyl)-1H-pyrazol-3-yl]-N-hydroxy-N-methyl-3-benzamide;
[1-[(4-aminosulfonyl)phenyl]-5-(4-methoxyphenyl)-1H-pyrazol-3-yl]-N-hydroxy-N-methyl-4-benzamide;
[1-[(4-aminosulfonyl)phenyl]-5-(3-chloro-4-methoxyphenyl)-1H-pyrazol-3-yl]-N-hydroxy-N-methyl-2-benzamide;
[1-[(4-aminosulfonyl)phenyl]-5-(3-fluoro-4-methoxyphenyl)-1H-pyrazol-3-yl]-N-hydroxy-N-methyl-2-benzamide;
[1-[(4-aminosulfonyl)phenyl]-5-(3-chloro-4-fluorophenyl)-1H-pyrazol-3-yl]-N-hydroxy-N-methyl-2-benzamide;
[1-[(4-methylsulfonyl)phenyl]-5-phenyl-1H-pyrazol-3-yl]-N-hydroxy-N-methyl-2-benzamide;
[5-(4-chlorophenyl)-1-[(4-methylsulfonyl)phenyl]-1H-pyrazol-3-yl]-N-hydroxy-N-methyl-2-benzamide;
[4-[(4-methylsulfonyl)phenyl]-3-phenyl-1H-pyrazol-1-yl]-N-hydroxy-N-methyl-2-benzamide;
[4-(4-chlorophenyl)-3-[(4-methylsulfonyl)phenyl]-1H-pyrazol-1-yl]-N-hydroxy-N-methyl-4-benzamide;
5-[4-[(4-aminosulfonyl)phenyl]-5-phenyl-2-oxazolyl]-N-hydroxy-N-methyl-1,2,3-triazol-4-ylethanamide;
5-[4-[(4-aminosulfonyl)phenyl]-5-(4-chlorophenyl)-2-oxazolyl]-N-hydroxy-N-methyl-1,2,3-triazol-4-ylethanamide;
5-[5-[(4-aminosulfonyl)phenyl]-4-phenyl-2-oxazolyl]-N-hydroxy-N-methyl-1,2,3-triazol-4-ylethanamide;
5-[5-[(4-aminosulfonyl)phenyl]-4-(4-chlorophenyl)-2-oxazolyl]-N-hydroxy-N-methyl-1,2,3-triazol-4-ylethanamide;

5-[5-[(4-aminosulfonyl)phenyl]-4-(4-fluorophenyl)-2-oxazolyl]-N-hydroxy-N-methyl-1,2,3-triazol-4-ylethanamide;
5-[5-[(4-aminosulfonyl)phenyl]-4-(4-methoxyphenyl)-2-oxazolyl]-N-hydroxy-N-methyl-1,2,3-triazol-4-ylethanamide;
5-[5-[(4-aminosulfonyl)phenyl]-4-(3-chloro-4-methoxyphenyl)-2-oxazolyl]-N-hydroxy-N-methyl-1,2,3-triazol-4-ylethanamide;
5-[5-[(4-aminosulfonyl)phenyl]-4-(3-fluoro-4-methoxyphenyl)-2-oxazolyl]-N-hydroxy-N-methyl-1,2,3-triazol-4-ylethanamide;
5-[5-[(4-aminosulfonyl)phenyl]-4-(3-chloro-4-fluorophenyl)-2-oxazolyl]-N-hydroxy-N-methyl-1,2,3-triazol-4-ylethanamide;
5-[4-[(4-methylsulfonyl)phenyl]-5-cyclohexyl-2-oxazolyl]-N-hydroxy-N-methyl-1,2,3-triazol-4-ylethanamide;
5-[5-(4-chlorophenyl)-4-[(4-methylsulfonyl)phenyl]-2-oxazolyl]-N-hydroxy-N-methyl-1,2,3-triazol-4-ylethanamide;
5-[5-[(4-methylsulfonyl)phenyl]-4-cyclohexenyl-2-oxazolyl]-N-hydroxy-N-methyl-1,2,3-triazol-4-ylethanamide;
5-[4-(4-chlorophenyl)-5-[(4-methylsulfonyl)phenyl]-2-oxazolyl]-N-hydroxy-N-methyl-1,2,3-triazol-4-ylethanamide;
3-[4-(4-aminosulfonyl)phenyl]-5-phenyl-2-oxazolyl)-N-hydroxy-N-methyl-3-cyclohexanamide;
3-[4-[(4-aminosulfonyl)phenyl]-5-(4-chlorophenyl)-2-oxazolyl]-N-hydroxy-N-methyl-3-cyclohexanamide;
3-[5-(4-aminosulfonyl)phenyl]-4-phenyl-2-oxazolyl]-N-hydroxy-N-methyl-3-cyclohexanamide;
4-[5-(4-aminosulfonyl)phenyl]-4-(4-chlorophenyl)-2-oxazolyl]-N-hydroxy-N-methyl-3-cyclohexanamide;
4-[5-[(4-aminosulfonyl)phenyl]-4-(4-fluorophenyl)-2-oxazolyl]-N-hydroxy-N-methyl-3-cyclohexanamide;
4-[5-[(4-aminosulfonyl)phenyl]-4-(4-methoxyphenyl)-2-oxazolyl]-N-hydroxy-N-methyl-3-cyclohexanamide;
4-[5-[(4-aminosulfonyl)phenyl]-4-(3-chloro-4-methoxyphenyl)-2-oxazolyl]-N-hydroxy-N-methyl-3-cyclohexanamide;
4-[5-[(4-aminosulfonyl)phenyl]-4-(3-fluoro-4-methoxyphenyl)-2-oxazolyl]-N-hydroxy-N-methyl-3-cyclohexanamide;
4-[5-[(4-aminosulfonyl)phenyl]-4-(3-chloro-4-fluorophenyl)-2-oxazolyl]-N-hydroxy-N-methyl-3-cyclohexanamide;
4-[5-cyclohexyl-4-[(4-methylsulfonyl)phenyl]-2-oxazolyl]-N-hydroxy-N-methyl-3-cyclohexanamide;
4-[5-(4-chlorophenyl)-4-[(4-methylsulfonyl)phenyl]-2-oxazolyl]-N-hydroxy-N-methyl-3-cyclohexanamide;
3-(4-cyclohexenyl-5-[(4-methylsulfonyl)phenyl]-2-oxazolyl]-N-hydroxy-N-methyl-3-cyclohexanamide;
3-[4-(4-chlorophenyl)-5-[(4-methylsulfonyl)phenyl]-2-oxazolyl]-N-hydroxy-N-methyl-3-cyclohexanamide;
N'-[4-[4 (4-aminosulfonyl)phenyl]-5-phenyl-2-oxazolyl]methyl-N'-hydroxyurea;
N'-[4-[(4-aminosulfonyl)phenyl]-5-(4-chlorophenyl)-2-oxazolyl]methyl-N'-hydroxyurea;
N'-[5-[(4-aminosulfonyl)phenyl]-4-phenyl-2-oxazolyl]methyl-N'-hydroxyurea;
N'-[5-(4-aminosulfonyl)phenyl]-4-(4-chlorophenyl)-2-oxazolyl]methyl-N'-hydroxyurea;
N'-[5-[(4-aminosulfonyl)phenyl]-4-(4-fluorophenyl)-2-oxazolyl]methyl-N'-hydroxyurea;
N'-[5-[(4-aminosulfonyl)phenyl]-4-(4-methoxyphenyl)-2-oxazolyl]methyl-N'-hydroxyurea;
N'-[5-[(4-aminosulfonyl)phenyl]-4-(3-chloro-4-methoxyphenyl)-2-oxazolyl]methyl-N'-hydroxyurea;
N'-[5-[(4-aminosulfonyl)phenyl]-4-(3-fluoro-4-methoxyphenyl)-2-oxazolyl]methyl-N'-hydroxyurea;
N'-[5-[(4-aminosulfonyl)phenyl]-4-(3-chloro-4-fluorophenyl)-2-oxazolyl]methyl-N'-hydroxyurea;
N'-[4-[(4-methylsulfonyl)phenyl]-5-phenyl-2-oxazolyl]methyl-N'-hydroxyurea;
N'-[5-(4-chlorophenyl)-4-[(4-methylsulfonyl)phenyl]-2-oxazolyl]methyl-N'-hydroxyurea;
N'-[5-[(4-methylsulfonyl)phenyl]-4-phenyl-2-oxazolyl]methyl-N'-hydroxyurea;
N'-[4-(4-chlorophenyl)-5-[(4-methylsulfonyl)phenyl]-2-oxazolyl]methyl-N'-hydroxyurea;
N'-[4-[(4-aminosulfonyl)phenyl]-5-phenyl-2-oxazolyl]ethyl-N'-hydroxyurea;
N'-[4-[(4-aminosulfonyl)phenyl]-5-(4-chlorophenyl)-2-oxazolyl]ethyl-N'-hydroxyurea;
N'-[5-[(4-aminosulfonyl)phenyl]-4-phenyl-2-oxazolyl]ethyl-N'-hydroxyurea;
N'-[5-[(4-aminosulfonyl)phenyl]-4-(4-chlorophenyl)-2-oxazolyl]ethyl-N'-hydroxyurea;
N'-[5-[(4-aminosulfonyl)phenyl]-4-(4-fluorophenyl)-2-oxazolyl]ethyl-N'-hydroxyurea;
N'-[5-(4-aminosulfonyl)phenyl]-4-(4-methoxyphenyl)-2-oxazolyl]ethyl-N'-hydroxyurea;
N'-[5-[(4-aminosulfonyl)phenyl]-4-(3-chloro-4-methoxyphenyl)-2-oxazolyl) ethyl-N'-hydroxyurea;
N'-[5-[(4-aminosulfonyl)phenyl]-4-(3-fluoro-4-methoxyphenyl)-2-oxazolyl]ethyl-N'-hydroxyurea;
N'-[5-[(4-aminosulfonyl)phenyl]-4-(3-chloro-4-fluorophenyl)-2-oxazolyl]ethyl-N'-hydroxyurea;
N'-[4-[(4-methylsulfonyl)phenyl]-5-phenyl-2-oxazolyl]ethyl-N'-hydroxyurea;
N'-[5-(4-chlorophenyl)-4-[(4-methylsulfonyl)phenyl]-2-oxazolyl]ethyl-N'-hydroxyurea;
N'-[5-[(4-methylsulfonyl)phenyl]-4-phenyl-2-oxazolyl]ethyl-N'-hydroxyurea;
N'-[4-(4-chlorophenyl)-5-[(4-methylsulfonyl)phenyl]-2-oxazolyl]ethyl-N'-hydroxyurea;
N'-[4-[(4-aminosulfonyl)phenyl]-3-phenyl-5-isoxazolyl]methyl-N'-hydroxyurea;
N'-[4-[(4-aminosulfonyl)phenyl]-3-(4-chlorophenyl)-5-isoxazolyl]methyl-N'-hydroxyurea;
N'-[4-[(4-aminosulfonyl)phenyl]-3-(4-fluorophenyl)-5-isoxazolyl]methyl-N'-hydroxyurea;
N'-14-[(4-aminosulfonyl)phenyl]-3-(4-methoxyphenyl)-5-isoxazolyl]methyl-N'-hydroxyurea;
N'-[4-[(4-aminosulfonyl)phenyl]-3-(3-chloro-4-methoxyphenyl)-5-isoxazolyl]methyl-N'-hydroxyurea;
N'-[4-[(4-aminosulfonyl)phenyl]-3-(3-fluoro-4-methoxyphenyl)-5-isoxazolyl]methyl-N'-hydroxyurea;
N'-[4-[(4-aminosulfonyl)phenyl]-3-(3-chloro-4-fluorophenyl)-5-isoxazolyl]methyl-N'-hydroxyurea;
N'-[4-[(4-methylsulfonyl)phenyl]-3-phenyl-5-isoxazolyl]methyl-N'-hydroxyurea;
N'-[3-(4-chlorophenyl)-4-[(4-methylsulfonyl)phenyl]-5-isoxazolyl]methyl-N'-hydroxyurea;
N'-[4-[(4-aminosulfonyl)phenyl]-3-phenyl-2-thienyl]methyl-N'-hydroxyurea;
N'-[4-[(4-aminosulfonyl)phenyl]-3-(4-chlorophenyl)-2-thienyl]methyl-N'-hydroxyurea;
N'-[4-[(4-aminosulfonyl)phenyl]-3-(4-fluorophenyl)-2-thienyl]methyl-N'-hydroxyurea;
N'-[4-[(4-aminosulfonyl)phenyl)-3-(4-methoxyphenyl)-2-thienyl]methyl-N'-hydroxyurea;
N'-[4-[(4-aminosulfonyl)phenyl]-3-(3-chloro-4-methoxyphenyl)-2-thienyl]methyl-N'-hydroxyurea;

N'-[4-[(4-aminosulfonyl)phenyl]-3-(3-fluoro-4-methoxyphenyl)-2-thienyl]methyl-N'-hydroxyurea;
N'-[4-[(4-aminosulfonyl)phenyl]-3-(3-chloro-4-fluorophenyl)-2-thienyl]methyl-N'-hydroxyurea;
N'-[3-[(4-methylsulfonyl)phenyl]-4-phenyl-5-thienyl]methyl-N'-hydroxyurea;
N'-[4-(4-chlorophenyl)-3-[(4-methylsulfonyl)phenyl]-5-thienyl]methyl-N'-hydroxyurea;
N'-[5-[(4-aminosulfonyl)phenyl]-6-phenyl-3-pyridyl]methyl-N'-hydroxyurea;
N'-[5-[(4-aminosulfonyl)phenyl]-6-(4-chlorophenyl)-3-pyridyl]methyl-N'-hydroxyurea;
N'-[5-[(4-aminosulfonyl)phenyl]-6-(4-fluorophenyl)-3-pyridyl]methyl-N'-hydroxyurea;
N'-[5-[(4-aminosulfonyl)phenyl]-6-(4-methoxyphenyl)-3-pyridyl]methyl-N'-hydroxyurea;
N'-[6-[(4-aminosulfonyl)phenyl]-5-(3-chloro-4-methoxyphenyl)-3-pyridyl]methyl-N'-hydroxyurea;
N'-[6-[(4-aminosulfonyl)phenyl]-5-(3-fluoro-4-methoxyphenyl)-3-pyridyl]methyl-N'-hydroxyurea;
N'-[5-[(4-aminosulfonyl)phenyl]-6-(3-chloro-4-fluorophenyl)-3-pyridyl]methyl-N'-hydroxyurea;
N'-[5-[(4-methylsulfonyl)phenyl]-6-phenyl-3-pyridyl)methyl-N'-hydroxyurea;
N'-[5-(4-chlorophenyl)-6-[(4-methylsulfonyl)phenyl]-3-pyridyl]methyl-N'-hydroxyurea;
N'-[4-[(4-aminosulfonyl)phenyl]-3-phenyl-2-furyl]methyl-N'-hydroxyurea;
N'-[4-[(4-aminosulfonyl)phenyl]-3-(4-chlorophenyl)-2-furyl]methyl-N'-hydroxyurea;
N'-[4-[(4-aminosulfonyl)phenyl]-3-(4-fluorophenyl)-2-furyl]methyl-N'-hydroxyurea;
N'-[5-[(4-aminosulfonyl)phenyl]-4-(4-methoxyphenyl)-2-furyl]methyl-N'-hydroxyurea;
N'-[4-[(4-aminosulfonyl)phenyl]-5-(3-chloro-4-methoxyphenyl)-2-furyl]methyl-N'-hydroxyurea;
N'-[5-[(4-aminosulfonyl)phenyl]-4-(3-fluoro-4-methoxyphenyl)-2-furyl]methyl-N'-hydroxyurea;
N'-[4-[(4-aminosulfonyl)phenyl]-5-(3-chloro-4-fluorophenyl)-2-furyl]methyl-N'-hydroxyurea;
N'-[4-[(4-methylsulfonyl)phenyl]-3-phenyl-2-furyl]methyl-N'-hydroxyurea;
N'-[4-(4-chlorophenyl)-5-[(4-methylsulfonyl)phenyl]-2-furyl]methyl-N'-hydroxyurea;
N'-[4-[(4-aminosulfonyl)phenyl]-5-phenyl-2-oxazolyl]methyl-N'-hydroxyurea;
N'-[4-[(4-aminosulfonyl)phenyl]-5-(4-chlorophenyl)-2-oxazolyl]methyl-N'-hydroxyurea;
N'-[5-[(4-aminosulfonyl)phenyl]-4-phenyl-2-oxazolyl]methyl-N'-hydroxyurea;
N'-[5-[(4-aminosulfonyl)phenyl]-4-(4-chlorophenyl)-2-oxazolyl]methyl-N'-hydroxyurea;
N'-[5-[(4-aminosulfonyl)phenyl]-4-(4-fluorophenyl)-2-oxazolyl]methyl-N'-hydroxyurea;
N'-[5-[(4-aminosulfonyl)phenyl]-4-(4-methoxyphenyl)-2-oxazolyl]methyl-N'-hydroxyurea;
N'-[5-[(4-aminosulfonyl)phenyl]-4-(3-chloro-4-methoxyphenyl)-2-oxazolyl]methyl-N'-hydroxyurea;
N'-[5-[(4-aminosulfonyl)phenyl]-4-(3-fluoro-4-methoxyphenyl)-2-oxazolyl]methyl-N'-hydroxyurea;
N'-[5-[(4-aminosulfonyl)phenyl]-4-(3-chloro-4-fluorophenyl)-2-oxazolyl]methyl-N'-hydroxyurea;
N'-[4-[(4-methylsulfonyl)phenyl]-4-phenyl-2-oxazolyl]methyl-N'-hydroxyurea;
N'-[5-(4-chlorophenyl)-4-[(4-methylsulfonyl)phenyl]-2-oxazolyl]methyl-N'-hydroxyurea;
N'-[5-[(4-methylsulfonyl)phenyl]-4-phenyl-2-oxazolyl]methyl-N'-hydroxyurea;
N'-[4-(4-chlorophenyl)-5-(4-methylsulfonyl)phenyl]-2-oxazolyl]methyl-N'-hydroxyurea;
3-[N'-[1-[4-[(4-aminosulfonyl)phenyl]-5-phenyl-2-oxazolyl]-2-propenyl]-N'-hydroxyurea;
3-[N'-[1-N'-[4-[(4-aminosulfonyl)phenyl]-5-(4-chlorophenyl)-2-oxazolyl]-2-propenyl]-N-hydroxyurea;
3-[N'-[1-[5-[(4-aminosulfonyl)phenyl]-4-phenyl-2-oxazolyl]-2-propenyl]-N'-hydroxyurea;
3-[N'-[1-[5-[(4-aminosulfonyl)phenyl]-4-(4-chlorophenyl)-2-oxazolyl]-2-propenyl]-N'-hydroxyurea;
3-N'-[1-[5-[(4-aminosulfonyl)phenyl]-4-(4-fluorophenyl)-2-oxazolyl]-2-propenyl]-N'-hydroxyurea;
3-[N'-[1-[5-[(4-aminosulfonyl)phenyl]-4-(4-methoxyphenyl)-2-oxazolyl]-2-propenyl]-N'-hydroxyurea;
3-[N'-[1-[5-[(4-aminosulfonyl)phenyl]-4-(3-chloro-4-methoxyphenyl)-2-oxazolyl]-2-propenyl]-N'-hydroxyurea;
3-[N'-[1-[5-[(4-aminosulfonyl)phenyl]-4-(3-fluoro-4-methoxyphenyl)-2-oxazolyl]-2-propenyl]-N'-hydroxyurea;
3-[N'-[1-[5-[(4-aminosulfonyl)phenyl]-4-(3-chloro-4-fluorophenyl)-2-oxazolyl]-2-propenyl]-N'-hydroxyurea;
3-[N'-[1-[4-[(4-methylsulfonyl)phenyl]-5-phenyl-2-oxazolyl]-2-propenyl]-N'-hydroxyurea;
3-[N'-[1-[5-(4-chlorophenyl)-4-[(4-methylsulfonyl)phenyl]-2-oxazolyl]-2-propenyl]-N'-hydroxyurea;
3-[N'-[1-[5-[(4-methylsulfonyl)phenyl]-4-phenyl-2-oxazolyl]-2-propenyl]-N-hydroxyurea;
3-[N'-[1-[4-(4-chlorophenyl)-5-[(4-methylsulfonyl)phenyl]-2-oxazolyl]-2-propenyl]-N'-hydroxyurea;
3-[N'-[1-[1-(4-aminosulfonyl)phenyl]-5-phenyl-1H-pyrazol-3-yl)-2-propenyl]-N'-hydroxyurea;
3-[N'-[1-[1-[(4-aminosulfonyl)phenyl]-5-(4-chlorophenyl)-1H-pyrazol-3-yl]-2-propenyl]-N'-hydroxyurea;
3-[N'-[1-[3-[(4-aminosulfonyl)phenyl]-4-phenyl-1H-pyrazol-1-yl]-2-propenyl]-N'-hydroxyurea;
3-[N'-[1-[3-[(4-aminosulfonyl)phenyl]-4-(4-chlorophenyl)-1H-pyrazol-1-yl]-2-propenyl]-N'-hydroxyurea;
3-[N'-[1-[1-[(4-aminosulfonyl)phenyl]-5-(4-fluorophenyl)-1H-pyrazol-3-yl]-2-propenyl]-N'-hydroxyurea;
3-[N'-[1-[1-[(4-aminosulfonyl)phenyl]-5-(4-methoxyphenyl)-1H-pyrazol-3-yl]-2-propenyl]-N'-hydroxyurea;
3-[N'-[1-[1-[(4-aminosulfonyl)phenyl]-5-(3-chloro-4-methoxyphenyl)-1H-pyrazol-3-yl]-2-propenyl]-N'-hydroxyurea;
3-[N'-[1-[1-[(4-aminosulfonyl)phenyl]-5-(3-fluoro-4-methoxyphenyl)-1H-pyrazol-3-yl]-2-propenyl]-N'-hydroxyurea;
3-[N'-[1-[1-[(4-aminosulfonyl)phenyl]-5-(3-chloro-4-fluorophenyl)-1H-pyrazol-3-yl]-2-propenyl]-N'-hydroxyurea;
3-[N'-[1-[1-[(4-methylsulfonyl)phenyl]-5-phenyl-1H-pyrazol-3-yl]-2-propenyl]-N'-hydroxyurea;
3-[N'-[1-[5-(4-chlorophenyl)-1-[(4-methylsulfonyl)phenyl]-1H-pyrazol-3-yl]-2-propenyl]-N'-hydroxyurea;
3-[N'-[1-[4-[(4-methylsulfonyl)phenyl]-3-phenyl-1H-pyrazol-1-yl]-2-propenyl]-N'-hydroxyurea;
3-[N'-[1-[4-(4-chlorophenyl)-3-[(4-methylsulfonyl)phenyl]-1H-pyrazol-1-yl]-2-propenyl]-N'-hydroxyurea;
3-[N'-[1-[4-[(4-aminosulfonyl)phenyl]-5-phenyl-2-oxazolyl]-2-propynyl]-N'-hydroxyurea;
3-[N'-[1-[4-[(4-aminosulfonyl)phenyl]-5-(4-chlorophenyl)-2-oxazolyl]-2-propynyl]-N'-hydroxyurea;
3-[N'-[1-[5-[(4-aminosulfonyl)phenyl]-4-phenyl-2-oxazolyl]-2-propynyl]-N'-hydroxyurea;

3-[N'-[1-[5-[(4-aminosulfonyl)phenyl]-4-(4-chlorophenyl)-2-oxazolyl]-2-propynyl]-N'-hydroxyurea;
3-[N'-1-[5-[(4-aminosulfonyl)phenyl]-4-(4-fluorophenyl)-2-oxazolyl]-2-propynyl]-N'-hydroxyurea;
3-[N'-[1-[5-[(4-aminosulfonyl)phenyl]-4-(4-methoxyphenyl)-2-oxazolyl]-2-propynyl]-N'-hydroxyurea;
3-[N'-[1-[5-[(4-aminosulfonyl)phenyl]-4-(3-chloro-4-methoxyphenyl)-2-oxazolyl]-2-propynyl]-N'-hydroxyurea;
3-[N'-[1-[5-[(4-aminosulfonyl)phenyl]-4-(3-fluoro-4-methoxyphenyl)-2-oxazolyl]-2-propynyl]-N'-hydroxyurea;
3-[N'-[1-[5-[(4-aminosulfonyl)phenyl]-4-(3-chloro-4-fluorophenyl)-2-oxazolyl]-2-propynyl]-N'-hydroxyurea;
3-[N'-[1-[4-[(4-methylsulfonyl)phenyl]-5-phenyl-2-oxazolyl]-2-propynyl]-N'-hydroxyurea;
3-[N'-[1-[5-(4-chlorophenyl)-4-[(4-methylsulfonyl)phenyl]-2-oxazolyl]-2-propynyl]-N'-hydroxyurea;
3-[N'-[1-[5-[(4-methylsulfonyl)phenyl]-4-phenyl-2-oxazolyl]-2-propynyl]-N'-hydroxyurea;
3-[N'-[1-[4-(4-chlorophenyl)-5-[(4-methylsulfonyl)phenyl]-2-oxazolyl]-2-propynyl]-N'-hydroxyurea;
3-[N'-[1-[1-[(4-aminosulfonyl)phenyl]-5-phenyl-1H-pyrazol-3-yl]-2-propynyl]-N'-hydroxyurea;
3-[N'-[1-[1-[(4-aminosulfonyl)phenyl]-5-(4-chlorophenyl)-1H-pyrazol-3-yl]-2-propynyl]-N'-hydroxyurea;
3-[N'-[1-[3-[(4-aminosulfonyl)phenyl]-4-phenyl-1H-pyrazol-1-yl]-2-propynyl]-N'-hydroxyurea;
3-[N'-[1-[3-[(4-aminosulfonyl)phenyl]-4-(4-chlorophenyl)-1H-pyrazol-1-yl]-2-propynyl]-N'-hydroxyurea;
3-[N'-[1-[1-[(4-aminosulfonyl)phenyl]-5-(4-fluorophenyl)-1H-pyrazol-3-yl]-2-propynyl]-N'-hydroxyurea;
3-[N'-[1-[1-[(4-aminosulfonyl)phenyl]-5-(4-methoxyphenyl)-1H-pyrazol-3-yl]-2-propynyl]-N'-hydroxyurea;
3-[N'-[1-[1-[(4-aminosulfonyl)phenyl]-5-(3-chloro-4-methoxyphenyl)-1H-pyrazol-3-yl]-2-propynyl]-N'-hydroxyurea;
3-[N'-[1-[1-[(4-aminosulfonyl)phenyl]-5-(3-fluoro-4-methoxyphenyl)-1H-pyrazol-3-yl]-2-propynyl]-N'-hydroxyurea;
3-[N'-[1-[1-[(4-aminosulfonyl)phenyl]-5-(3-chloro-4-fluorophenyl)-1H-pyrazol-3-yl]-2-propynyl]-N'-hydroxyurea;
3-[N'-[1-[1-[(4-methylsulfonyl)phenyl]-5-phenyl-1H-pyrazol-3-yl]-2-propynyl]-N'-hydroxyurea;
3-[N'-[1-[5-(4-chlorophenyl)-1-[(4-methylsulfonyl)phenyl]-1H-pyrazol-3-yl]-2-propynyl]-N'-hydroxyurea;
3-[N'-[1-[4-[(4-methylsulfonyl)phenyl]-3-phenyl-1H-pyrazol-1-yl]-2-propynyl]-N'-hydroxyurea;
3-[N'-[1-[4-(4-chlorophenyl)-3-[(4-methylsulfonyl)phenyl]-1H-pyrazol-1-yl]-2-propynyl]-N'-hydroxyurea;
3-[N'-[1-[1-[(4-aminosulfonyl)phenyl]-5-phenyl-1H-pyrazol-3-yl]-1-methyl-2-propynyl]-N'-hydroxyurea;
3-[N'-[1-[1-[(4-aminosulfonyl)phenyl]-5-(4-chlorophenyl)-1H-pyrazol-3-yl]-1-methyl-2-propynyl]-N'-hydroxyurea;
3-[N'-[1-[3-[(4-aminosulfonyl)phenyl]-4-phenyl-1H-pyrazol-1-yl]-1-methyl-2-propynyl]-N'-hydroxyurea;
3-[N'-[1-[3-[(4-aminosulfonyl)phenyl]-4-(4-chlorophenyl)-1H-pyrazol-1-yl]-1-methyl-2-propynyl]-N'-hydroxyurea;
3-[N'-[1-[1-[(4-aminosulfonyl)phenyl]-5-(4-fluorophenyl)-1H-pyrazol-3-yl]-1-methyl-2-propynyl]-N'-hydroxyurea;
3-[N'-1-[1-[(4-aminosulfonyl)phenyl]-5-(4-methoxyphenyl)-1H-pyrazol-3-yl]-1-methyl-2-propynyl]-N'-hydroxyurea;
3-[N'-[1-[1-(4-aminosulfonyl)phenyl]-5-(3-chloro-4-methoxyphenyl)-1H-pyrazol-3-yl]-1-methyl-2-propynyl]-N'-hydroxyurea;
3-[N'-1-1-[(4-aminosulfonyl)phenyl]-5-(3-fluoro-4-methoxyphenyl)-1H-pyrazol-3-yl]-1-methyl-2-propynyl]-N'-hydroxyurea;
3-[N'-[1-[1-(4-aminosulfonyl)phenyl]-5-(3-chloro-4-fluorophenyl)-1H-pyrazol-3-yl]-1-methyl-2-propynyl]-N'-hydroxyurea;
3-[N'-[1-[1-[(4-methylsulfonyl)phenyl]-5-phenyl-1H-pyrazol-3-yl]-1-methyl-2-propynyl]-N'-hydroxyurea;
3-[N'-[1-[5-(4-chlorophenyl)-1-[(4-methylsulfonyl)phenyl]-1H-pyrazol-3-yl]-1-methyl-2-propynyl]-N'-hydroxyurea;
3-[N'-[1-[4-[(4-methylsulfonyl)phenyl]-3-phenyl-1H-pyrazol-1-yl]-1-methyl-2-propynyl]-N'-hydroxyurea;
3-[N'-[1-[4-(4-chlorophenyl)-3-[(4-methylsulfonyl)phenyl]-1H-pyrazol-1-yl]-1-methyl-2-propynyl]-N'-hydroxyurea;
3-[N'-[4-[(4-aminosulfonyl)phenyl]-5-phenyl-2-oxazolyl]-1-methyl-2-propynyl]-N'-hydroxyurea;
3-[N'-[4-[(4-aminosulfonyl)phenyl]-5-(4-chlorophenyl)-2-oxazolyl]-1-methyl-2-propynyl]-N'-hydroxyurea;
3-[N'-[5-[(4-aminosulfonyl)phenyl]-4-phenyl-2-oxazolyl]-1-methyl-2-propynyl]-N'-hydroxyurea;
3-[N'-[5-[(4-aminosulfonyl)phenyl]-4-(4-chlorophenyl)-2-oxazolyl]-1-methyl-2-propynyl]-N'-hydroxyurea;
3-[N'-[5-[(4-aminosulfonyl)phenyl]-4-(4-fluorophenyl)-2-oxazolyl]-1-methyl-2-propynyl]-N'-hydroxyurea;
3-[N'-[5-[(4-aminosulfonyl)phenyl]-4-(4-methoxyphenyl)-2-oxazolyl]-1-methyl-2-propynyl]-N'-hydroxyurea;
3-[N'-[5-[(4-aminosulfonyl)phenyl]-4-(3-chloro-4-methoxyphenyl)-2-oxazolyl]-1-methyl-2-propynyl]-N'-hydroxyurea;
3-[N'-[5-[(4-aminosulfonyl)phenyl]-4-(3-fluoro-4-methoxyphenyl)-2-oxazolyl]-1-methyl-2-propynyl]-N'-hydroxyurea;
3-[N'-[5-[(4-aminosulfonyl)phenyl]-4-(3-chloro-4-fluorophenyl)-2-oxazolyl]-1-methyl-2-propynyl]-N'-hydroxyurea;
3-[N'-[4-[(4-methylsulfonyl)phenyl]-5-phenyl-2-oxazolyl]-1-methyl-2-propynyl]-N'-hydroxyurea;
3-[N'-[5-(4-chlorophenyl)-4-[(4-methylsulfonyl)phenyl]-2-oxazolyl]-1-methyl-2-propynyl]-N'-hydroxyurea;
3-[N'-[5-[(4-methylsulfonyl)phenyl]-4-phenyl-2-oxazolyl]-1-methyl-2-propynyl]-N'-hydroxyurea;
3-[N'-[4-(4-chlorophenyl)-5-[(4-methylsulfonyl)phenyl]-2-oxazolyl]-1-methyl-2-propynyl]-N'-hydroxyurea;
3-[N'-[4-[(4-aminosulfonyl)phenyl]-3-phenyl-5-isoxazolyl]-1-methyl-2-propynyl]-N'-hydroxyurea;
3-[N'-[4-[(4-aminosulfonyl)phenyl]-3-(4-chlorophenyl)-5-isoxazolyl]-1-methyl-2-propynyl]-N'-hydroxyurea;
3-[N'-[4-[(4-aminosulfonyl)phenyl]-3-(4-fluorophenyl)-5-isoxazolyl]-1-methyl-2-propynyl]-N'-hydroxyurea;
3-[N'-[4-[(4-aminosulfonyl)phenyl]-3-(4-methoxyphenyl)-5-isoxazolyl]-1-methyl-2-propynyl]-N'-hydroxyurea;
3-[N'-[4-[(4-aminosulfonyl)phenyl]-3-(3-chloro-4-methoxyphenyl)-5-isoxazolyl]-1-methyl-2-propynyl]-N'-hydroxyurea;
3-[N'-[4-[(4-aminosulfonyl)phenyl]-3-(3-fluoro-4-methoxyphenyl)-5-isoxazolyl]-1-methyl-2-propynyl]-N'-hydroxyurea;
3-[N'-[4-[(4-aminosulfonyl)phenyl]-3-(3-chloro-4-fluorophenyl)-5-isoxazolyl]-1-methyl-2-propynyl]-N'-hydroxyurea;
3-[N'-[4-[(4-methylsulfonyl)phenyl]-3-phenyl-5-isoxazolyl]-1-methyl-2-propynyl]-N'-hydroxyurea;
3-[N'-[3-(4-chlorophenyl)-4-[(4-methylsulfonyl)phenyl]-5-isoxazolyl]-1-methyl-2-propynyl]-N'-hydroxyurea;
3-[N'-[4-[(4-aminosulfonyl)phenyl]-3-phenyl-2-thienyl]-1-methyl-2-propynyl]-N'-hydroxyurea;
3-[N'-[4-[(4-aminosulfonyl)phenyl]-3-(4-chlorophenyl)-2-thienyl]-1-methyl-2-propynyl]-N'-hydroxyurea;

3-[N'-[4-[(4-aminosulfonyl)phenyl]-3-(4-fluorophenyl)-2-thienyl]-1-methyl-2-propynyl]-N'-hydroxyurea;
3-[N'-[4-[(4-aminosulfonyl)phenyl]-3-(4-methoxyphenyl)-2-thienyl]-1-methyl-2-propynyl]-N'-hydroxyurea;
3-[N'-[4-[(4-aminosulfonyl)phenyl]-3-(3-chloro-4-methoxyphenyl)-2-thienyl]-1-methyl-2-propynyl]-N'-hydroxyurea;
3-[N'-[4-[(4-aminosulfonyl)phenyl]-3-(3-fluoro-4-methoxyphenyl)-2-thienyl]-1-methyl-2-propynyl]-N'-hydroxyurea;
3-[N'-[4-[(4-aminosulfonyl)phenyl]-3-(3-chloro-4-fluorophenyl)-2-thienyl]-1-methyl-2-propynyl]-N'-hydroxyurea;
3-[N'-[3-[(4-methylsulfonyl)phenyl]-4-phenyl-5-thienyl]-1-methyl-2-propynyl]-N'-hydroxyurea;
3-[N'-[4-(4-chlorophenyl)-3-[(4-methylsulfonyl)phenyl]-5-thienyl]-1-methyl-2-propynyl]-N'-hydroxyurea;
3-[N'-[5-[(4-aminosulfonyl)phenyl]-6-phenyl-3-pyridyl]-1-methyl-2-propynyl]-N'-hydroxyurea;
3-[N'-[5-[(4-aminosulfonyl)phenyl]-6-(4-chlorophenyl)-3-pyridyl]-1-methyl-2-propynyl]-N'-hydroxyurea;
3-[N'-[5-[(4-aminosulfonyl)phenyl]-6-(4-fluorophenyl)-3-pyridyl]-1-methyl-2-propynyl]-N'-hydroxyurea;
3-[N'-(5-[(4-aminosulfonyl)phenyl]-6-(4-methoxyphenyl)-3-pyridyl]-1-methyl-2-propynyl]-N'-hydroxyurea;
3-[N'-[6-[(4-aminosulfonyl)phenyl]-5-(3-chloro-4-methoxyphenyl)-3-pyridyl]-1-methyl-2-propynyl]-N'-hydroxyurea;
3-[N'-[6-[(4-aminosulfonyl)phenyl]-5-(3-fluoro-4-methoxyphenyl)-3-pyridyl]-1-methyl-2-propynyl]-N'-hydroxyurea;
3-[N-[5-[(4-aminosulfonyl)phenyl]-6-(3-chloro-4-fluorophenyl)-3-pyridyl]-1-methyl-2-propynyl]-N'-hydroxyurea;
3-[N'-[5-[(4-methylsulfonyl)phenyl]-6-phenyl-3-pyridyl]-1-methyl-2-propynyl]-N'-hydroxyurea;
3-[N'-[5-(4-chlorophenyl)-6-[(4-methylsulfonyl)phenyl]-3-pyridyl]-1-methyl-2-propynyl]-N-hydroxyurea;
3-[N'-[4-[(4-aminosulfonyl)phenyl]-3-phenyl-2-furyl]-1-methyl-2-propynyl]-N'-hydroxyurea;
3-[N'-[4-[(4-aminosulfonyl)phenyl]-3-(4-chlorophenyl)-2-furyl]-1-methyl-2-propynyl]-N'-hydroxyurea;
3-[N'-[4-[(4-aminosulfonyl)phenyl]-3-(4-fluorophenyl)-2-furyl]-1-methyl-2-propynyl]-N'-hydroxyurea;
3-[N'-[5-[(4-aminosulfonyl)phenyl]-4-(4-methoxyphenyl)-2-furyl]-1-methyl-2-propynyl]-N'-hydroxyurea;
3-[N'-[4-[(4-aminosulfonyl)phenyl)-5-(3-chloro-4-methoxyphenyl)-2-furyl]-1-methyl-2-propynyl]-N'-hydroxyurea;
3-[N'-[5-[(4-aminosulfonyl)phenyl]-4-(3-fluoro-4-methoxyphenyl)-2-furyl]-1-methyl-2-propynyl]-N'-hydroxyurea;
3-[N'-[4-[(4-aminosulfonyl)phenyl]-5-(3-chloro-4-fluorophenyl)-2-furyl]-1-methyl-2-propynyl]-N'-hydroxyurea;
3-[N'-[4-[(4-methylsulfonyl)phenyl]-3-phenyl-2-furyl]-1-methyl-2-propynyl]-N'-hydroxyurea;
3-[N'-[4-(4-chlorophenyl)-5-[(4-methylsulfonyl)phenyl]-2-furyl]-1-methyl-2-propynyl]-N'-hydroxyurea;
N'-3-[4-[(4-aminosulfonyl)phenyl]-5-phenyl-2-oxazolyl]phenyl]-N'-hydroxyurea;
N'-[3-[4-[(4-aminosulfonyl)phenyl]-5-(4-chlorophenyl)-2-oxazolyl]phenyl]-N'-hydroxyurea;
N'-[3-[5-[(4-aminosulfonyl)phenyl]-4-phenyl-2-oxazolyl]phenyl]-N'-hydroxyurea;
N'-[4-[5-[(4-aminosulfonyl)phenyl]-4-(4-chlorophenyl)-2-oxazolyl]phenyl]-N'-hydroxyurea;
N'-[4-[5-[(4-aminosulfonyl)phenyl]-4-(4-fluorophenyl)-2-oxazolyl]phenyl]-N'-hydroxyurea;
N'-[4-[5-[(4-aminosulfonyl)phenyl]-4-(4-methoxyphenyl)-2-oxazolyl]phenyl]-N'-hydroxyurea;
N'-[4-[5-[(4-aminosulfonyl)phenyl]-4-(3-chloro-4-methoxyphenyl)-2-oxazolyl]phenyl]-N'-hydroxyurea;
N'-[4-[5-[(4-aminosulfonyl)phenyl]-4-(3-fluoro-4-methoxyphenyl)-2-oxazolyl]phenyl]-N'-hydroxyurea;
N'-[4-[5-[(4-aminosulfonyl)phenyl]-4-(3-chloro-4-fluorophenyl)-2-oxazolyl]phenyl]-N'-hydroxyurea;
N'-[4-[4-[(4-methylsulfonyl)phenyl]-5-phenyl-2-oxazolyl]phenyl]-N'-hydroxyurea;
N'-[4-[5-(4-chlorophenyl)-4-[(4-methylsulfonyl)phenyl]-2-oxazolyl]phenyl]-N'-hydroxyurea;
N'-[3-[5-[(4-methylsulfonyl)phenyl]-4-phenyl-2-oxazolyl]phenyl]-N'-hydroxyurea;
N'-[3-[4-(4-chlorophenyl)-5-[(4-methylsulfonyl)phenyl]-2-oxazolyl]phenyl]-N'-hydroxyurea;
N'-[3-[1-[(4-aminosulfonyl)phenyl]-5-phenyl-1H-pyrazol-3-yl]phenyl]-N'-hydroxyurea;
N'-[2-[1-[(4-aminosulfonyl)phenyl]-5-(4-chlorophenyl)-1H-pyrazol-3-yl]phenyl]-N'-hydroxyurea;
N'-[2-[1-[(4-aminosulfonyl)phenyl]-5-(4-fluorophenyl)-1H-pyrazol-3-yl]phenyl]-N'-hydroxyurea;
N'-[4-[1-[(4-aminosulfonyl)phenyl]-5-(4-methoxyphenyl)-1H-pyrazol-3-yl]phenyl]-N'-hydroxyurea;
N'-[4-[1-[(4-aminosulfonyl)phenyl-5-(3-chloro-4-methoxyphenyl)-1H-pyrazol-3-yl]phenyl]-N'-hydroxyurea;
N'-[3-[1-[(4-aminosulfonyl)phenyl-5-(3-fluoro-4-methoxyphenyl)-1H-pyrazol-3-yl]phenyl]-N'-hydroxyurea;
N'-[4-[1-[(4-aminosulfonyl)phenyl]-5-(3-chloro-4-fluorophenyl)-1H-pyrazol-3-yl]phenyl]-N'-hydroxyurea;
N'-[4-[1-[(4-methylsulfonyl)phenyl]-5-phenyl-1H-pyrazol-3-yl]phenyl]-N'-hydroxyurea;
N'-[4-[5-(4-chlorophenyl)-1-[(4-methylsulfonyl)phenyl]-1H-pyrazol-3-yl]phenyl]-N'-hydroxyurea;
N'-[3-[4-[(4-methylsulfonyl)phenyl]-3-phenyl-1H-pyrazol-1-yl]phenyl]-N'-hydroxyurea;
N'-[3-[4-(4-chlorophenyl)-3-[(4-methylsulfonyl)phenyl]-1H-pyrazol-1-yl]phenyl]-N'-hydroxyurea;
N'-5-[4-[(4-aminosulfonyl)phenyl]-5-phenyl-2-oxazolyl]1,2,3-triazol-4-ylmethyl]-N'-hydroxyurea;
N'-[5-[4-[(4-aminosulfonyl)phenyl]-5-(4-chlorophenyl)-2-oxazolyl]1,2,3-triazol-4-ylmethyl]-N'-hydroxyurea;
N'-[5-[5-[(4-aminosulfonyl)phenyl]-4-phenyl-2-oxazolyl]1,2,3-triazol-4-ylmethyl]-N'-hydroxyurea;
N'-[5-[5-[(4-aminosulfonyl)phenyl]-4-(4-chlorophenyl)-2-oxazolyl]1,2,3-triazol-4-ylmethyl]-N'-hydroxyurea;
N'-[5-[5-[(4-aminosulfonyl)phenyl]-4-(4-fluorophenyl)-2-oxazolyl]1,2,3-triazol-4-ylmethyl]-N'-hydroxyurea;
N'-[5-[5-[(4-aminosulfonyl)phenyl]-4-(4-methoxyphenyl)-2-oxazolyl]1,2,3-triazol-4-ylmethyl]-N'-hydroxyurea;
N'-[5-[5-[(4-aminosulfonyl)phenyl]-4-(3-chloro-4-methoxyphenyl)-2-oxazolyl]1,2,3-triazol-4-ylmethyl]-N'-hydroxyurea;
N'-[5-[5-[(4-aminosulfonyl)phenyl]-4-(3-fluoro-4-methoxyphenyl)-2-oxazolyl]1,2,3-triazol-4-ylmethyl]-N'-hydroxyurea;
N'-[5-[5-[(4-aminosulfonyl)phenyl]-4-(3-chloro-4-fluorophenyl)-2-oxazolyl]1,2,3-triazol-4-ylmethyl]-N'-hydroxyurea;
N'-[5-[4-[(4-methylsulfonyl)phenyl]-5-cyclohexyl-2-oxazolyl]1,2,3-triazol-4-ylmethyl]-N'-hydroxyurea;
N'-[5-[5-(4-chlorophenyl)-4-[(4-methylsulfonyl)phenyl]-2-oxazolyl]1,2,3-triazol-4-ylmethyl]-N'-hydroxyurea;

N'-[5-[5-[(4-methylsulfonyl)phenyl]-4-cyclohexenyl-2-oxazolyl]1,2,3-triazol-4-ylmethyl]-N'-hydroxyurea;
N'-[5-[4-(4-chlorophenyl)-5-[(4-methylsulfonyl)phenyl]-2-oxazolyl]1,2,3-triazol-4-ylmethyl]-N'-hydroxyurea;
N'-[3-[4-[(4-aminosulfonyl)phenyl]-5-phenyl-2-oxazolyl]cyclohexyl]-N'-hydroxyurea;
N'-[3-[4-[(4-aminosulfonyl)phenyl]-5-(4-chlorophenyl)-2-oxazolyl]cyclohexyl]-N'-hydroxyurea;
N'-[3-[5-[(4-aminosulfonyl)phenyl]-4-phenyl-2-oxazolyl]cyclohexyl]-N'-hydroxyurea;
N'-[4-[5-[(4-aminosulfonyl)phenyl]-4-(4-chlorophenyl)-2-oxazolyl]cyclohexyl]-N'-hydroxyurea;
N'-[4-[5-[(4-aminosulfonyl)phenyl]-4-(4-fluorophenyl)-2-oxazolyl]cyclohexyl]-N'-hydroxyurea;
N'-[4-[5-[(4-aminosulfonyl)phenyl]-4-(4-methoxyphenyl)-2-oxazolyl]cyclohexyl]-N'-hydroxyurea;
N'-[4-[5-[(4-aminosulfonyl)phenyl]-4-(3-chloro-4-methoxyphenyl)-2-oxazolyl]cyclohexyl]-N'-hydroxyurea;
N'-[4-[5-[(4-aminosulfonyl)phenyl]-4-(3-fluoro-4-methoxyphenyl)-2-oxazolyl]cyclohexyl]-N'-hydroxyurea;
N'-[4-[5-[(4-aminosulfonyl)phenyl]-4-(3-chloro-4-fluorophenyl)-2-oxazolyl]cyclohexyl]-N'-hydroxyurea;
N'-[4-[4-[(4-methylsulfonyl)phenyl]-5-cyclohexyl-2-oxazolyl]cyclohexyl]-N'-hydroxyurea;
N'-[4-[5-(4-chlorophenyl)-4-[(4-methylsulfonyl)phenyl]-2-oxazolyl]cyclohexyl]-N'-hydroxyurea;
N'-[3-[5-[(4-methylsulfonyl)phenyl]-4-cyclohexenyl-2-oxazolyl]cyclohexyl]-N'-hydroxyurea;
N'-[3-[4-(4-chlorophenyl)-5-[(4-methylsulfonyl)phenyl]-2-oxazolyl]cyclohexyl]-N'-hydroxyurea;
N'-[[1-[(4-aminosulfonyl)phenyl]-5-phenyl-1H-pyrazol-3-yl]methyl]-N'-hydroxyurea;
N'-[[1-[(4-aminosulfonyl)phenyl]-5-(4-fluorophenyl)-1H-pyrazol-3-yl]methyl]-N'-hydroxyurea;
N'-[[1-[(4-aminosulfonyl)phenyl]-5-(4-methoxyphenyl)-1H-pyrazol-3-yl]methyl]-N'-hydroxyurea;
N'-[[1-[(4-aminosulfonyl)phenyl]-5-(3-chloro-4-methoxyphenyl)-1H-pyrazol-3-yl]methyl]-N'-hydroxyurea;
N'-[[1-[(4-aminosulfonyl)phenyl]-5-(3-fluoro-4-methoxyphenyl)-1H-pyrazol-3-yl]methyl]-N'-hydroxyurea;
N'-[[1-[(4-aminosulfonyl)phenyl]-5-(3-chloro-4-fluorophenyl)-1H-pyrazol-3-yl]methyl-N'-hydroxyurea;
N'-[[1-[4-(aminosulfonyl)phenyl]-5-(4-methylphenyl)-1H-pyrazol-3-yl]methyl]-N'-hydroxyurea;
N'-[[1-[4-(aminosulfonyl)phenyl]-5-(4-chlorophenyl)-1H-pyrazol-3-yl]ethyl]-N'-hydroxyurea;
N'-[4-[1-[4-(aminosulfonyl)phenyl]-5-(4-methyl-3-chlorophenyl-1H-pyrazol-3-yl]phenyl]-N'-hydroxyurea;
N'-[3-[1-[4-(aminosulfonyl)phenyl]5-(4-methylphenyl)-1H-pyrazol-3-yl]phenyl]-N'-hydroxyurea;
N'-[5-[1-[4-(aminosulfonyl)phenyl]-5-(4-3-chlorophenyl)-1H-pyrazol-3-yl]-2-thienyl]-N'-hydroxyurea;
N'-[[1-[4-(aminosulfonyl)phenyl]-5-(4-chlorophenyl)-1H-pyrazol-3-yl]methyl]-N'-hydroxyurea; and
4-(4-fluorophenyl)-N-hydroxy-N-methyl-5-[(4-methylsulfonyl)phenyl]-2-oxazolepropanamide.

The term "hydrido" denotes a single hydrogen atom (H). This hydrido radical may be attached, for example, to an oxygen atom to form a hydroxyl radical or two hydrido radicals may be attached to a carbon atom to form a methylene (—CH$_2$—) radical. Where used, either alone or within other terms such as "haloalkyl", "alkylsulfonyl", "alkoxyalkyl", "aminoalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "alkenyl" embraces linear or branched radicals having at least one carbon-carbon double bond of two to about twenty carbon atoms or, preferably, one to about twelve carbon atoms. More preferred alkenyl radicals are "lower alkenyl" radicals having two to about six carbon atoms. Examples of alkenyl radicals include ethenyl, propenyl, allyl, propenyl, butenyl and 4-methylbutenyl. The term "alkynyl", denotes linear or branched radicals having two to about twenty carbon atoms or, preferably, two to about twelve carbon atoms. More preferred alkynyl radicals are "lower alkynyl" radicals having two to about ten carbon atoms. Most preferred are lower alkynyl radicals having two to about six carbon atoms. Examples of such radicals include propynyl, propargyl, butynyl, and the like. The terms "alkenyl", and "lower alkenyl" embrace radicals having "cis" and "trans" orientations, or alternatively, "E" and "Z" orientations. The term "cycloalkyl" embraces saturated carbocyclic radicals having three to twelve carbon atoms. More preferred cycloalkyl radicals are "lower cycloalkyl" radicals having four to about eight carbon atoms. Examples of such radicals include cyclopropyl, cyclobutyl, cyclopentyl and cyclohexyl. The term "cycloalkenyl" embraces partially unsaturated carbocyclic radicals having three to twelve carbon atoms. More preferred cycloalkenyl radicals are "lower cycloalkenyl" radicals having four to about eight carbon atoms. Examples of such radicals include cyclobutenyl, cyclopentenyl and cyclohexenyl. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl", embraces radicals having 1–6 carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "cyanoalkyl" embraces linear or branched alkyl radicals having one to about ten carbon atoms any one of which may be substituted with one or more cyano radicals. More preferred cyanoalkyl radicals are "lower cyanoalkyl" radicals having one to six carbon atoms and one or more cyano radicals. Examples of such radicals include cyanomethyl, cyanoethyl, cyanopropyl, cyanobutyl and cyanohexyl. The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. The terms "alkoxyl" and "alkoxyalkyl" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The term "alkoxyalkyl" embraces alkyl radicals having one or more alkoxy radicals attached to the alkyl radical, that is, to form monoalkoxyalkyl and dialkoxyalkyl radicals. The "alkoxy" radicals may be further substituted with one or more halo atoms, such as fluoro, chloro or bromo, to provide haloalkoxy radicals. More preferred haloalkoxy radicals are "lower haloalkoxyl" radicals having one to six carbon atoms and one or more halo radicals. Examples of such radicals include fluoromethoxy, chloromethoxy, trifluoromethoxy, trifluoroethoxy, fluoroethoxy and fluoropropoxy. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. Aryl moieties may also be substituted at a substitutable position with one or more substituents selected independently from alkyl, alkoxyalkyl, alkylaminoalkyl, carboxyalkyl, alkoxycarbonylalkyl, aminocarbonylalkyl, alkoxy, aralkoxy, amino, halo, nitro, alkylamino, acyl, cyano, carboxy, aminocarbonyl, alkoxycarbonyl and aralkoxycarbonyl. The terms "heterocyclyl" and "heterocycle" embrace saturated, partially unsaturated and unsaturated heteroatom-containing ring-shaped radicals, where the heteroatoms may be selected from nitrogen, sulfur and oxygen. Examples of saturated heterocyclo radicals include saturated 3 to 6-membered heteromonocylic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclo radicals include dihydrothiophene, dihydropyran, dihydrofuran and dihydrothiazole. The term "heteroaryl" embraces unsaturated heterocyclo radicals. Examples of unsaturated heterocyclo radicals, also termed "heteroaryl" radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclo group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclo group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclo group containing 1 to 2 sulfur atoms and 1 to 3 nitrogen atoms (e.g., benzothiazolyl, benzothiadiazolyl, etc.) and the like. The term also embraces radicals where heterocyclo radicals are fused with aryl radicals. Examples of such fused bicyclic radicals include benzofuran, benzothiophene, and the like. Said "heterocyclo group" may also be substituted at a substitutable position with one or more substituents selected independently from alkyl, alkylaminoalkyl, carboxyalkyl, alkoxycarbonylalkyl, aminocarbonylalkyl, hydroxyl, alkoxy, aralkoxy, alkylaminoalkoxy, amino, halo, nitro, alkylamino, acyl, cyano, carboxy, aminocarbonyl, alkoxycarbonyl and aralkoxycarbonyl. The term "alkylthio" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio. The term "alkylsulfinyl" embraces radicals containing a linear or branched alkyl radical, of one to ten carbon atoms, attached to a divalent —S(=O)— radical. More preferred alkylsulfinyl radicals are "lower alkylsufinyl" radicals having alkyl radicals of one to six carbon atoms. Examples of such lower alkylsulfinyl radicals include methylsulfinyl, ethylsulfinyl, butylsulfinyl and hexylsulfinyl. The term "sulfonyl", whether used alone or linked to other terms such as alkylsulfonyl, denotes respectively divalent radicals —SO$_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The "alkylsulfonyl" radicals may be further substituted with one or more halo atoms, such as fluoro, chloro or bromo, to provide haloalkylsulfonyl radicals. The terms "sulfamyl", "aminosulfonyl" and "sulfonamidyl" denote NH$_2$O$_2$S—. The term "aralkyl" embraces aryl-substituted alkyl radicals. Preferred aralkyl radicals are "lower aralkyl" radicals where the alkyl radicals are of 1–6 carbons. Examples of such lower aralkyl radiclas include benzyl, diphenylmethyl, triphenylmethyl, phenylethyl, and diphenylethyl. The aryl in said aralkyl may be additionally substituted with halo, alkyl, alkoxy, halkoalkyl and haloalkoxy. The terms benzyl and phenylmethyl are interchangeable. The term "cycloalkylalkyl" embraces cycloalkyl-substituted alkyl radicals. Preferred cycloalkylalkyl radicals are "lower cycloalkylalkyl" radicals where the alkyl radicals are of 1–6 carbons. Examples of such radicals include cyclohexylmethyl, cyclopentylmethyl, cyclobutylmethyl, cyclohexylethyl, and cyclopentylpropyl. The term "heterocycloalkyl" embraces heterocyclo-substituted alkyl radicals. Preferred heterocycloalkyl radicals are "lower heterocycloalkyl" radicals where the alkyl radicals are of 1–6 carbons and the heterocyclo radicals have 5- or 6-members. Examples of such radicals include triazolylmethyl, triazolylethyl, thienylmethyl, furylethyl, and piperidinomethyl. The heterocyclo in said heterocycloalkyl may be additionally substituted with halo, alkyl, alkoxy, halkoalkyl and haloalkoxy. The term "acyl" denotes a radical provided by the residue after removal of hydroxyl from an organic acid. Examples of such acyl radicals include alkanoyl and aroyl radicals. The alkanoyl radicals may be substituted or unsubstituted, such as formyl, acetyl, propionyl (propanoyl), butanoyl (butyryl), isobutanoyl (isobutyryl), valeryl (pentanoyl), isovaleryl, pivaloyl, hexanoyl or the like. The terms "carboxy" or "carboxyl", whether used alone or with other terms, such as "carboxyalkyl", denotes —CO₂H. The terms "carboxyalkyl" embrace radicals having a carboxy radical as defined above, attached to an alkyl radical. More preferred carboxyalkyl radicals are "lower carboxyalkyl" radicals having alkyl portions of 1–6 carbons. The term "carbonyl", whether used alone or with other terms, such as "alkoxycarbonyl", denotes —(C=O)—. The term "alkoxycarbonyl" means a radical containing an alkoxy radical, as defined above, attached via an oxygen atom to a carbonyl radical. Examples of such "alkoxycarbonyl" ester radicals include substituted or unsubstituted methoxycarbonyl, ethoxycarbonyl, propoxycarbonyl, butoxycarbonyl and hexyloxycarbonyl. The terms "alkylcarbonyl", "arylcarbonyl" and "aralkylcarbonyl" include radicals having alkyl, aryl and aralkyl radicals, as defined above, attached via an oxygen atom to a carbonyl radical. Examples of such radicals include substituted or unsubstituted methylcarbonyl, ethylcarbonyl, phenylcarbonyl and benzylcarbonyl. The term "aminoalkyl", embraces alkyl radicals substituted with amino radicals. More preferred are "lower aminoalkyl" radicals. Examples of such radicals include aminomethyl, aminoethyl, and the like. The term "alkylamino" denotes amino groups which have been substituted with one or two alkyl radicals. More preferred are "lower N-alkylamino" and "lower N,N-dialkylamino". Examples of such radicals include N-methylamino, N-ethylamino, N,N-dimethylamino, N,N-diethylamino and the like. The term "arylamino" denotes amino groups which have been substituted with one or more aryl radicals. Examples of such radicals include N-phenylamino and N-naphthylamino. The "arylamino" radicals may be further substituted on the aryl ring portion of the radical. The term "alkylaminoalkyl" denotes aminoalkyl groups which have been substituted with one or two alkyl radicals, as defined above. More preferred are "lower N-alkylaminoalkyl" and "lower N,N-dialkylaminoalkyl", where lower alkyl is defined above. Examples of such radicals include N-methylaminoethyl, N-ethylaminopropyl, N,N-dimethylaminoethyl, N,N-diethylaminomethyl, and the like. The term "arylaminoalkyl" denotes aminoalkyl groups which have been substituted with one or more aryl radicals, as defined above. More preferred is "lower N-arylaminoalkyl", where lower aminoalkyl is defined above. Examples of such radicals include N-phenylaminoethyl and N-phenylaminopropyl. The "arylaminoalkyl" radicals may be further substituted on the aryl ring portion of the radical. The term "aminocarbonyl" denotes an amide group of the formula —C(=O)NH₂.

When the above radicals are included as linker moiety "Y" in Formulas I–III, such radicals are divalent radicals. For terms such as aralkyl, and heterocycloalkyl, the moiety may be linked to "A" and "R³" through a divalent alkyl radical, or through the alkyl radical at one end and the aryl or heteroaryl portion at the other. The use of heterocyclo and aryl moieties includes divalent attachment at substitutable sites.

The present invention comprises a pharmaceutical composition comprising a therapeutically-effective amount of a compound of Formulas I–III in association with at least one pharmaceutically-acceptable carrier, adjuvant or diluent.

The present invention also comprises a method of treating inflammation or inflammation-associated disorders in a subject, the method comprising treating the subject having or susceptible to such inflammation or disorder, with a therapeutically-effective amount of a compound of Formulas I–III. The method includes prophylactic or chronic treatment, especially in the case of arthritis and other inflammatory conditions which can lead to deterioration in the joints.

Also included in the family of compounds of Formula I are the stereoisomers and tautomers thereof. Compounds of the present invention can possess one or more asymmetric carbon atoms and are thus capable of existing in the form of optical isomers as well as in the form of racemic or nonracemic mixtures thereof. Accordingly, some of the compounds of this invention may be present in racemic mixtures which are also included in this invention. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting an amine functionality of precursors to compounds of Formula I with an optically pure acid in an activated form or an optically pure isocyanate. Alternatively, diastereomeric derivatives can be prepared by reacting a carboxyl functionality of precursors to compounds of Formula I with an optically pure amine base. The synthesized diastereoisomers can be separated by conventional means such as chromatography, distillation, crystallization or sublimation, and then hydrolyzed to deliver the enantiomerically pure compound. The optically active compounds of Formula I can likewise be obtained by utilizing optically active starting materials. These isomers may be in the form of a free acid, a free base, an ester or a salt.

Also included in the family of compounds of Formula I are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclo, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, β-hydroxybutyric, salicylic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

General Synthetic Procedures

The compounds of the invention can be synthesized according to the following procedures of Schemes I–XXIV, wherein the $R^1$–$R^6$ substituents are as defined for Formula I–III, above, except where further noted.

Scheme I

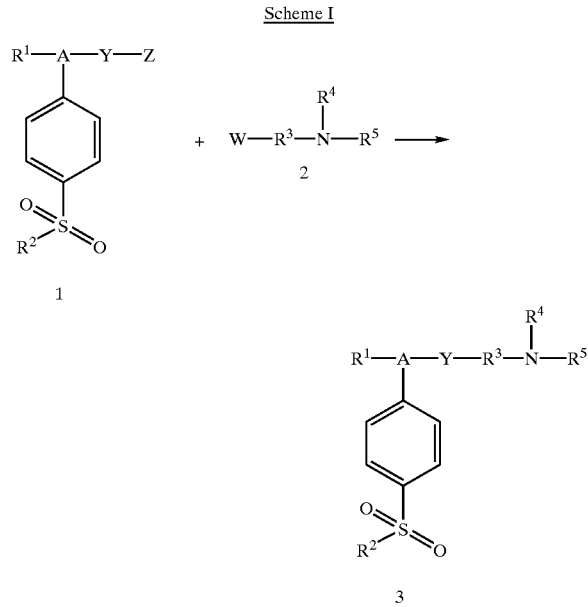

Synthetic Scheme I shows the preparation of amide derivatives 3, where one of Z or W is a leaving group. A substituted hydroxylamine or equivalent 2, is dissolved in anhydrous solvent such as THF or methylene chloride. A solution of sulfonylphenyl derivative 1 in anhydrous DMF is added and stirred at about 0° C. to provide the sulfonylphenyl amide derivatives 3. In addition, hydroxydithiocarbamates can be prepared by the methods described in U.S. Pat. No. 5,298,521, and N-hydroxyamides can be prepared by the procedures described in U.S. Pat. No. 5,051,518, both of which are incorporated by reference.

Scheme II

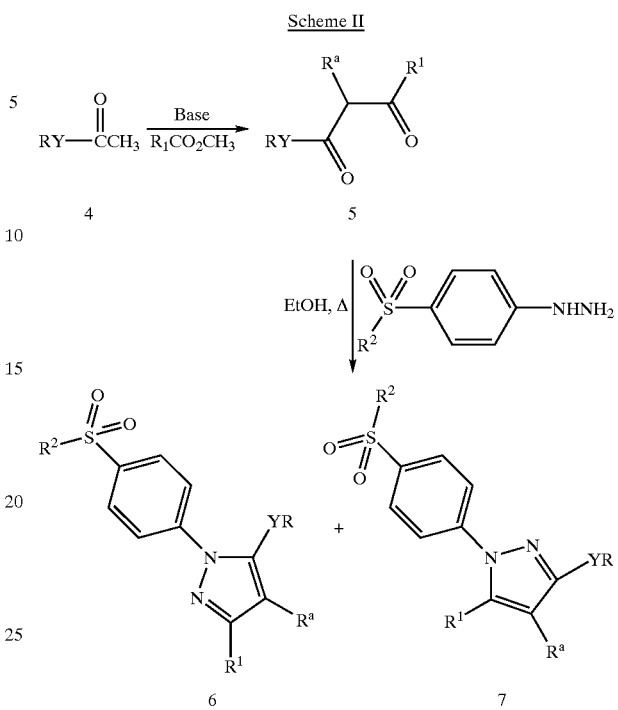

Synthetic Scheme II shows the preparation of pyrazole compounds embraced by Formula I where R is Z, (as defined in Scheme I) and $R^a$ is a radical defined above for the substituents optionally substituted on A. In step 1, ketone 4 is treated with a base, preferably NaOMe or NaH, and an ester, or ester equivalent, to form the intermediate diketone 5 (in the enol form) which is used without further purification. In step 2, diketone 5 in an anhydrous protic solvent, such as absolute ethanol or acetic acid, is treated with the hydrochloride salt or the free base of a substituted hydrazine at reflux to afford a mixture of pyrazoles 6 and 7. Recrystallization from diethyl ether/hexane or chromatography affords 6 usually as a solid. Similar pyrazoles can be prepared by methods described in U.S. Pat. Nos. 4,146,721, 5,051,518, 5,134,142 and 4,914,121 which are incorporated by reference.

Scheme III

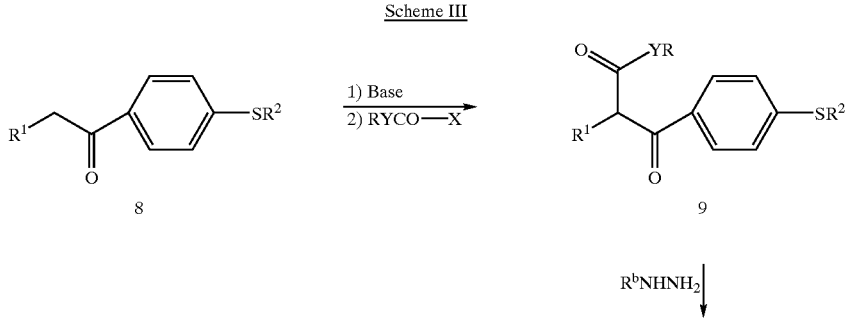

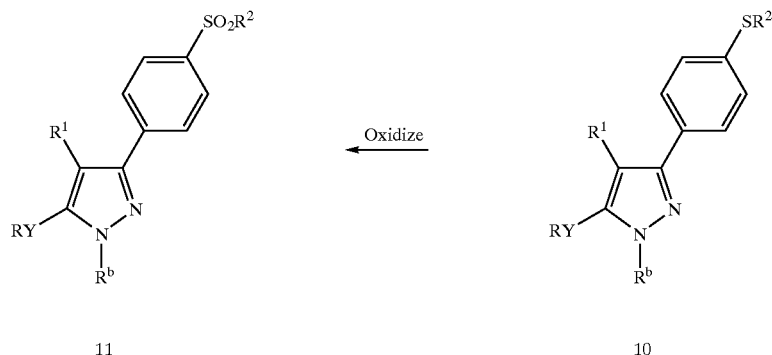

Scheme III shows the four step procedure for forming pyrazoles 11 of the present invention (where $R^b$ is alkyl) from ketones 8. In step 1, ketone 8 is reacted with a base, such as lithium bis(trimethylsilyl)amide or lithium diisopropylamide (LDA) to form the anion. In step 2, the anion is reacted with an acetylating reagent to provide diketone 9. In step 3, the reaction of diketone 9 with hydrazine or a substituted hydrazine, gives pyrazole 10. In step 4, the pyrazole 10 is oxidized with an oxidizing reagent, such as Oxone® (potassium peroxymonosulfate), 3-chloroperbenzoic acid (MCPBA) or hydrogen peroxide, to give a mixture of the desired 3-(alkylsulfonyl)phenyl-pyrazole 11 and the 5-(alkylsulfonyl)phenyl-pyrazole isomer. The desired pyrazole 11, usually a white or pale yellow solid, is obtained in pure form either by chromatography or recrystallization.

Alternatively, diketone 9 can be formed from ketone 8 by treatment with a base, such as sodium hydride, in a solvent, such as dimethylformamide, and further reacting with a nitrile to form an aminoketone. Treatment of the aminoketone with acid forms the diketone 9. Similar pyrazoles can be prepared by methods described in U.S. Pat. No. 3,984,431 which is incorporated by reference.

Scheme IV

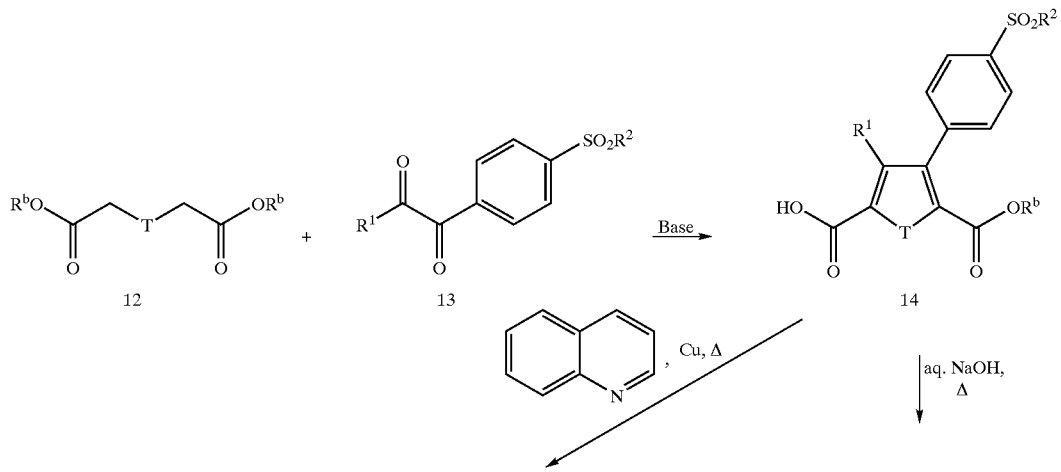

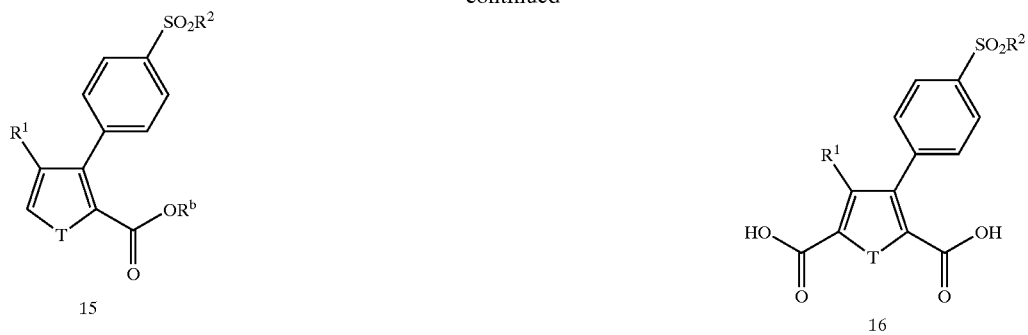

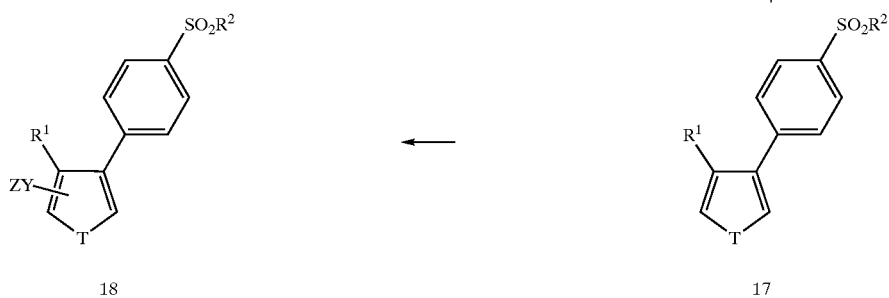

Diaryl/heteroaryl thiophenes (where T is S, and $R^b$ is alkyl) can be prepared by the methods described in U.S. Pat. Nos. 4,427,693, 4,302,461, 4,381,311, 4,590,205, and 4,820,827, and PCT documents WO 95/00501 and WO94/15932, which are incorporated by reference. Similar pyrroles (where T is N), furanones and furans (where T is O) can be prepared by methods described in PCT documents WO 95/00501 and WO94/15932.

Scheme V

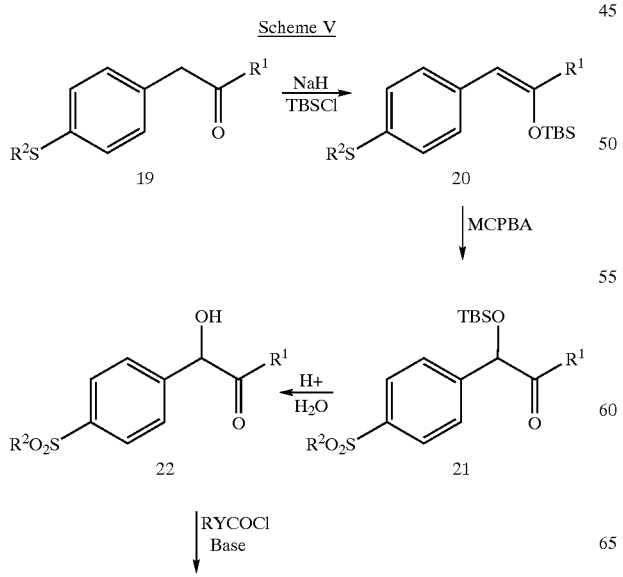

-continued

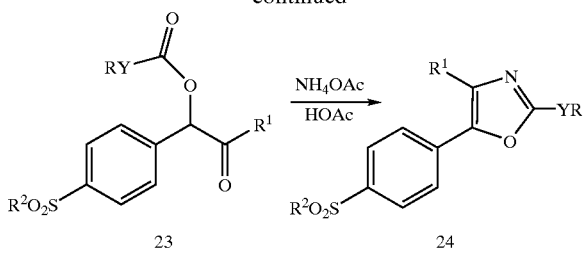

Diaryl/heteroaryl oxazoles can be prepared by the methods described in U.S. Pat. Nos. 3,743,656, 3,644,499 and 3,647,858, and PCT documents WO 95/00501 and WO94/15932, which are incorporated by reference.

Scheme VI

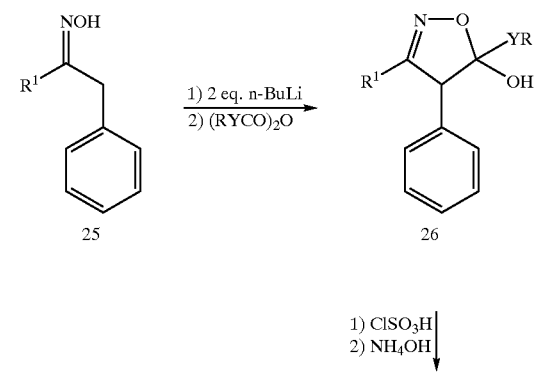

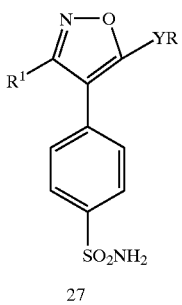

Diaryl/heteroaryl isoxazoles can be prepared by the methods described in PCT documents WO92/05162, and WO92/19604, and European Publication EP 26928 which are incorporated by reference. Sulfonamides 27 can be formed from the hydrated isoxazole 26 in a two step procedure. First, hydrated isoxazole 26 is treated at about 0° C. with two or three equivalents of chlorosulfonic acid to form the corresponding sulfonyl chloride. In step two, the sulfonyl chloride thus formed is treated with concentrated ammonia to provide the sulfonamide derivative 27.

of inert solvents such as toluene, benzene, and xylene, gives amidines 30. In step 2, the reaction of amidine 30 with 2-haloketones (where X is Br or Cl) in the presence of bases, such as sodium bicarbonate, potassium carbonate, sodium carbonate, potassium bicarbonate or hindered tertiary amines such as N,N'-diisopropylethylamine, gives the 4,5-dihydroimidazoles 31 (where $R^c$ is hydroxyl, $R^d$ is hydrido and $R^e$ is alkyl, halo or hydrido). Some of the suitable solvents for this reaction are isopropanol, acetone and dimethylformamide. The reaction may be carried out at temperatures of about 20° C. to about 90° C. In step 3, the 4,5-dihydroimidazoles 31 may be dehydrated in the presence of an acid catalyst such as 4-toluenesulfonic acid or mineral acids to form the 1,2-disubstituted imidazoles 32 of the invention. Suitable solvents for this dehydration step are e.g., toluene, xylene and benzene. Trifluoroacetic acid can be used as solvent and catalyst for this dehydration step.

In some cases (e.g., where YR=methyl or phenyl) the intermediate 31 may not be readily isolable. The reaction, under the conditions described above, proceeds to give the targeted imidazoles directly.

Scheme VII

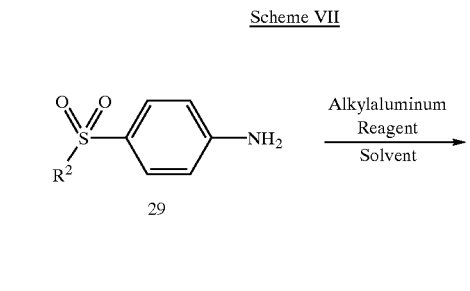

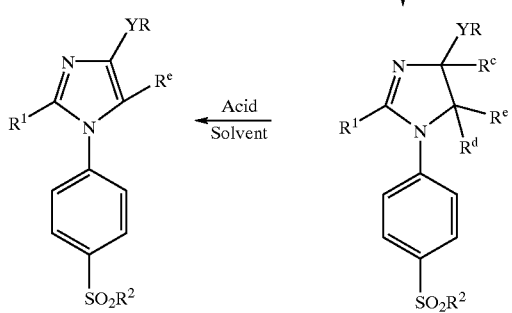

Scheme VII shows the three step preparation of the substituted imidazoles 32 of the present invention. In step 1, the reaction of substituted nitrites ($R^1CN$) 28 with primary phenylamines 29 in the presence of alkylaluminum reagents such as trimethylaluminum, triethylaluminum, dimethylaluminum chloride, diethylaluminum chloride in the presence Similarly, imidazoles can be prepared having the sulfonylphenyl moiety attached at position 2 and $R^1$ attached at the nitrogen atom at position 1. Diaryl/heteroarylimidazoles can be prepared by the methods described in U.S. Pat. No. 4,822,805, and PCT document WO 93/14082, which are incorporated by reference.

Scheme VIII

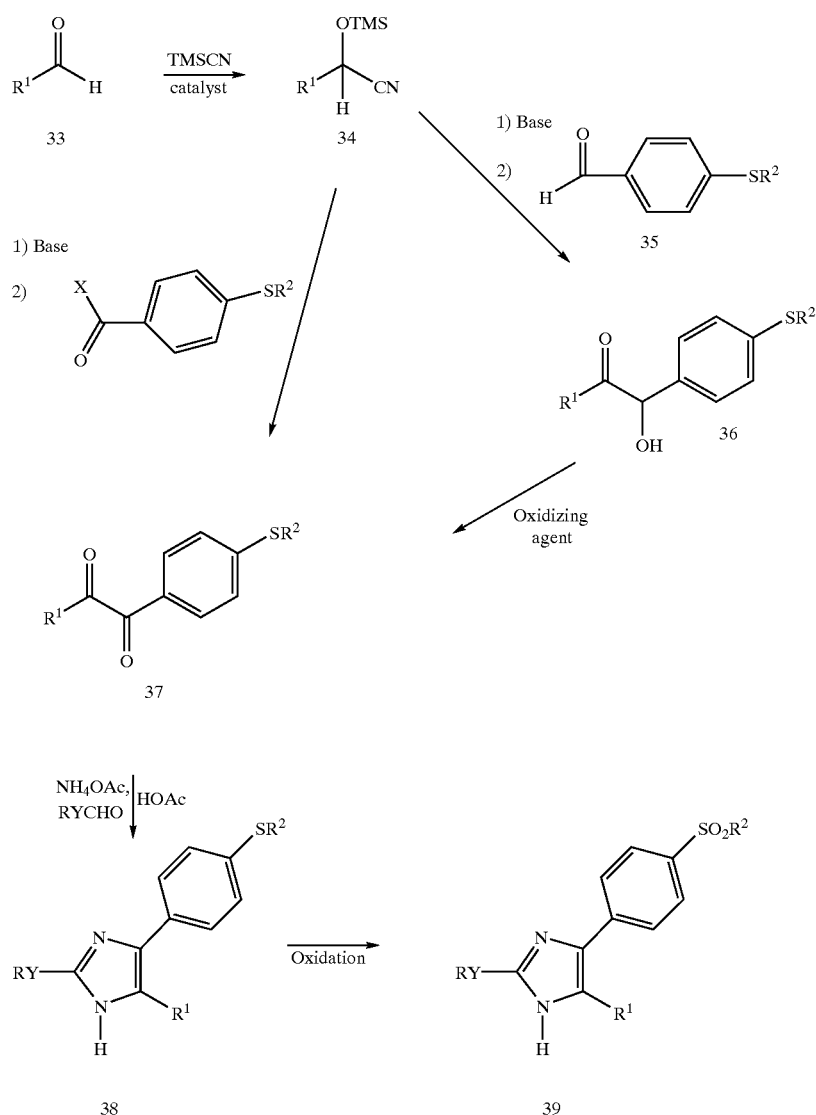

The subject imidazole compounds 39 of this invention may be synthesized according to the sequence outlined in Scheme VIII. Aldehyde 33 may be converted to the protected cyanohydrin 34 by reaction with a trialkylsilyl cyanide, such as trimethylsilyl cyanide (TMSCN) in the presence of a catalyst such as zinc iodide ($ZnI_2$) or potassium cyanide (KCN). Reaction of cyanohydrin 34 with a strong base followed by treatment with benzaldehyde 35 (where $R^2$ is alkyl) and using both acid and base treatments, in that order, on workup gives benzoin 36. Examples of strong bases suitable for this reaction are lithium diisopropylamide (LDA) and lithium hexamethyldisilazane. Benzoin 36 may be converted to benzil 37 by reaction with a suitable oxidizing agent, such as bismuth oxide or manganese dioxide, or by a Swern oxidation using dimethyl sulfoxide (DMSO) and trifluoroacetic anhydride. Benzil 37 may be obtained directly by reaction of the anion of cyanohydrin 34 with a substituted benzoic acid halide. Any of compounds 36 and 37 may be used as intermediates for conversion to imidazoles 38 (where $R^2$ is alkyl) according to chemical procedures known by those skilled in the art and described by M. R. Grimmett, "Advances in Imidazole Chemistsy" in Advances in Heterocyclic Chemistry, 12, 104 (1970). The conversion of 37 to imidazoles 38 is carried out by reaction with ammonium acetate and an appropriate aldehyde (RYCHO) in acetic acid. Benzoin 36 may be converted to imidazoles 38 by reaction with formamide. In addition, benzoin 36 may be converted to imidazoles by first acylating with an appropriate acyl group (RYCO—) and then treating with ammonium hydroxide. Those skilled in the art will recognize that the oxidation of the sulfide (where $R^2$ is methyl) to the sulfone may be carried out at any point along the way beginning with compounds 35, and including oxidation of imidazoles 38, using, for examples, reagents such as hydrogen peroxide in acetic acid, m-chloroperoxybenzoic acid (MCPBA) and potassium peroxymonosulfate (OXONE®).

Diaryl/heteroarylimidazoles can be prepared by the methods described in U.S. Pat. Nos. 3,707,475, 4,686,231, 4,503,065, 4,472,422, 4,372,964, 4,576,958, 3,901,908, European publication EP 372,445, and PCT document WO 95/00501, which are incorporated by reference.

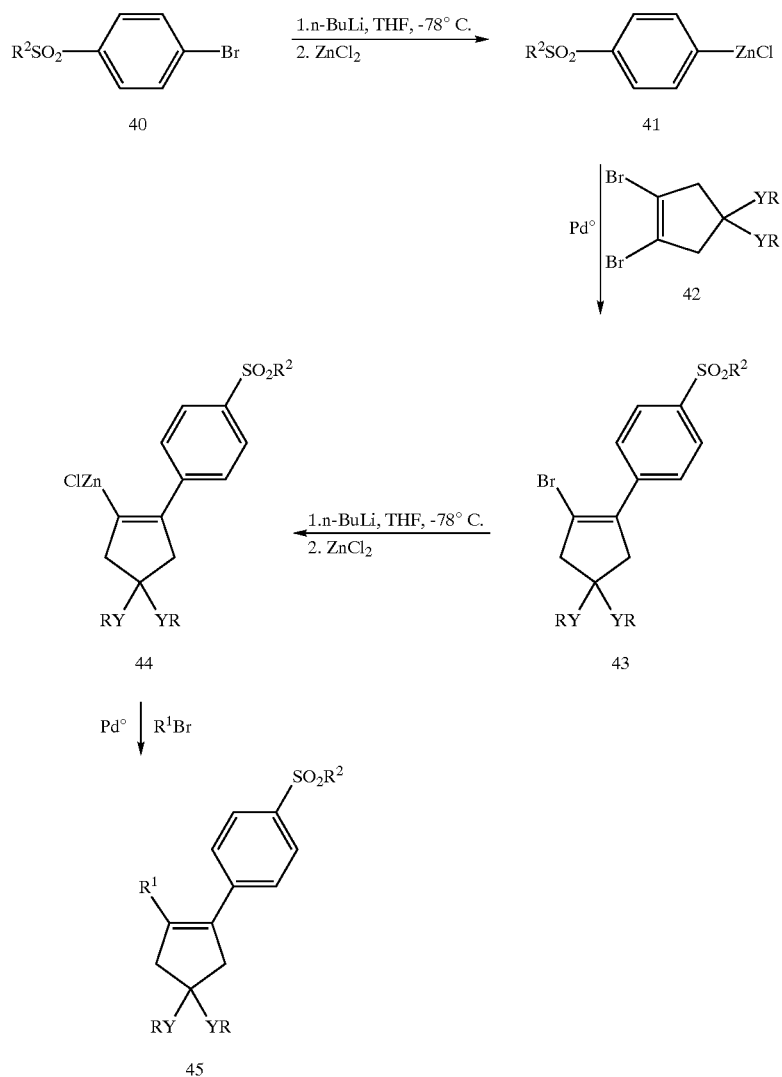

Diaryl/heteroaryl cyclopentenes can be prepared by the methods described in U.S. Pat. No. 5,344,991, and PCT document WO 95/00501, which are incorporated by reference.

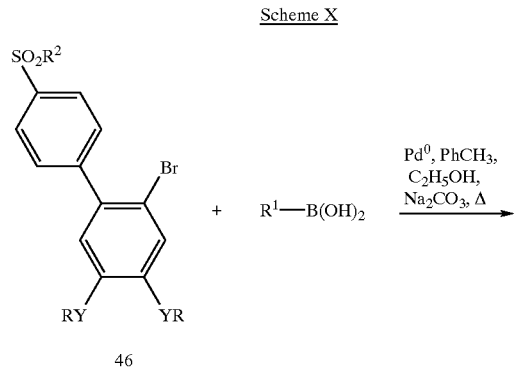

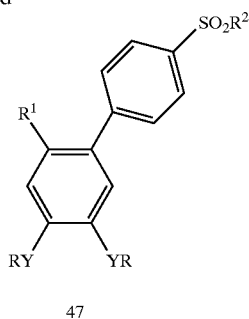

Similarly, Synthetic Scheme X shows the procedure for the preparation of 1,2-diarylbenzene antiinflammatory agents 47 from 2-bromo-biphenyl intermediates 46 (prepared similar to that described in Synthetic Scheme IX) and the appropriate substituted phenylboronic acids. Using a coupling procedure similar to the one developed by Suzuki et al. [*Synth. Commun.*, 11, 513 (1981)], intermediates 46 are reacted with the boronic acids in toluene/ethanol at reflux in the presence of a Pd° catalyst, e.g., tetrakis(triphenylphosphine)palladium(0), and 2M sodium carbonate to give the corresponding 1,2-diarylbenzene antiinflammatory agents 47 of this invention.

Scheme XI

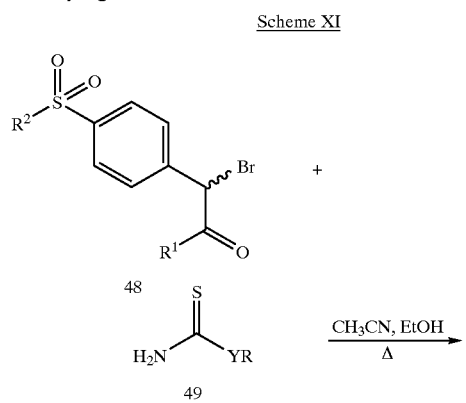

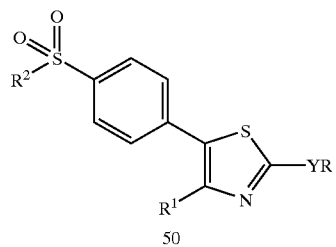

Diaryl/heteroaryl thiazoles can be prepared by the methods described in U.S. Pat. Nos. 4,051,250, 4,632,930, European Application EP 592,664, and PCT document WO 95/00501, which are incorporated by reference. Isothiazoles can be prepared as described in PCT document WO 95/00501.

Scheme XII

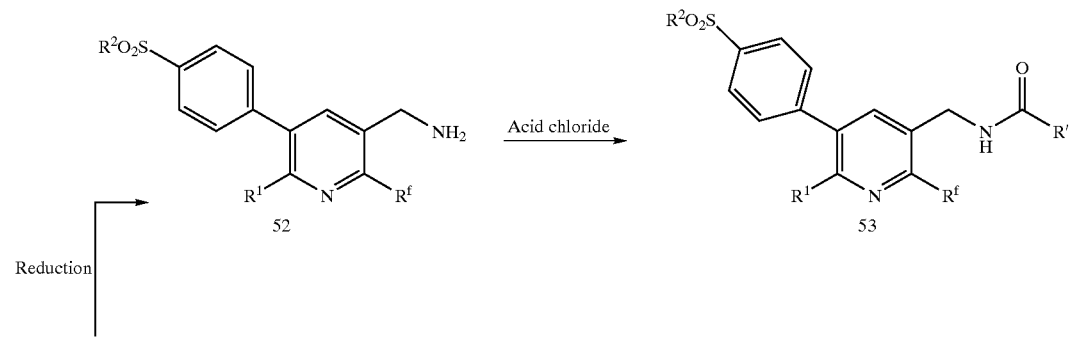

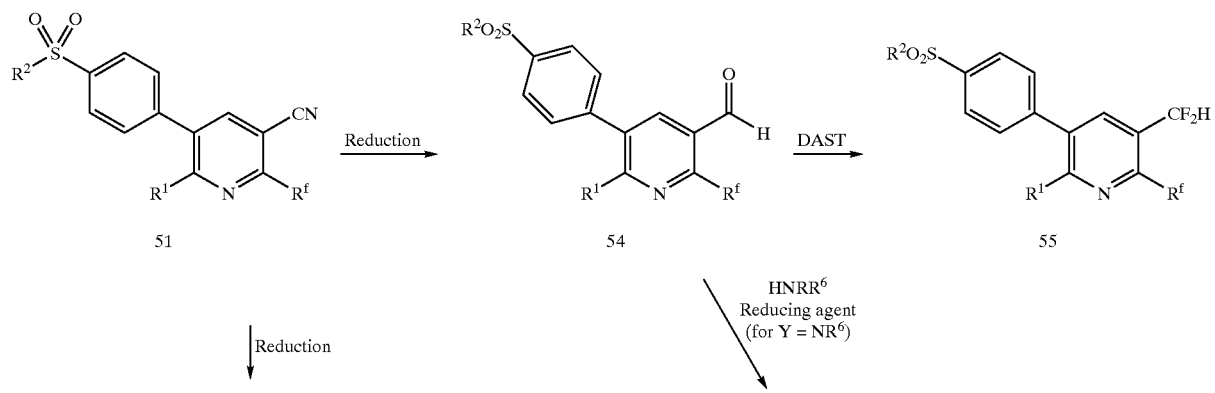

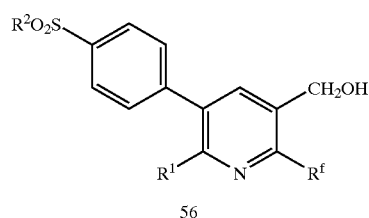

56

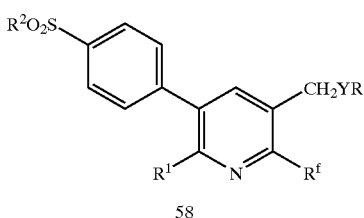

58

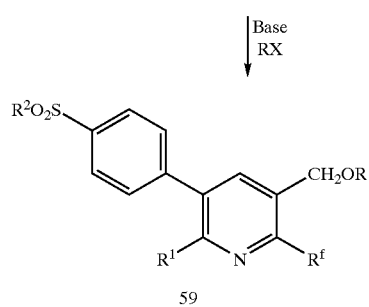

59

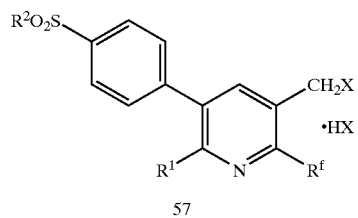

57

Diaryl/heteroaryl pyridines can be prepared by the methods described in U.S. Pat. Nos. 5,169,857, 4,011,328, and 4,533,666, which are incorporated by reference. For example, Synthetic Scheme XII shows the procedure used to prepare 3-alkylcarbonylaminoalkyl pyridine antiinflammatory agents 53, 3-haloalkyl pyridine antiinflammatory agents 55, 3-hydroxyalkyl pyridine antiinflammatory agents 56, heteroatom substituted 3-alkyl pyridine antiinflammatory agents 58 and 3-aryloxyalkyl pyridine antiinflammatory agents 59 from the corresponding carbonitriles 51 (where $R^f$ is hydrido, halo, alkoxy, haloalkoxy, aryl, alkylthio, alkylamino, aralkoxy, azido or allyloxy). The 3-alkylcarbonylaminoalkyl pyridine antiinflammatory agents 53 (where R' is alkyl) are prepared in a two step procedure from the carbonitriles 51. In step one, the carbonitrile 51 is reduced using reducing agents, such as diisobutyl aluminum hydride (DIBAL) in a solvent such as toluene or boranes in a solvent such as tetrahydrofuran at room temperature or reflux to form the aminoalkyl pyridines 52. Additional reducing reagent may be added to the solution. In step two, an acid chloride is added to the aminoalkyl pyridines 52 in a solvent such as ethyl ether or tetrahydrofuran and stirred to form the alkylcarbonylaminoalkyl pyridines 53. The 3-haloalkyl pyridine antiinflammatory agents 55 are prepared in a two step procedure from the carbonitriles 51. In step one, the carbonitriles 51 are reduced using agents, such as diisobutyl aluminum hydride (DIBAL) in a solvent such as toluene, at room temperature to form the aldehydes 54. The 3-hydroxyalkyl pyridines 56 also can be isolated from this reaction. In step two, a halogenating agent, such as diethylamino sulfur trifluoride (DAST) is added to the aldehyde 54 to form the haloalkyl pyridines 55. Reduction of aldehydes 54 with agents such as diisobutyl aluminum hydride (DIBAL) followed by methanol and water in methanol to yield the 3-hydroxyalkyl pyridines 56. Compound 56 is convertible to alkoxyalkyl and aralkoxyalkyl compounds 59 by sequential treatment first with a base and then with an alkyl or aralkyl halide. An example of a suitable base is sodium hydride. Examples of alkyl and aralkyl halides are methyl iodide and benzyl chloride. Alternatively, compound 56 may be converted to the haloalkyl compound 57 using a suitable halogenating agent, such as thionyl chloride. Under such circumstances, the hydrochloride salt may be isolated. This in turn may be converted to compounds 58 by reaction with the appropriate alcohol, thiol, or amine. It may be advantageous to carry out this reaction in the presence of a base. Examples of suitable alcohols are methanol, ethanol, benzyl alcohol and phenol. Examples of suitable thiols are n-butyl mercaptan, benzylthiol and thiophenol. Examples of suitable amines are dimethylamine, benzylamine, N-methylbenzylamine, aniline, N-methylaniline and diphenylamine. Examples of suitable bases are sodium hydride and potassium carbonate. Alternatively, amines are accessible by reaction of aldehyde 54 with a primary or secondary amine in the presence of a reducing agent. Examples of suitable primary amines are methyl amine and ethylamine. An example of a suitable secondary amine is dimethylamine. Suitable reducing agents include sodium cyanoborohydride and sodium borohydride.

Scheme XIII

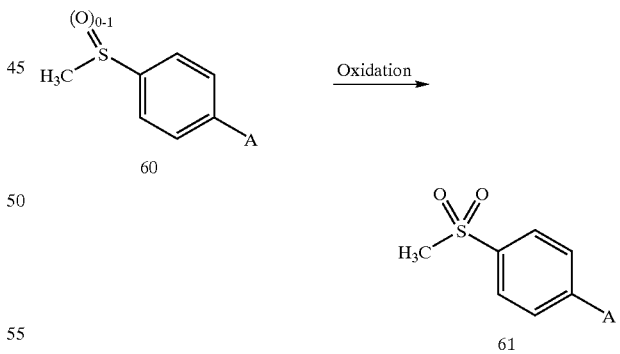

Scheme XIII shows a method to form the alkylsulfonylphenyl substituted compounds 61 of the current invention by oxidation of alkylthio or alkylsulfinyl derivatives 60. Aqueous-hydrogen peroxide (30%) is added to a suspension of a (methylthio)phenyl substituted compound 60 in acetic acid. The mixture is stirred while heating to about 100° C. for about 2 hours. Alternatively, m-chloroperoxybenzoic acid (MCPBA), and other oxidizing agents (potassium peroxymonosulfate (OXONE®)] can be used to form the sulfonyl radicals 61.

Scheme XIV

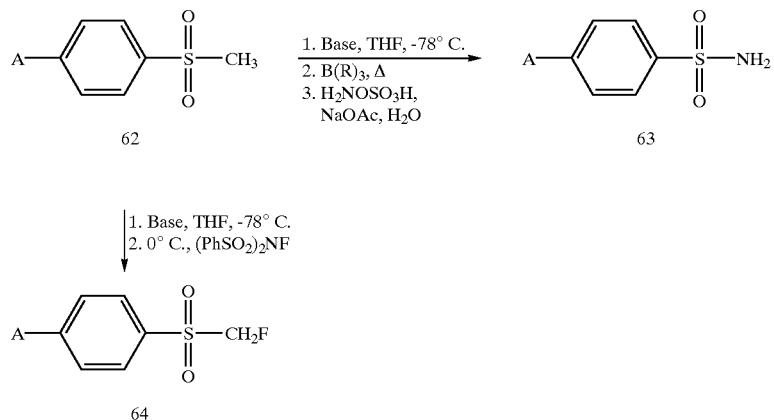

Synthetic Scheme XIV shows the three step procedure used to prepare sulfonamide antiinflammatory agents 63 and the two step procedure used to prepare fluoromethyl sulfone antiinflammatory agents 64 from their corresponding methyl sulfones 62. In step one, THF solutions of the methyl sulfones 62 at −78° C. are treated with an alkyllithium reagent, e.g., methyllithium, n-butyllithium, etc. In step two, the anions generated in step one are treated with an organoborane, e.g., triethylborane, tributylborane, etc., at −78° C. then allowed to warm to ambient temperature prior to stirring at reflux. In step three, an aqueous solution of sodium acetate and hydroxylamine-O-sulfonic acid is added to provide the corresponding sulfonamide antiinflammatory agents 63 of this invention. As an alternative to the borane chemistry found in step two above, the base treated sulfone is reacted with an alkylsilane, such as (iodomethyl)trimethylsilane or (chloromethyl)trimethylsilane, at room temperature to give a silylalkylsulfone. The silylalkylsulfone is converted to a sulfinic acid salt by heating to about 90° C. with tetrabutylammoniumfluoride. Treatment proceeds as in step three above to produce the sulfonamide.

Alternatively, the anion solutions generated in step one may be warmed to 0° C. and treated with N-fluorodibenzenesulfonamide to provide the corresponding fluoromethyl sulfone antiinflammatory agents 64 of this invention.

Scheme XV

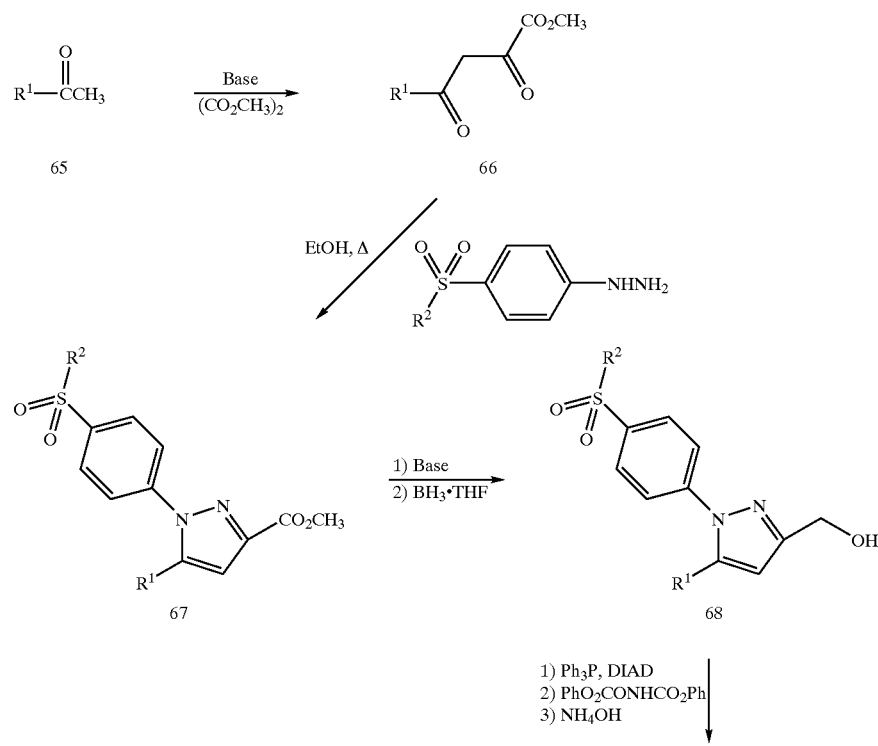

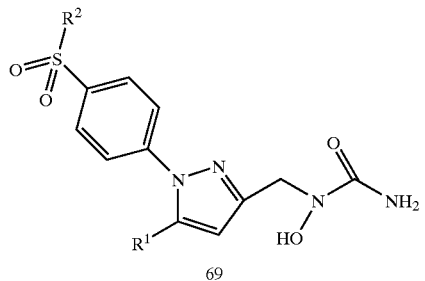

Synthetic Scheme XV shows a method of making the pyrazole ureas 69 of the present invention. In step 1, the dione 66 is formed from ketone 65 through the addition of a base, such as lithium bis(trimethylsilyl)amide or lithium diisopropylamide (LDA), followed by reacting with an appropriate acetylating reagent, such as $(CO_2CH_3)_2$. Treatment of the dione 66 with a phenylhydrazide yields the pyrazole ester 67. The pyrazole ester 67 is reduced to the alcohol 68 by treatment with base: and borane in THF. In step four, the alcohol 68 is reacted with triphenylphosphine, an alkyl azodicarboxylate (e.g. diisopropyl azodicarboxylate (DIAD) and diethyl azodicarboxylate (DEAD)), and bis (phenoxycarbonyl) hydroxylamine [prepared by the method of Stewart and Brooks, *J. Org. Chem.*, 57, 5020–23 (1992)] in a solvent such as tetrahydrofuran (THF) at about 0° C. to room temperature. Aminolysis with ammonium hydroxide yields the anti-inflammatory ureas 69 of the present invention.

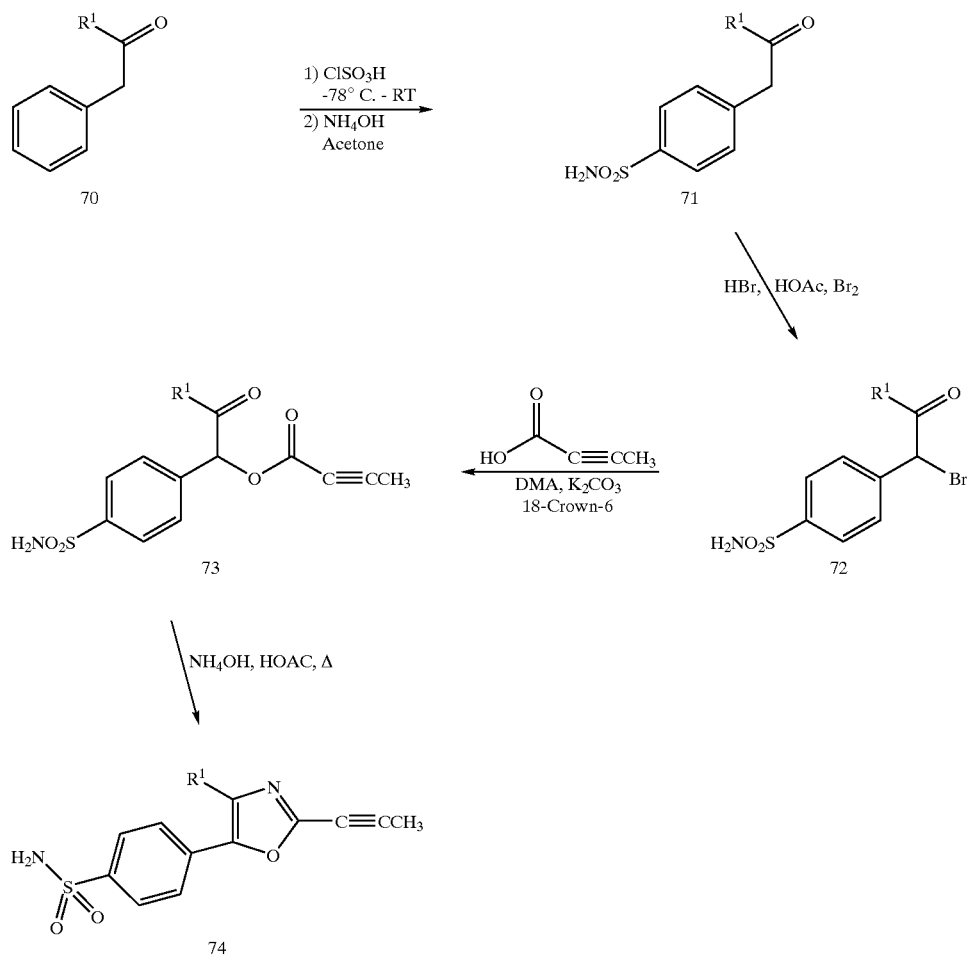

Scheme XVI

Scheme XVI shows a procedure for forming an alkynyl oxazole 74 (where $R^2$ is amino), similar to that shown in Scheme V above. The ketone sulfonamide 71 is formed from ketone 70 through chlorosulfonation and ammonolysis with ammonium hydroxide in a solvent such as acetone. The ketone sulfonamide 71 is halogenated, such as with HBr in acetic acid and bromine, to form the haloketone sulfonamide 72. Substitution with butynoic acid in the presence of $K_2CO_3$, a crown ether such as 18-Crown-6 and dimethylacetamide (Dak) yields the alkynyl ketoester 73. Conversion of the alkynyl ester 73 to the alkynyl oxazole 74 proceeds as previously described in Scheme V.

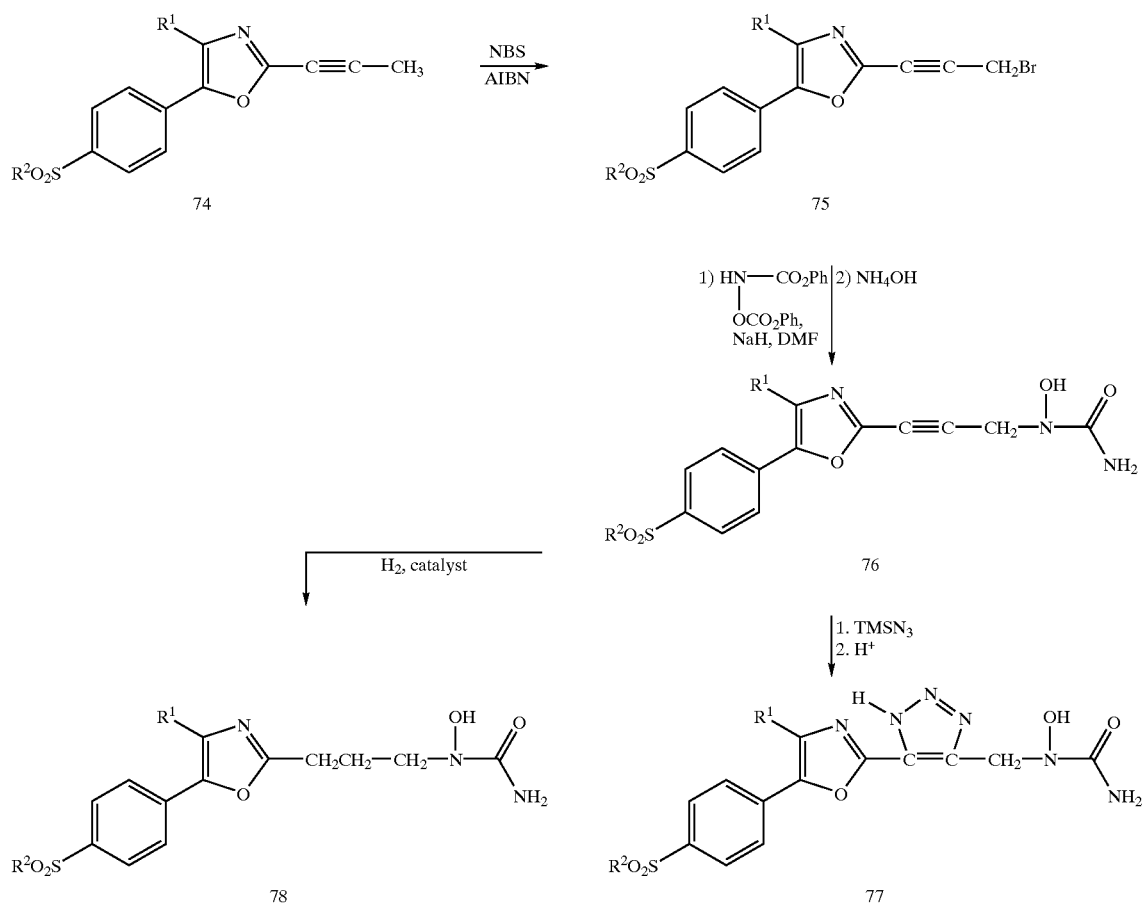

Synthetic Scheme XVII shows the procedures for forming heterocycloalkynyl ureas 76, heterocyclotriazole ureas 77 and heterocycloalkyl ureas 78, from the corresponding alkynes 74. The alkynes 74, such as formed in Scheme XVI, are halogenated, such as with N-bromosuccinimide (NBS) and 2,2'-azobis(2-methylpropionitrile (AIBN), to form the haloalkynes 75. The alkynyl halide 75 can be converted into the urea by a three step procedure. In the first step, the halide 75 is treated with bis(phenoxycarbonyl)hydroxylamine. Aminolysis with ammonium hydroxide yields the ureas 76 of the present invention. The alkynyl ureas 76 can be converted to heterocyclo-containing ureas 77, such as by treatment with azidotrimethylsilane, followed by acid. Alternatively, the alkynyl ureas 76 can be reduced, such as with hydrogen in the presence of catalyst (e.g., palladium) to yield the heterocycloalkyl ureas 78.

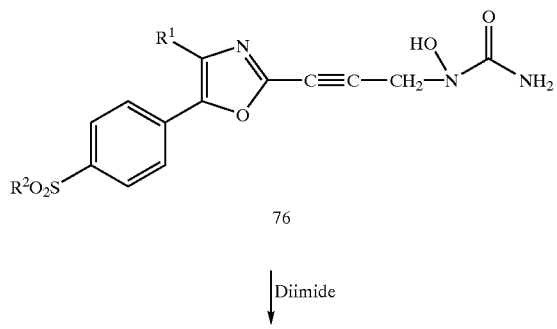

61

-continued

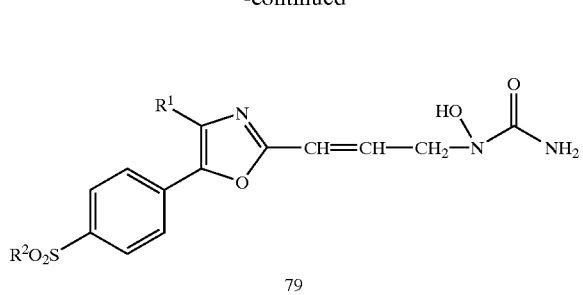

79

62

-continued

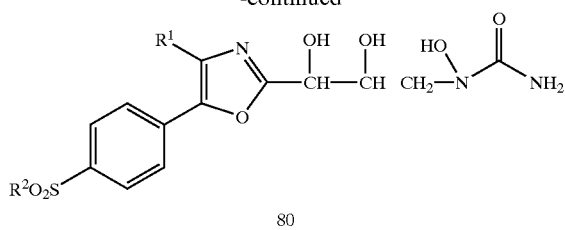

80

Scheme XVIII shows a method of forming the alkenyl ureas 79, and diols 80 of the present invention from the appropriate alkynyl ureas 76. In Step one, treatment with diimide reduces the alkynyl ureas 77 to the alkenyl ureas 79. Oxidation of the alkenyl urea 79, such as with osmium tetraoxide and hydrogen peroxide, yields the diols 80 of the present invention.

Scheme XIX

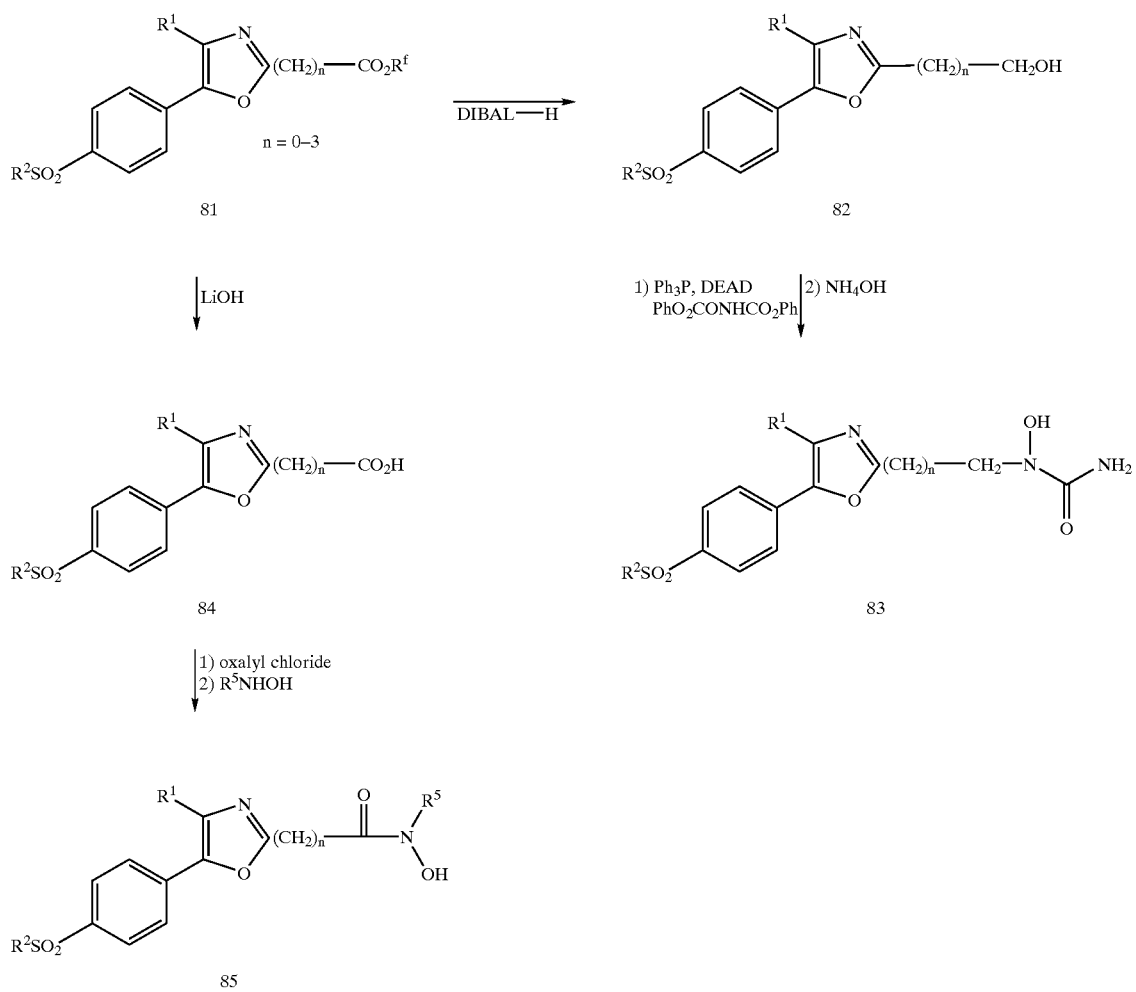

Scheme XIX shows the preparation of ureas 83 and amides 85 antiinflammatory agents of the present invention. Esters 81 (where $R^i$ is alkyl, as provided for in WO94/27980) can be converted to the alcohols 82 by treatment with a reducing agent, such as DIBAL-H. Alcohols 82 can be directly converted to the protected urea by treating with triphenylphosphine, diethyl azodicarboxylate (DEAD), and N,O-bis(phenoxycarbonyl)hydroxylamine. Aminolysis with ammonium hydroxide yields the urea 83. Alternatively, the esters 81 can be hydrolyzed to the acids 84 with base such as LiOH. Amides 85 are formed from the acid 84 by treatment with oxalyl chloride to form the corresponding acid chlorides, followed by substitution with the hydroxylamines.

Scheme XX

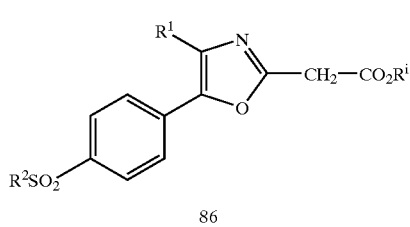

86

1. NaH
2. ArCH$_2$Br

-continued

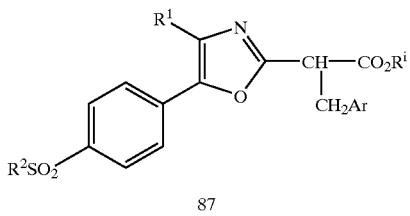

87

1. LiOH
2. SOCl$_2$
3. HNOHR$^5$

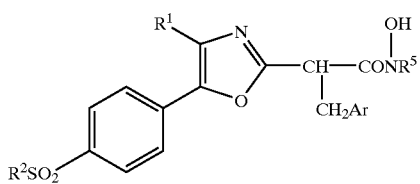

88

Scheme XX shows the preparation of the antiinflammatory amides 88 of the present invention. Base treatment of ester 86, such as with sodium hydride, followed by addition of an aralkyl halide or heteroaralkyl halide forms the ester 87. Formation of the amide 88 from the esters 87 occurs in a three step procedure. Treatment with base, such as lithium hydroxide, and thionyl chloride yields the acid chloride. Addition of a hydroxylamine yields the amide 88.

Scheme XXI

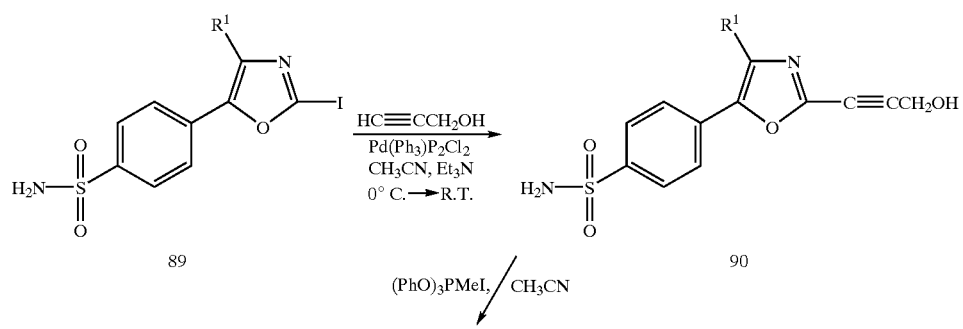

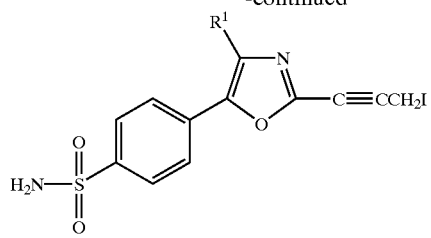

91

Scheme XXI shows an alternative preparation of the alkynyl alcohol 90 and alkynyl halides 91 previously described in Scheme XVII. Cyclic halides 89 can be converted to the substituted alkynyl alcohols 90 by reacting an alkynyl alcohol with the halides 89 in the presence of base and bis(triphenylphosphine)palladium(II)chloride. The alkynyl alcohol 90 can be converted to the alkynyl halide 91 by treatment with triphenoxyphosphonium methyliodide.

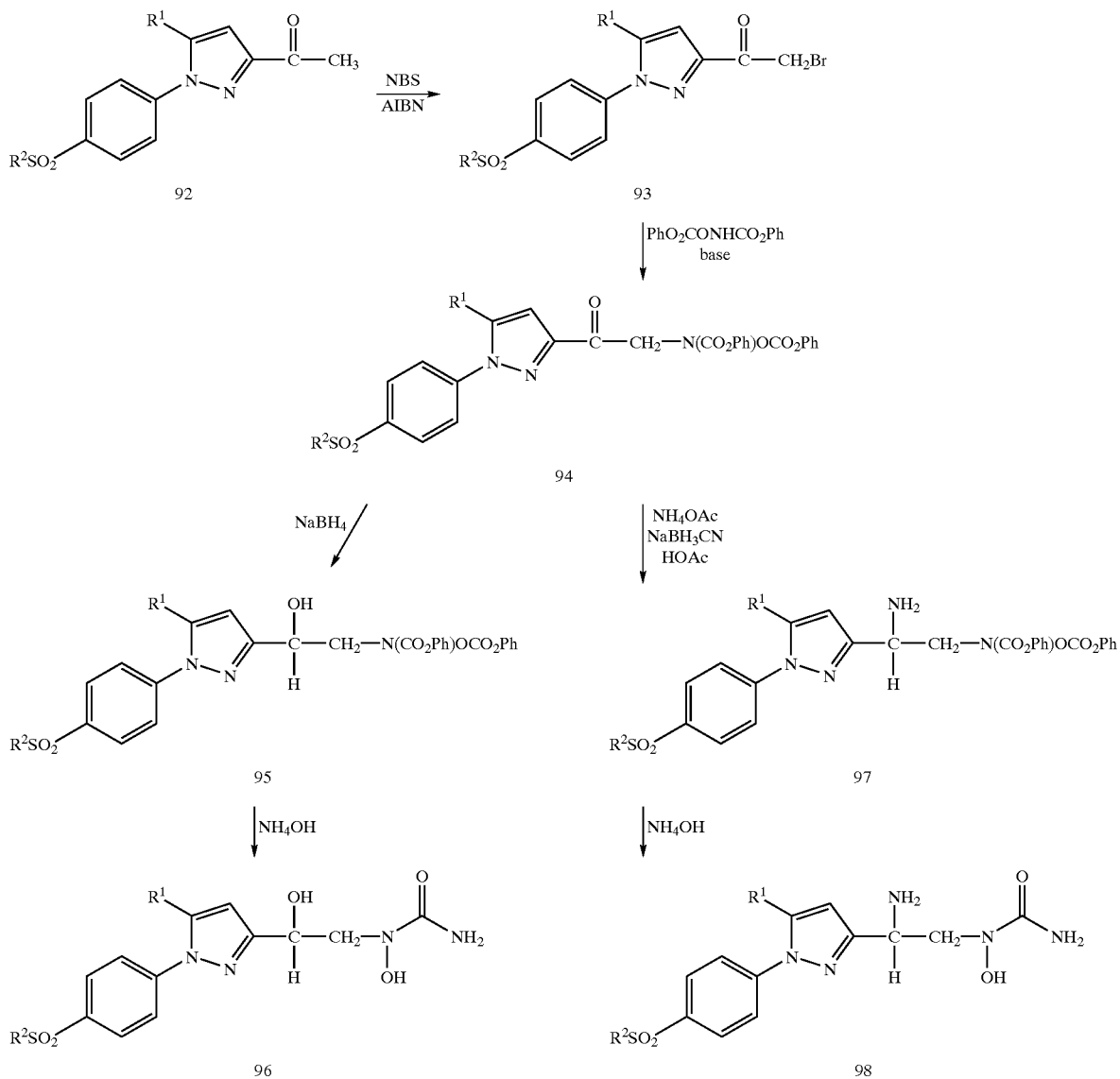

Scheme XXII

Additional antiinflammatory agents containing various substituted alkyl spacer radicals including hydroxyalkylureas 96 and aminoalkylureas 98, can be prepared from ketones 92, by the procedures shown in Scheme XXII. The ketones 92 are halogenated to form haloketones 93, such as by treatment with NBS in the presence of AIBN. Treatment of the halides 93 with bis(phenoxycarbonyl)hydroxylamine in the presence of base, such as sodium hydride, generates the protected (ketoalkyl)hydroxylamines 94. The protected (ketoalkyl)hydroxylamines 94 can be converted to the protected (hydroxyalkyl)hydroxylamines 95 by reducing the carbonyl, such as with sodium borohydride. Deprotection, such as with ammonium hydroxide, yields the hydroxyalkylureas 96. Amination of the protected (ketoalkyl) hydroxylamines 94 by reaction with ammonium acetate and sodium cyanoborohydride in the presence of acetic acid generates the protected (aminoalkyl)hydroxylamines 97. Deprotection, such as with ammonium hydroxide, yields the aminoalkylureas 98.

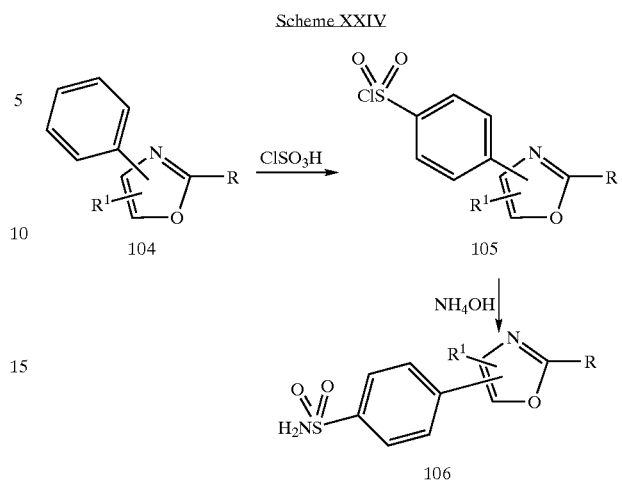

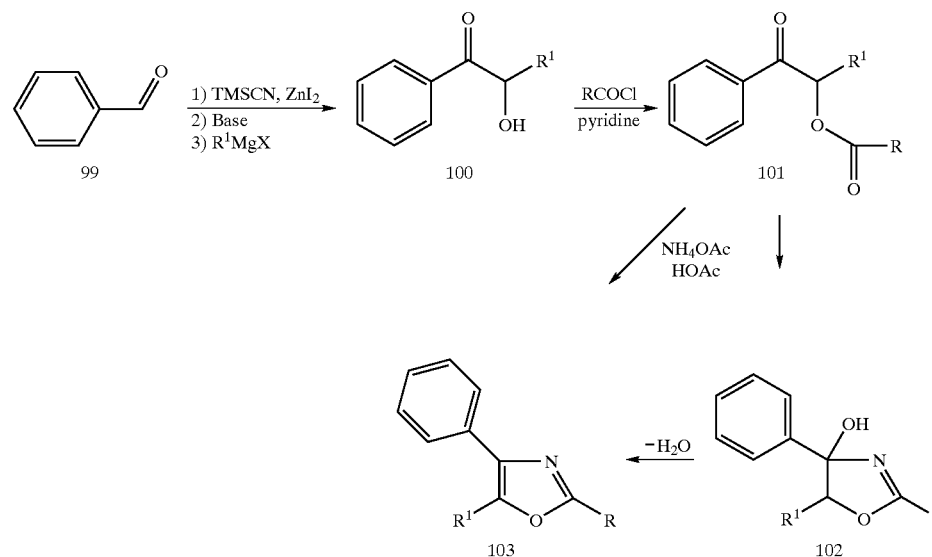

Scheme XXIII shows a method for preparing oxazoles 103. A solution of aldehyde 99 and zinc iodide in an organic solvent such as dichloromethane is treated with trimethylsilylcyanide to give the trimethylsilyl cyanohydrin. The trimethylsilyl cyanohydrin is added to a solution of $R^1$-magnesium bromide in diethyl ether while maintaining the temperature between 25–35° C. to give the benzoin 100. The benzoin 100, pyridine, and acid chloride are reacted at room temperature to yield the benzoin ester 101. Addition of ammonium acetate to the benzoin ester 101 yields the oxazole 103. Alternatively, the hydroxy-oxazoline 102 is isolated. Dehydration of the hydroxy-oxazoline 102 yields the oxazoles 103. By reversing the positions of $R^1$ and the phenyl group in benzoin 100, oxazoles can be prepared where $R^1$ is at position 4.

Scheme XXIV shows a method of preparing oxazolylbenzenesulfonamides 106 of the present invention. The oxazole 104 is stirred with chlorosulfonic acid at about 5° C. to give the sulfonyl chlorides 105. The sulfonyl chloride 105 is reacted at about 5° C. with ammonium hydroxide to give the sulfonamides 106 of the current invention.

The following examples contain detailed descriptions of the methods of preparation of compounds of Formulas I–III. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated. All compounds showed NMR spectra consistent with their assigned structures.

EXAMPLE 1

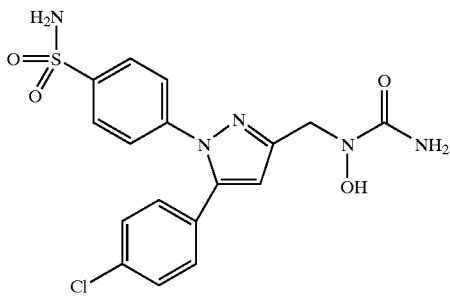

N'-[[1-[4-(Aminosulfonyl)phenyl]-5-(4-chlorophenyl)-1H-pyrazol-3-yl]methyl]-N'-hydroxyurea Step 1. Preparation of methyl-4-(4-chlorophenyl)-2,4-dioxobutanoate.

Dimethyl oxalate (15.27 g, 0.129 mol) and 4'-chloroacetophenone (20.0 g, 0.129 mol) were diluted with methanol (300 mL) and sodium methoxide (25 wt % in methanol, 70 mL) was added in one portion. The reaction was stirred at room temperature for 16 hours (the reaction became an insoluble mass during this time). The solid was mechanically broken up, hydrochloric acid (conc. 70 mL) was added, and the white suspension was stirred vigorously at room temperature for 1 hour. The suspension was cooled to 0° C. and held for 0.5 hour. The solid was filtered, and the filter cake was washed with cold water (100 mL). Upon drying, methyl-4-[4-(chloro)phenyl]-2,4-dioxobutanoate was obtained (16.94 g, 54.4%) as the enol: mp 108.5–110.5° C. $^1$H NMR (CDCl$_3$/300 MHz) δ 7.94 (d, J=8.66 Hz, 2H), 7.48 (d, J=8.66 Hz, 2H), 7.04 (S, 1H), 3.95 (s, 3H), 3.48 (s, 1H).

Step 2. Preparation of methyl 1-(4-aminosulfonylphenyl)-5-(4-chlorophenyl)-1H-pyrazole-3-carboxylate Methyl-4-[4-(chloro)phenyl]-2,4-dioxobutanoate from Step 1 (5.0 g, 20.78 mmol) was added to 4-sulfonamidylphenyl hydrazine hydrochloride (5.11 g, 22.86 mmol) and methanol (50 mL). The reaction vessel was heated to reflux and held for 16 hours. A precipitate formed overnight. The suspension was cooled to 0° C., held for 0.5 hour, filtered and washed with cold water to provide, after air drying, 7.91 g, 91% of crude pyrazole. Recrystallization of 3.50 g from boiling ethanol yielded 3.14 g (90%) of pure methyl 1-(4-aminosulfonylphenyl)-5-(4-chlorophenyl)-1H-pyrazole-3-carboxylate: mp 227° C.; $^1$H NMR (CDCl$_3$/300 MHz) δ 7.91 (d, J=8.86 Hz, 2H), 7.44 (d, J=8.86 Hz, 2H), 7.33 (d, J=8.66 Hz, 2H), 7.14 (d, J=8.66 Hz, 2H), 7.03 (s, 1H), 3.96 (s, 3H). Mass Spectrum, MH+=392. Anal. Calc'd for C$_{17}$H$_{14}$N$_3$O$_4$ClS: C, 52.11; H, 3.60; N, 10.72; Cl, 9.05; S, 8.18. Found: C, 52.07; H, 3.57; N, 10.76; Cl, 9.11; S, 8.27.

Step 3. Preparation of 1-(4-aminosulfonylphenyl)-5-(4-chlorophenyl)-1H-pyrazole-3-carboxylic acid Methyl 1-(4-aminosulfonylphenyl)-5-(4-chlorophenyl)-1H-pyrazole-3-carboxylate from Step 2 (1.0 g, 2.66 mmol) was added to tetrahydrofuran (20 mL). Aqueous sodium hydroxide (2.5 N, 2.7 mL) and water (2.5 mL) were added, and the suspension was heated to reflux and held for 16 hours. The solids dissolved during this time. The reaction was cooled to room temperature, and hydrochloric acid solution (1 N, 11 mL) was added. The aqueous suspension was extracted with methylene chloride (2×20 mL). The combined organic solution was dried over anhydrous magnesium sulfate, filtered, and concentrated in vacuo to an oil. Trituration with 30 mL of dichloromethane yielded, upon filtration and drying, 1-(4-aminosulfonylphenyl)-5-(4-chlorophenyl)-1H-pyrazole-3-carboxylic acid (0.90 g (94%)) as a white solid: mp 126–128° C.

Step 4. Preparation of 4-[5-(4-chlorophenyl)-3-hydroxymethyl-1H-pyrazol-1-yl]benzenesulfonamide.

4-(4-(Aminosulfonyl)phenyl-5-(4-chlorophenyl)-1H-pyrazole-3-carboxylic acid from Step 3 (3.8 g, 10 mmol) and tetrahydrofuran (100 mL) was stirred at room temperature during the dropwise addition of 1.0 M borane-tetrahydrofuran complex (30 mL, 30 mmol). The mixture was heated to reflux for 16 hours. The solution was cooled and methanol was added dropwise until gas evolution ceased. Ethyl acetate (100 mL) was added and the solution was washed with 1N hydrochloric acid, brine, and sat. aq. sodium bicarbonate solution, dried over magnesium sulfate, filtered and concentrated. The resultant material was recrystallized from ethanol:water to yield 4-[5-(4-chlorophenyl)-3-hydroxymethyl-1H-pyrazol-1-yl]benzenesulfonamide (2.6 g, 71%) as a white solid: mp 192–194° C.; $^1$H NMR (DMSO-d$_6$/300 MHz) δ 7.81 (d, J=8.7 Hz, 2H), 7.46 (d, J=8.4 Hz, 2H), 7.42 (brs, 2H), 7.40 (d, J=8.7 Hz, 2H), 7.26 (d, J=8.4 Hz, 2H), 6.63 (s, 1H), 5.35 (t, J=8.0 Hz, 1H), 4.50 (d, J=8.0 Hz, 2H). Anal. Calc'd for C$_{16}$H$_{14}$N$_3$SO$_2$Cl: C, 52.82; H, 3.88; N, 11.55. Found: C, 52.91; H, 3.88; N, 11.50.

Step 5. Preparation of [[1-[4-(aminosulfonyl)phenyl]-5-(4-chlorophenyl)-1H-pyrazol-3-yl]methyl]-N,O-bis(phenoxycarbonyl)hydroxylamine.

A solution of 4-[5-(4-chlorophenyl)-3-hydroxymethyl-1H-pyrazol-1-yl]benzenesulfonamide from Step 4 (7.28 g, 0.02 mol), triphenylphosphine (6.29 g, 0.024 mol) and N,O-bis(phenoxycarbonyl)hydroxylamine prepared as-described by A. O. Stewart and D. W. Brooks, [J. Org. Chem., 57, 5020–5023 (1992)] (6.01 g, 0.022 mol) in 250 mL of anhydrous tetrahydrofuran (THF) was cooled to 0° C. and treated with diisopropylazo-dicarboxylate (3.75 g, 0.024 mol) dissolved in 25 mL of THF. The solution was stirred at room temperature for 3 hours, concentrated in vacuo and the residue purified by flash chromatography on silica gel eluting with ethyl acetate/hexane (2:3) to afford 9.30 g, 75% of the protected hydroxylamine as a thick clear oil that was used directly in the next step.

Step 6. Preparation of N'-[[1-[4-(aminosulfonyl) phenyl]-5-(4-chlorophenyl)-1H-pyrazol-3-yl]methyl]-N'-hydroxyurea.

The compound from Step 5 (6.0 g, 9.7 mmol) was dissolved in 150 mL of ethanol and the solution was saturated with ammonia. The solution was let stand undisturbed overnight and then concentrated in vacuo. The residue was dissolved in ethyl acetate, washed with 1 N HCl and brine, dried over anhyd. MgSO$_4$, filtered and concentrated in vacuo to afford N'-[[1-[4-(aminosulfonyl)phenyl]-5-(4-chlorophenyl)-1H-pyrazol-3-yl]methyl]-N'-hydroxyurea as a white solid that was crystallized from a mixture of ethyl acetate and hexane: mp 216–218° C.

EXAMPLE 2

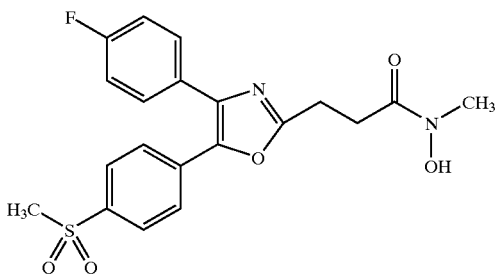

4-(4-Fluorophenyl)-N-hydroxy-N-methyl-5-[(4-methylsulfonyl)phenyl]-2-oxazolepropanamide A solution of 4-(4-fluorophenyl)-5-[4-(methylsulfonyl)phenyl]-2-oxazoleproprionic acid (U.S. Pat. No. 5,380,738) (500 mg, 1.28 mmol) was dissolved in 20 mL of dichloromethane containing 50 μL of dimethylformamide (DMF). This solution was cooled to 0° C. and treated with oxalyl chloride (130 μL, 1.54 mmol, 1.2 equivalents). The solution was warmed to room temperature and stirred for 3 hours, and concentrated in vacuo. The residue was taken back up in dichloromethane and added dropwise to a solution of N-methyl hydroxylamine hydrochloride (129 mg, 1.54 mmol, 1.2 equivalents) and triethylamine (390 μL, 2.82 mmol, 2.2 equivalents) in 20 mL of dichloromethane at 0° C. The solution was stirred at room temperature for 1 hour and diluted with water. The phases were separated and the dichloromethane layer was washed with 1 N HCl, brine, dried over anhydrous $MgSO_4$, filtered and concentrated in vacuo to provide a yellow solid that was recrystallized from a mixture of ethyl acetate and isooctane to provide 4-(4-fluorophenyl)-N-hydroxy-N-methyl-5-[(4-methylsulfonyl)phenyl]-2-oxazolepropanamide (455 mg, 85%): $^1$H-NMR ($CDCl_3$, 300 MHz) −3.12 (s, 3H), 3.15 (t, 2H, J=6.6 Hz), 3.28 (s, 3H), 3.41 (t, 2H, J=6.6 Hz), 7.20 (t, 2H, J=8.5 Hz), 7.54 (m, 2H), 7.75 (d, 2H, J=8.5 Hz) and 7.97 (d, 2H, J=8.5 Hz). LRMS m/z 418 (M)+. HRMS calc'd. for $C_{20}H_{19}N_2O_5FS$: 418.0999. Found: 418.0987. Anal. calc'd. for $C_{20}H_{19}N_2O_5FS$: C, 57.41; H, 4.58; N, 6.69. Found: C, 56.84; H, 4.50; N, 6.59.

EXAMPLE 3

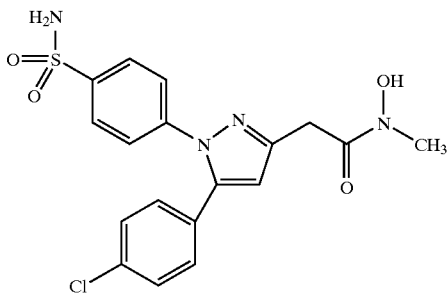

[1-[4-(Aminosulfonyl)phenyl]-5-(4-chlorophenyl)-1H-pyrazol-3-yl]-N-hydroxy-N-methyl-ethanamide Step 1. Preparation of 4-[5-(4-chlorophenyl)-3-chloromethyl-1H-pyrazol-1-yl]benzenesulfonamide.

4-[5-(4-Chlorophenyl)-3-(hydroxymethyl)-1H-pyrazol-1-yl]benzenesulfonamide (Example 1 Step 4) (3.0 g, 8.2 mmol) was dissolved in 100 mL of dry tetrahydrofuran and treated with para-toluenesulfonyl chloride (1.56 g, 8.2 mmol), lithium chloride (350 mg, 8.2 mmol), and triethylamine (830 mg, 8.2 mmol). The solution was warmed to reflux for 16 hours and diluted with 100 mL of ethyl acetate. The solution was washed with 1 N hydrochloric acid, saturated aqueous $NaHCO_3$, and water, dried over anhydrous $MgSO_4$, filtered and concentrated in vacuo. The residue was purified by flash chromatography over silica gel eluting with 1:1 (v:v) hexane/ethyl acetate. The appropriate fractions were combined and concentrated and the residue crystallized from ethanol/water to give pure 4-[5-(4-chlorophenyl)-3-chloromethyl-1H-pyrazol-1-yl]benzenesulfonamide as a white solid (2.51 g, 80%): mp 198–201° C. Anal. Calc'd. for $C_{16}H_{13}N_3S_1O_2Cl_2$: C, 50.27; H, 3.43; N, 10.99. Found: C, 50.34; H, 3.43; N, 10.96.

Step 2. Preparation of 4-[5-(4-chlorophenyl)-3-cyanomethyl-1-H-pyrazol-1-yl]benzenesulfonamide.

A solution of 4-[5-(4-chlorophenyl)-3-chloromethyl-1H-pyrazol-1-yl]benzenesulfonamide from step 1 (350 mg, 0.9 mmol) and sodium cyanide (200 mg), dissolved in 15 mL of dimethylsulfoxide, was warmed to 100° C. for 4 hours. The solution was cooled to room temperature, diluted with water and extracted with ethyl acetate. The ethyl acetate extracts were combined and washed with water, dried over anhydrous $MgSO_4$, filtered and concentrated in vacuo. The residue was purified by flash chromatography over silica gel eluting with 1:1 (v:v) hexane/ethyl acetate. The appropriate fractions were combined and concentrated, and the residue crystallized from ethanol/water to give 4-[5-(4-chlorophenyl)-3-cyanomethyl-1-H-pyrazol-1-yl]benzenesulfonamide as a white solid (251 mg, 75%): mp 212–214° C. Anal. Calc'd. for $C_{17}H_{13}ClN_4O_2S_1$: C, 54.77; H, 3.51; N, 15.03. Found: C, 54.94; H, 3.61; N, 14.88.

Step 3. Preparation of [[1-[4-(aminosulfonyl)phenyl]-5-(4-chlorophenyl)-1H-pyrazol-3-yl]acetic acid.

To a solution of 4-[5-(4-chlorophenyl)-3-(cyanomethyl)-1H-pyrazol-1-yl]benzenesulfonamide from step 2 (0.340 g, 3.594 mmol) in ethanol (250 mL) at −10° C., HCl gas was added via a fritted gas inlet tube over 6 hours. The reaction mixture was concentrated in vacuo yielding an oil. The oil was dissolved in 50 mL of ethanol and 15 mL of water, treated with LiOH until the pH was 12, and stirred at room temperature overnight. The reaction was concentrated in vacuo, diluted with water, acidified with dil HCl, and extracted with ethyl acetate. The ethyl acetate phase was dried over anhydrous $MgSO_4$, filtered and concentrated yielding [[1-[4-(aminosulfonyl)phenyl]-5-(4-chlorophenyl)-1H-pyrazol-3-yl]acetic acid as a brown solid (1.072 g, 76%): mp 120–122° C. High resolution mass spectrum Calc'd. for $C_{17}H_{15}ClN_3O_4S$ (M+H): 392.0472. Found: 392.0467. $^1$h NMR ($CDCl_3$ and $CD_3CO_2D$) 7.84 (d, J=8.66 Hz 2 H), 7.37 (d, J=8.66 Hz, 2 H), 7.31 (d, J=8.66 Hz, 2 H), 7.15 (d, J=8.66 Hz, 2 H), 6.54 (s, 1H), 3.84 (s, 2H).

Step 4. Preparation of [[1-[4-(aminosulfonyl)phenyl]-5-(4-chlorophenyl)-1H-pyrazol-3-yl]-N-hydroxy-N-methylacetamide.

To a stirred solution of the 1-(4-aminosulfonylphenyl)-4-(4-chlorophenyl)pyrazole-3-acetic acid from step 3 (0.240 g, 0.613 mmol) in dioxane (6 mL) was added N-hydroxysuccinimide (0.085 g, 0.735 mmol) and 1-(3-dimethylaminopropyl)-3-ethylcarbodiimide hydrochloride (EDC) (0.129 g, 0.674 mmol). After stirring overnight, the reaction mixture was concentrated in vacuo and diluted with ethyl acetate. The ethyl acetate phase was washed with $KHSO_4$, $NaHCO_3$, and brine, dried over $MgSO_4$, filtered and concentrated in vacuo yielding the crude N-hydroxysuccinimide ester. This ester and N-methylhydroxylamide HCl (0.056 g, 0.674 mmol) were dissolved in dimethylformamide, (4 mL) and triethylamine (94 μL, 0.068 g, 0.674 mmol) was added. The reaction was stirred at room temperature for 56 hours, diluted with ethyl acetate, washed with KHSO$_4$, dried over anhydrous MgSO$_4$, filtered and concentrated in vacuo yielding a semi-solid. This solid was treated with isooctane and ethyl acetate yielding [[1-[4-(aminosulfonyl)phenyl]-5-(4-chlorophenyl)-1H-pyrazol-3-yl)-N-hydroxy-N-methyl acetamide as an off-white powder (0.083 g, 32%): mp 110–135° C. (dec). $^1$H NMR (CDCl$_3$ and DMSO d$_6$) 9.45 (s, 1 H exch), 7.86 (d, J=8.86 Hz, 2 H), 7.27–7.40 (m, 4 H), 7.12 (d, J=8.46 Hz, 2 H), 6.49, s, 1 H), 5.98 (s, 2H), 3.89 (s, 2 H), 3.25 (s, 3 H). LRMS: M$^+$ obs at 421.

EXAMPLE 4

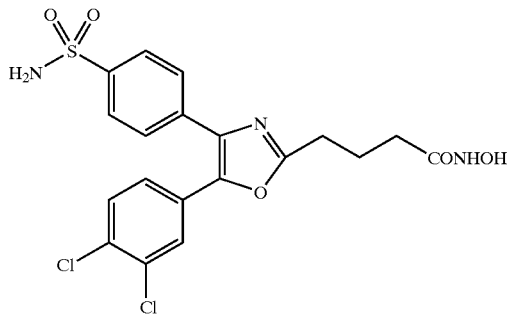

4-[(4-Aminosulfonyl)phenyl]-5-(3,4-dichlorophenyl)-N-hydroxy-2-oxazole-butanamide Step 1. Preparation of 2-(3,4-dichlorophenyl)-2-hydroxy-1-phenylethanone.

Trimethylsilyl cyanide (14.6 g, 0.147 mol) was dissolved in 30 mL of methylene chloride and added to a solution of 3,4-dichlorobenzaldehyde (25 g, 0.143 mol) and zinc iodide (0.41 g, 1.28 mmol) in 100 mL of methylene chloride. The reaction mixture was stirred at room temperature for 1 h and diluted with 200 mL of methylene chloride. The organic layer was washed with saturated sodium bicarbonate (2×150 mL), saturated brine (2×150 mL), dried over magnesium sulfate, filtered and concentrated to give 38.4 g (98%) of a brown oil, which was used in the next reaction without further purification. This trimethylsilyl cyanohydrin (15 g, 0.0547 mol) was dissolved in 20 mL of diethyl ether and added to phenylmagnesium bromide (19.5 mL of 3.0 M in ether solution, 0.0585 mol) in 250 mL of ether. The reaction mixture was stirred for 1.5 h at room temperature, then slowly quenched with 100 mL of 3 N HCl. The organic layer was separated and washed with saturated sodium bicarbonate (1×150 mL), saturated brine (1×150 mL), dried over magnesium sulfate, filtered and concentrated to give 13.0 g of a brown oil. A solution of 9:1 trifluoroacetic acid in water (50 mL) was added to the concentrated residue, and the mixture was stirred for 1.5 h at room temperature. The reaction mixture was neutralized by adding solid sodium carbonate. The resulting residue was partitioned between water (200 mL) and ethyl acetate (300 mL). The organic layer was separated and washed with saturated sodium bicarbonate (1×150 mL), saturated brine (1×150 mL), dried over magnesium sulfate, filtered and concentrated. The concentrated residue was crystallized from ethyl acetate and hexane to give 7.37 g (48%) of 2-(3,4-dichlorophenyl)-2-hydroxy-1-(phenyl)ethanone as a yellow solid: HRMS calcd. for C$_{14}$H$_{10}$O$_2$Cl$_2$ 281.0136, found 281.0112.

Step 2. Preparation of methyl [(4-phenyl)-5-(3,4-dichlorophenyl)oxazole]-2-butanoate.

5-(Methoxycarbonyl)pentanoyl chloride (2.82 g, 0.017 mol) and triethylamine (3.47 g, 0.034 mol) were added to a solution of 2-(3,4-dichlorophenyl)-2-hydroxy-1-[phenyl]ethanone (Step 1) (4.77 g, 0.017 mmol) in 40 mL of methylene chloride. The resulting mixture was stirred overnight at room temperature. The reaction mixture was diluted with 100 mL of methylene chloride. The organic solution was washed with water (1×100 mL), saturated brine (1×100 mL), dried over magnesium sulfate, filtered and concentrated. The concentrated residue was dried under high vacuum, then ammonium acetate (4.6 g, 0.06 mol) and 30 mL of acetic acid were added. The reaction mixture was heated at 100° C. for 2.5 h. The reaction mixture was cooled to room temperature, and the excess acetic acid was removed under vacuum. The resulting residue was partitioned between water (100 mL) and ethyl acetate (200 mL). The organic layer was separated, washed with saturated aqueous sodium bicarbonate (2×100 mL), saturated brine (1×100 mL), dried over magnesium sulfate, filtered and concentrated. The concentrated residue was purified by flash chromatography on silica gel (eluting with 1:9 ethyl acetate:hexane) to give 2.82 g (42.6%) of methyl [(4-phenyl)-5-(3,4-dichlorophenyl)oxazole]-2-butanoate as a yellow oil: HRMS calcd. for C$_{20}$H$_{17}$N$_1$O$_3$Cl$_2$ 390.0664. Found 390.0648.

Step 3. Preparation of methyl 4-[(4-aminosulfonyl)phenyl]-5-(3,4-dichloro-phenyl)oxazole-2-butanoate.

Chlorosulfonic acid (28 g, 0.24 mol) was added to methyl ((4-phenyl)-5-(3,4-dichlorophenyl)oxazole]-2-butanoate (Step 2) (3.74 g, 9.58 mmol) at 5° C. The ice bath was removed, and the reaction was stirred for 3 h at room temperature. The reaction mixture was diluted with 100 mL of methylene chloride and slowly poured into ice. The organic layer was separated and washed with saturated brine (1×100 mL). The organic layer was separated and poured into 50 mL of concentrated ammonium hydroxide. The reaction mixture was stirred for 30 minutes at room temperature. The organic layer was separated and washed with water (1×100 mL), saturated brine (1×100 mL), dried over magnesium sulfate, filtered and concentrated. The crude ester was crystallized from methanol and water to give 1.7 g (38%) of methyl 4-[(4-aminosulfonyl)phenyl]-5-(3,4-dichloro-phenyl)oxazole-2-butanoate as a yellow solid: m.p. 130.7–131.8° C. HRMS calcd. for C$_{20}$H$_{18}$N$_2$O$_5$SCl$_2$ 469.0392. Found 469.0413.

Step 4. Preparation of 4-[(4-aminosulfonyl)phenyl]-5-(3,4-dichlorophenyl)-N-hydroxy-2-oxazolebutanamide.

An aqueous solution of 50% N-hydroxylamine (1 g) was added to methyl 4-[(4-aminosulfonyl)phenyl]-5-(3,4-dichlorophenyl)oxazole-2-butanoate (Step 3) (0.3 g, 0.64 mmol) in 10 mL of THF:methanol (1:1). The resulting solution was stirred for 18 h at room temperature. An additional amount of aqueous 50% N-hydroxylamine (2.7 g) was added, and the resulting solution was stirred for 48 h at room temperature. The solvents were removed under vacuum. Water (50 mL) and ethyl acetate (50 mL) were added to the concentrated residue. The resulting solid was collected by filtration, washed with water and ether, and air-dried to give 0.14 g (46.5%) of 4-[(4-aminosulfonyl)phenyl]-5-(3,4-dichlorophenyl)-N-hydroxy-2-oxazolebutanamide as a white solid: m.p. 165.0–169.7° C. $^1$H NMR (CD$_3$OD/300 MHz) δ 2.15–2.27 (m, 4H), 2.94 (t, 2H, J=7.05 Hz), 7.44–7.48 (m, 1H), 7.56–7.58 (m, 1H), 7.72-7.78 (m, 3H), 7.94–7.96 (m, 2H). HRMS: calcd for C$_{19}$H$_{17}$N$_3$O$_5$SCl$_2$ 470.0344. Found 470.0340.

Biological Evaluation

Rat Carrageenan Foot Pad Edema Test

The carrageenan foot pad edema test was performed with materials, reagents and procedures essentially as described by Winter, et al., (*Proc. Soc. Exp. Biol. Med.*, 111, 544 (1962)). Male Sprague-Dawley rats were selected in each group so that the average body weight was as close as possible. Rats were fasted with free access to water for over sixteen hours prior to the test. The rats were dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Otterness and Bliven, *Laboratory Models for Testing NSAIDs*, in *Non-steroidal Anti-Inflammatory Drugs*, (J. Lombardino, ed. 1985)). The % inhibition shows the % decrease from control paw volume determined in this procedure and the data for selected compounds in this invention are summarized in Table I.

TABLE I

RAT PAW EDEMA

| Example | % Inhibition @ 10 mg/kg body weight |
|---|---|
| 2 | 2 |

Evaluation of COX-1 and COX-2 Activity In Vitro

The compounds of this invention exhibited inhibition in vitro of COX-2. The COX-2 inhibition activity of the compounds of this invention illustrated in the Examples was determined by the following methods.

a. Preparation of Recombinant COX Baculoviruses

Recombinant COX-1 and COX-2 were prepared as described by Gierse et al, [*J. Biochem.*, 305, 479–84 (1995)]. A 2.0 kb fragment containing the coding region of either human or murine COX-1 or human or murine COX-2 was cloned into a BamH1 site of the baculovirus transfer vector pVL1393 (Invitrogen) to generate the baculovirus transfer vectors for COX-1 and COX-2 in a manner similar to the method of D. R. O'Reilly et al (*Baculovirus Expression Vectors: A Laboratory Manual* (1992)). Recombinant baculoviruses were isolated by transfecting 4 µg of baculovirus transfer vector DNA into SF9 insect cells ($2\times10^8$) along with 200 ng of linearized baculovirus plasmid DNA by the calcium phosphate method. See M. D. Summers and G. E. Smith, *A Manual of Methods for Baculovirus Vectors and Insect Cell Culture Procedures*, Texas Agric. Exp. Station Bull. 1555 (1987). Recombinant viruses were purified by three rounds of plaque purification and high titer ($10^{7-10^8}$ pfu/ml) stocks of virus were prepared. For large scale production, SF9 insect cells were infected in 10 liter fermentors ($0.5\times10^6$/ml) with the recombinant baculovirus stock such that the multiplicity of infection was 0.1. After 72 hours the cells were centrifuged and the cell pellet homogenized in Tris/Sucrose (50 mM: 25%, pH 8.0) containing 1% 3-((3-cholamidopropyl)dimethylammonio]-1-propanesulfonate (CHAPS). The homogenate was centrifuged at 10,000×G for 30 minutes, and the resultant supernatant was stored at −80° C. before being assayed for COX activity.

b. Assay for COX-1 and COX-2 Activity

COX activity was assayed as $PGE_2$ formed/µg protein/time using an ELISA to detect the prostaglandin released. CHAPS-solubilized insect cell membranes containing the appropriate COX enzyme were incubated in a potassium phosphate buffer (50 mm, pH 8.0) containing epinephrine, phenol, and heme with the addition of arachidonic acid (10 µM). Compounds were pre-incubated with the enzyme for 10–20 minutes prior to the addition of arachidonic acid. Any reaction between the arachidonic acid and the enzyme was stopped after ten minutes at 37° C./room temperature by transferring 40 µl of reaction mix into 160 µl ELISA buffer and 25 µM indomethacin. The $PGE_2$ formed was measured by standard ELISA technology (Cayman Chemical). Results are shown in Table II.

Assay for 5-Lipoxygenase Activity

The 5-lipoxygenase (5-LO) activity of the compounds were determined by the calcium ionophore-induced Leukotriene B4 (LTB4) production in human whole blood. Venous blood was collected from healthy human donors using heparin as an anti-coagulant. Human blood samples (0.2 ml of a 1:4 dilution in RPMI 1640 medium) were incubated in 96-well culture plates for 15 minutes at 37° C. with test compounds dissolved in ethanol (EtOH; final concentration<1%), or vehicle. Typically 7 concentrations of test compounds were examined in duplicate. A-23187 [Sigma] was added to the blood to a final concentration of 20 µg/ml, and the mixtures were incubated for 10 minutes at 37° C. The reaction was stopped by placing the samples on ice. The samples were then centrifuged at 800×g at 4° C. for 10 minutes to pellet the cells, and the supernatants were recovered for quantitation of LTB4 by ELISA (Cayman Chemical Co.; sensitivity 3 pg/ml). $IC_{50}$'s were estimated from a four parameter logistic model with two parameters fixed, the minimum (0% inhibition) and maximum (100% inhibition). The $IC_{50}$ value is the concentration that produces 50% inhibition between the fixed values of the minimum and maximum. Data is reported as the mean $IC_{50}$ for each compound. Results are shown in Table II.

TABLE II

| Example | COX-2 $IC_{50}$ (µM) | COX-1 $IC_{50}$ (µM) | 5-LO $IC_{50}$ (µM) |
|---|---|---|---|
| 1 | 6.6 | 53.5 | 12.3 |
| 2 | 5.1 | >100 | 0.05 |
| 4 | 0.3 | 12.5 | |

Also embraced within this invention is a class of pharmaceutical compositions comprising the active compounds of this combination therapy in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The active compounds and composition may, for example, be administered orally, intravascularly (IV), intraperitoneally, subcutaneously, intramuscularly (IM) or topically.

For oral administration, the pharmaceutical composition may be in the form of, for example, a tablet, hard or soft capsule, lozenges, dispensable powders, suspension or liquid. The pharmaceutical composition is preferably made in the form of a dosage unit containing a particular amount of the active ingredient. Examples of such dosage units are tablets or capsules.

The active ingredient may also be administered by injection (IV, IM, subcutaneous or jet) as a composition wherein, for example, saline, dextrose, or water may be used as a suitable carrier. The pH of the composition may be adjusted, if necessary, with suitable acid, base, or buffer. Suitable bulking, dispersing, wetting or suspending agents, including mannitol and PEG 400, may also be included in the composition. A suitable parenteral composition can also include a compound formulated as a sterile solid substance, including lyophilized powder, in injection vials. Aqueous solution can be added to dissolve the compound prior to injection.

The amount of therapeutically active compounds that are administered and the dosage regimen for treating a disease condition with the compounds and/or compositions of this invention depends on a variety of factors, including the age, weight, sex and medical condition of the subject, the severity of the inflammation or inflammation related disorder, the route and frequency of administration, and the particular compound employed, and thus may vary widely. The pro-drug compositions should include similar dosages as for the parent compounds. The pharmaceutical compositions may contain active ingredients in the range of about 0.1 to 1000 mg, preferably in the range of about 0.5 to 250 mg and most preferably between about 1 and 60 mg. A daily dose of about 0.01 to 100 mg/kg body weight, preferably between about 0.05 and about 20 mg/kg body weight and most preferably between about 0.1 to 10 mg/kg body weight, may be appropriate. The daily dose can be administered in one to four doses per day.

In the case of skin conditions, it may be preferable to apply a topical preparation of compounds of this invention to the affected area two to four times a day.

For disorders of the eye or other external tissues, e.g., mouth and skin, the formulations are preferably applied as a topical gel, spray, ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiinflammatory active ingredients are preferably present in such formulations in a concentration of 0.5 to 20%, advantageously 0.5 to 10% and particularly about 1.5% w/w.

For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-releaseformulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound of Formula I

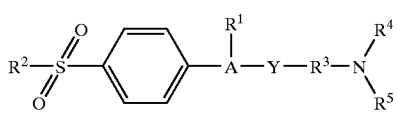

wherein A is a oxazolyl and is optionally substituted with a substituent selected from acyl, halo, alkyl, haloalkyl, cyano, nitro, carboxyl, alkoxy, oxo, aminocarbonyl, alkoxycarbonyl, and cycloalkyl;

wherein Y is one or more radicals selected from alkyl, alkynyl, alkenyl, hydroxyalkyl, aminoalkyl, alkylaminoalkyl, arylaminoalkyl, acyl, aryl, aralkyl, cycloalkyl, cycloalkylalkyl, and heterocycloalkyl;

wherein $R^1$ is one or more substituents selected from heterocyclo, cycloalkyl, cycloalkenyl and aryl, wherein $R^1$ is optionally substituted at a substitutable position with one or more substituents selected from alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy and alkylthio;

wherein $R^2$ is selected from alkyl and amino;

wherein $R^3$ is a direct bond or a radical selected from

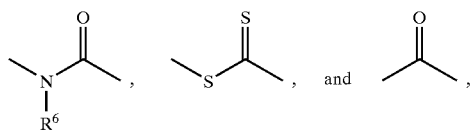

wherein $R^4$ is selected from hydroxyl, alkyl, aryl, and cycloalkyl;

wherein $R^5$ is selected from hydrogen, alkyl, aryl, and cycloalkyl; and wherein $R^6$ is selected from hydrogen and hydroxyl;

or a pharmaceutically-acceptable salt thereof.

2. The compound of claim 1 wherein A is optionally substituted with a substituent selected from acyl, halo, lower alkyl, lower haloalkyl, oxo, cyano, nitro, carboxyl, lower alkoxy, aminocarbonyl, lower alkoxycarbonyl, lower carboxyalkyl, lower cyanoalkyl, and lower hydroxyalkyl; wherein Y is a radical selected from lower alkyl, lower alkynyl, lower alkenyl, lower hydroxyalkyl, lower aminoalkyl, lower alkylaminoalkyl, lower arylaminoalkyl, lower acyl, aryl, lower aralkyl, lower cycloalkyl, lower cycloalkylalkyl; wherein $R^1$ is one or more substituents selected from lower cycloalkyl, lower cycloalkenyl and aryl selected from phenyl, biphenyl and naphthyl, wherein $R^1$ is optionally substituted at a substitutable position with one or more substituents selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, halo, lower alkoxy and lower alkylthio; wherein $R^2$ is selected from lower alkyl and amino; wherein $R^4$ is selected from hydroxyl, lower alkyl, phenyl, and lower cycloalkyl; and wherein $R^5$ is selected from hydrogen, lower alkyl, phenyl, and lower cycloalkyl; or a pharmaceutically-acceptable salt thereof.

3. The compound of claim 2 wherein A is optionally substituted with a substituent selected from formyl, fluoro, chloro, bromo, methyl, trifluoromethyl, oxo, cyano, carboxyl, methoxy, aminocarbonyl, methoxycarbonyl, ethoxycarbonyl, acetyl, carboxypropyl, and hydroxymethyl; wherein Y is a radical selected from ethyl, propyl, isopropyl, butyl, 1-propynyl, 2-propynyl, 1-butyn-3-yl, 1-propenyl, 2-propenyl, acetyl, dihydroxypropyl, hydroxyethyl, 1-amino-ethyl, 1-aminopropyl, 1-(N-methylamino)propyl, 1-(N,N-dimethylamino)propyl, 1-(N-phenylamino)propyl, benzyl, phenylethyl, cyclohexylmethyl, cyclopentylethyl, and phenyl optionally substituted at a substitutable position with one or more substituents selected from fluoro, chloro, bromo, hydroxyl, methyl, and methoxy; wherein $R^1$ is a substituent selected from phenyl, wherein $R^1$ is optionally substituted at a substitutable position with one or more substituents selected from methyl, trifluoromethyl, hydroxyl, hydroxymethyl, trifluoromethoxy, nitro, methoxymethyl, fluoro, chloro, bromo, methoxy and methylthio; wherein $R^2$ is methyl or amino; wherein $R^4$ is selected from hydroxyl, methyl, and phenyl; and wherein $R^5$ is selected from hydrogen, methyl and phenyl; or a pharmaceutically-acceptable salt thereof.

4. The compound of claim 3 selected from compounds and their pharmaceutically-acceptable salts, of the group consisting of

[4-[(4-aminosulfonyl)phenyl]-5-phenyl-2-oxazolyl] methyl-N-hydroxy-N-methyl-dithiocarbamate;

[4-[(4-aminosulfonyl)phenyl]-5-(4-chlorophenyl)-2-oxazolyl]methyl-N-hydroxy-N-methyl-dithiocarbamate;

[5-[(4-aminosulfonyl)phenyl]-4-phenyl-2-oxazolyl] methyl-N-hydroxy-N-methyl-dithiocarbamate;

[5-[(4-aminosulfonyl)phenyl]-4-(4-chlorophenyl)-2-oxazolyl]methyl-N-hydroxy-N-methyl-dithiocarbamate;

[5-[(4-aminosulfonyl)phenyl]-4-(4-fluorophenyl)-2-oxazolyl]methyl-N-hydroxy-N-methyl-dithiocarbamate;

[5-[(4-aminosulfonyl)phenyl]-4-(4-methoxyphenyl)-2-oxazolyl]methyl-N-hydroxy-N-methyl-dithiocarbamate;

[5-[(4-aminosulfonyl)phenyl]-4-(3-chloro-4-methoxyphenyl)-2-oxazolyl]methyl-N-hydroxy-N-methyl-dithiocarbamate;

[5-[(4-aminosulfonyl)phenyl]-4-(3-fluoro-4-methoxyphenyl)-2-oxazolyl]methyl-N-hydroxy-N-methyl-dithiocarbamate;

[5-[(4-aminosulfonyl)phenyl]-4-(3-chloro-4-fluorophenyl)-2-oxazolyl]methyl-N-hydroxy-N-methyl-dithiocarbamate;

[4-[(4-methylsulfonyl)phenyl]-5-phenyl-2-oxazolyl] methyl-N-hydroxy-N-methyl-dithiocarbamate;

[5-(4-chlorophenyl)-4-[(4-methylsulfonyl)phenyl]-2-oxazolyl]methyl-N-hydroxy-N-methyl-dithiocarbamate;

[5-[(4-methylsulfonyl)phenyl]-4-phenyl-2-oxazolyl] methyl-N-hydroxy-N-methyl-dithiocarbamate;

[4-(4-chlorophenyl)-5-[(4-methylsulfonyl)phenyl]-2-oxazolyl]methyl-N-hydroxy-N-methyl-dithiocarbamate;

[4-[(4-aminosulfonyl)phenyl]-5-phenyl-2-oxazolyl]-1-propyl-N-hydroxy-N-methyl-dithiocarbamate;

[4-[(4-aminosulfonyl)phenyl]-5-(4-chlorophenyl)-2-oxazolyl]-1-propyl-N-hydroxy-N-methyl-dithiocarbamate;

[5-(4-aminosulfonyl)phenyl]-4-phenyl-2-oxazolyl]-1-propyl-N-hydroxy-N-methyl-dithiocarbamate;
[5-[(4-aminosulfonyl)phenyl]-4-(4-chlorophenyl)-2-oxazolyl]-1-propyl-N-hydroxy-N-methyl-dithiocarbamate;
[5-[(4-aminosulfonyl)phenyl]-4-(4-fluorophenyl)-2-oxazolyl]-1-propyl-N-hydroxy-N-methyl-dithiocarbamate;
[5-[(4-aminosulfonyl)phenyl]-4-(4-methoxyphenyl)-2-oxazolyl]-1-propyl-N-hydroxy-N-methyl-dithiocarbamate;
[5-[(4-aminosulfonyl)phenyl]-4-(3-chloro-4-methoxyphenyl)-2-oxazolyl]-1-propyl-N-hydroxy-N-methyl-dithiocarbamate;
[5-[(4-aminosulfonyl)phenyl]-4-(3-fluoro-4-methoxyphenyl)-2-oxazolyl]-1-propyl-N-hydroxy-N-methyl-dithiocarbamate;
[5-(4-aminosulfonyl)phenyl]-4-(3-chloro-4-fluorophenyl)-2-oxazolyl]-1-propyl-N-hydroxy-N-methyl-dithiocarbamate;
[4-[(4-methylsulfonyl)phenyl]-4-phenyl-2-oxazolyl]-1-propyl-N-hydroxy-N-methyl-dithiocarbamate;
[5-(4-chlorophenyl)-4-[(4-methylsulfonyl)phenyl]-2-oxazolyl]-1-propyl-N-hydroxy-N-methyl-dithiocarbamate;
[5-[(4-methylsulfonyl)phenyl]-4-phenyl-2-oxazolyl]-1-propyl-N-hydroxy-N-methyl-dithiocarbamate;
[4-(4-chlorophenyl)-5-[(4-methylsulfonyl)phenyl]-2-oxazolyl]-1-propyl-N-hydroxy-N-methyl-dithiocarbamate;
[3-[4-[(4-aminosulfonyl)phenyl]-5-phenyl-2-oxazolyl]-2-propenyl-N-hydroxy-N-methyl-dithiocarbamate;
[3-[4-[(4-aminosulfonyl)phenyl]-5-(4-chlorophenyl)-2-oxazolyl]-2-propenyl-N-hydroxy-N-methyl-dithiocarbamate;
[1-[5-[(4-aminosulfonyl)phenyl]-4-phenyl-2-oxazolyl]-2-propenyl-N-hydroxy-N-methyl-dithiocarbamate;
[3-[5-[(4-aminosulfonyl)phenyl]-4-(4-chlorophenyl)-2-oxazolyl]-2-propenyl-N-hydroxy-N-methyl-dithiocarbamate;
[3-[5-[(4-aminosulfonyl)phenyl]-4-(4-fluorophenyl)-2-oxazolyl]-2-propenyl-N-hydroxy-N-methyl-dithiocarbamate;
[3-[5-[(4-aminosulfonyl)phenyl]-4-(4-methoxyphenyl)-2-oxazolyl]-2-propenyl-N-hydroxy-N-methyl-dithiocarbamate;
[3-[5-[(4-aminosulfonyl)phenyl]-4-(3-chloro-4-methoxyphenyl)-2-oxazolyl]-2-propenyl-N-hydroxy-N-methyl-dithiocarbamate;
[3-[5-[(4-aminosulfonyl)phenyl]-4-(3-fluoro-4-methoxyphenyl)-2-oxazolyl]-2-propenyl-N-hydroxy-N-methyl-dithiocarbamate;
[3-[5-[(4-aminosulfonyl)phenyl]-4-(3-chloro-4-fluorophenyl)-2-oxazolyl]-2-propenyl-N-hydroxy-N-methyl-dithiocarbamate;
[3-[4-[(4-methylsulfonyl)phenyl]-5-phenyl-2-oxazolyl]-2-propenyl-N-hydroxy-N-methyl-dithiocarbamate;
[3-[5-(4-chlorophenyl)-4-[(4-methylsulfonyl)phenyl]-2-oxazolyl]-2-propenyl-N-hydroxy-N-methyl-dithiocarbamate;
[3-[5-[(4-methylsulfonyl)phenyl]-4-phenyl-2-oxazolyl]-2-propenyl-N-hydroxy-N-methyl-dithiocarbamate;
[3-[4-(4-chlorophenyl)-5-[(4-methylsulfonyl)phenyl]-2-oxazolyl]-2-propenyl-N-hydroxy-N-methyl-dithiocarbamate;

[3-[4-[(4-aminosulfonyl)phenyl]-5-phenyl-2-oxazolyl]-2-propynyl-N-hydroxy-N-methyl-dithiocarbamate;
[3-[4-[(4-aminosulfonyl)phenyl]-5-(4-chlorophenyl)-2-oxazolyl]-2-propynyl-N-hydroxy-N-methyl-dithiocarbamate;
[3-[5-[(4-aminosulfonyl)phenyl]-4-phenyl-2-oxazolyl]-2-propynyl-N-hydroxy-N-methyl-dithiocarbamate;
[3-[5-[(4-aminosulfonyl)phenyl]-4-(4-chlorophenyl)-2-oxazolyl]-2-propynyl-N-hydroxy-N-methyl-dithiocarbamate;
[3-[5-[(4-aminosulfonyl)phenyl]-4-(4-fluorophenyl)-2-oxazolyl]-2-propynyl-N-hydroxy-N-methyl-dithiocarbamate;
[3-[5-[(4-aminosulfonyl)phenyl]-4-(4-methoxyphenyl)-2-oxazolyl]-2-propynyl-N-hydroxy-N-methyl-dithiocarbamate;
[3-[5-[(4-aminosulfonyl)phenyl]-4-(3-chloro-4-methoxyphenyl)-2-oxazolyl]-2-propynyl-N-hydroxy-N-methyl-dithiocarbamate;
[3-[5-[(4-aminosulfonyl)phenyl]-4-(3-fluoro-4-methoxyphenyl)-2-oxazolyl]-2-propynyl-N-hydroxy-N-methyl-dithiocarbamate;
[3-[5-[(4-aminosulfonyl)phenyl]-4-(3-chloro-4-fluorophenyl)-2-oxazolyl]-2-propynyl-N-hydroxy-N-methyl-dithiocarbamate;
[3-[4-[(4-methylsulfonyl)phenyl]-5-phenyl-2-oxazolyl]-2-propynyl-N-hydroxy-N-methyl-dithiocarbamate;
[3-[5-(4-chlorophenyl)-4-[(4-methylsulfonyl)phenyl]-2-oxazolyl]-2-propynyl-N-hydroxy-N-methyl-dithiocarbamate;
[3-[5-[(4-methylsulfonyl)phenyl]-4-phenyl-2-oxazolyl]-2-propynyl-N-hydroxy-N-methyl-dithiocarbamate;
[3-[4-(4-chlorophenyl)-5-[(4-methylsulfonyl)phenyl]-2-oxazolyl]-2-propynyl-N-hydroxy-N-methyl-dithiocarbamate;
3-[[4-[(4-aminosulfonyl)phenyl]-5-phenyl-2-oxazolyl]-1-methyl-2-propenyl]-N-hydroxy-N-methyl-dithiocarbamate;
3-[[4-[(4-aminosulfonyl)phenyl]-5-(4-chlorophenyl)-2-oxazolyl]-1-methyl-2-propenyl]-N-hydroxy-N-methyl-dithiocarbamate;
3-[[5-[(4-aminosulfonyl)phenyl]-4-phenyl-2-oxazolyl]-1-methyl-2-propenyl]-N-hydroxy-N-methyl-dithiocarbamate;
3-[[5-[(4-aminosulfonyl)phenyl]-4-(4-chlorophenyl)-2-oxazolyl]-1-methyl-2-propenyl]-N-hydroxy-N-methyl-dithiocarbamate;
3-[[5-[(4-aminosulfonyl)phenyl]-4-(4-fluorophenyl)-2-oxazolyl]-1-methyl-2-propenyl]-N-hydroxy-N-methyl-dithiocarbamate;
3-[[5-[(4-aminosulfonyl)phenyl]-4-(4-methoxyphenyl)-2-oxazolyl]-1-methyl-2-propenyl]-N-hydroxy-N-methyl-dithiocarbamate;
3-[[5-[(4-aminosulfonyl)phenyl]-4-(3-chloro-4-methoxyphenyl)-2-oxazolyl]-1-methyl-2-propenyl]-N-hydroxy-N-methyl-dithiocarbamate;
3-[[5-[(4-aminosulfonyl)phenyl]-4-(3-fluoro-4-methoxyphenyl)-2-oxazolyl]-1-methyl-2-propenyl]-N-hydroxy-N-methyl-dithiocarbamate;
3-[[5-[(4-aminosulfonyl)phenyl]-4-(3-chloro-4-fluorophenyl)-2-oxazolyl]-1-methyl-2-propenyl]-N-hydroxy-N-methyl-dithiocarbamate;
3-[[4-[(4-methylsulfonyl)phenyl]-4-phenyl-2-oxazolyl]-1-methyl-2-propenyl]-N-hydroxy-N-methyl-dithiocarbamate;

3-[[5-(4-chlorophenyl)-4-[(4-methylsulfonyl)phenyl]-2-oxazolyl]-1-methyl-2-propenyl]-N-hydroxy-N-methyl-dithiocarbamate;

3-[[5-[(4-methylsulfonyl)phenyl]-4-phenyl-2-oxazolyl]-1-methyl-2-propenyl]-N-hydroxy-N-methyl-dithiocarbamate;

3-[[4-(4-chlorophenyl)-5-[(4-methylsulfonyl)phenyl]-2-oxazolyl]-1-methyl-2-propenyl]-N-hydroxy-N-methyl-dithiocarbamate;

3-[4-[(4-aminosulfonyl)phenyl]-5-phenyl-2-oxazolyl]phenyl-N-hydroxy-N-methyl-dithiocarbamate;

3-[4-[(4-aminosulfonyl)phenyl]-5-(4-chlorophenyl)-2-oxazolyl]phenyl-N-hydroxy-N-methyl-dithiocarbamate;

3-[5-[(4-aminosulfonyl)phenyl]-4-phenyl-2-oxazolyl]phenyl-N-hydroxy-N-methyl-dithiocarbamate;

4-[5-[(4-aminosulfonyl)phenyl]-4-(4-chlorophenyl)-2-oxazolyl]phenyl-N-hydroxy-N-methyl-dithiocarbamate;

4-[5-[(4-aminosulfonyl)phenyl]-4-(4-fluorophenyl)-2-oxazolyl]phenyl-N-hydroxy-N-methyl-dithiocarbamate;

4-[5-[(4-aminosulfonyl)phenyl]-4-(4-methoxyphenyl)-2-oxazolyl]phenyl-N-hydroxy-N-methyl-dithiocarbamate;

4-[5-[(4-aminosulfonyl)phenyl]-4-(3-chloro-4-methoxyphenyl)-2-oxazolyl]phenyl-N-hydroxy-N-methyl-dithiocarbamate;

4-[5-[(4-aminosulfonyl)phenyl]-4-(3-fluoro-4-methoxyphenyl)-2-oxazolyl]phenyl-N-hydroxy-N-methyl-dithiocarbamate;

4-[5-[(4-aminosulfonyl)phenyl]-4-(3-chloro-4-fluorophenyl)-2-oxazolyl]phenyl-N-hydroxy-N-methyl-dithiocarbamate;

4-[4-[(4-methylsulfonyl)phenyl]-5-phenyl-2-oxazolyl]phenyl-N-hydroxy-N-methyl-dithiocarbamate;

4-[5-(4-chlorophenyl)-4-[(4-methylsulfonyl)phenyl]-2-oxazolyl]phenyl-N-hydroxy-N-methyl-dithiocarbamate;

3-[5-[(4-methylsulfonyl)phenyl]-4-phenyl-2-oxazolyl]phenyl-N-hydroxy-N-methyl-dithiocarbamate;

3-[4-(4-chlorophenyl)-5-[(4-methylsulfonyl)phenyl]-2-oxazolyl]phenyl-N-hydroxy-N-methyl-dithiocarbamate;

3-[4-[(4-aminosulfonyl)phenyl]-5-phenyl-2-oxazolyl]cyclohexyl-N-hydroxy-N-methyl-dithiocarbamate;

3-[4-[(4-aminosulfonyl)phenyl]-5-(4-chlorophenyl)-2-oxazolyl]cyclohexyl-N-hydroxy-N-methyl-dithiocarbamate;

3-[5-[(4-aminosulfonyl)phenyl]-4-phenyl-2-oxazolyl]cyclohexyl-N-hydroxy-N-methyl-dithiocarbamate;

4-[5-[(4-aminosulfonyl)phenyl]-4-(4-chlorophenyl)-2-oxazolyl]cyclohexyl-N-hydroxy-N-methyl-dithiocarbamate;

4-[5-[(4-aminosulfonyl)phenyl]-4-(4-fluorophenyl)-2-oxazolyl]cyclohexyl-N-hydroxy-N-methyl-dithiocarbamate;

4-[5-[(4-aminosulfonyl)phenyl]-4-(4-methoxyphenyl)-2-oxazolyl]cyclohexyl-N-hydroxy-N-methyl-dithiocarbamate;

4-[5-[(4-aminosulfonyl)phenyl]-4-(3-chloro-4-methoxyphenyl)-2-oxazolyl]cyclohexyl-N-hydroxy-N-methyl-dithiocarbamate;

4-[5-[(4-aminosulfonyl)phenyl]-4-(3-fluoro-4-methoxyphenyl)-2-oxazolyl]cyclohexyl-N-hydroxy-N-methyl-dithiocarbamate;

4-[5-[(4-aminosulfonyl)phenyl]-4-(3-chloro-4-fluorophenyl)-2-oxazolyl]cyclohexyl-N-hydroxy-N-methyl-dithiocarbamate;

4-[4-[(4-methylsulfonyl)phenyl]-5-cyclohexyl-2-oxazolyl]cyclohexyl-N-hydroxy-N-methyl-dithiocarbamate;

4-[5-(4-chlorophenyl)-4-[(4-methylsulfonyl)phenyl]-2-oxazolyl]cyclohexyl-N-hydroxy-N-methyl-dithiocarbamate;

3-[5-[(4-methylsulfonyl)phenyl]-4-cyclohexenyl-2-oxazolyl]cyclohexyl-N-hydroxy-N-methyl-dithiocarbamate;

3-[4-(4-chlorophenyl)-5-[(4-methylsulfonyl)phenyl-2-oxazolyl]cyclohexyl-N-hydroxy-N-methyl-dithiocarbamate;

4-[(4-aminosulfonyl)phenyl]-5-(3,4-dichlorophenyl)-N-hydroxy-2-oxazolebutanamide;

4-[(4-aminosulfonyl)phenyl]-N-hydroxy-N-methyl-5-phenyl-2-oxazolebutanamide;

4-[(4-aminosulfonyl)phenyl]-5-(4-chlorophenyl)-N-hydroxy-2-oxazolebutanamide;

5-[(4-aminosulfonyl)phenyl]-N-hydroxy-N-methyl-4-phenyl-2-oxazolebutanamide;

5-[(4-aminosulfonyl)phenyl]-4-(4-chlorophenyl)-N-hydroxy-2-oxazolebutanamide;

5-[(4-aminosulfonyl)phenyl]-4-(4-fluorophenyl)-N-hydroxy-N-methyl-2-oxazolebutanamide;

5-[(4-aminosulfonyl)phenyl]-4-(4-methoxyphenyl)-N-hydroxy-2-oxazolebutanamide;

5-[(4-aminosulfonyl)phenyl]-4-(3-chloro-4-methoxyphenyl)-N-hydroxy-2-oxazolebutanamide;

5-[(4-aminosulfonyl)phenyl]-4-(3-fluoro-4-methoxyphenyl)-N-hydroxy-N-methyl-2-oxazolebutanamide;

5-[(4-aminosulfonyl)phenyl]-4-(3-chloro-4-fluorophenyl)-N-hydroxy-2-oxazolebutanamide;

N-hydroxy-N-methyl-4-[(4-methylsulfonyl)phenyl]-5-phenyl-2-oxazolebutanamide;

5-(4-chlorophenyl)-N-hydroxy-N-methyl-4-[(4-methylsulfonyl)phenyl]-2-oxazolebutanamide;

5-[(4-methylsulfonyl)phenyl]-N-hydroxy-N-methyl-4-phenyl-2-oxazolebutanamide;

5-[(4-aminosulfonyl)phenyl]-4-(3-chloro-4-methoxyphenyl)-N-hydroxy-2-oxazolebutanamide;

4-(4-chlorophenyl)-5-[(4-methylsulfonyl)phenyl]-N-hydroxy-2-oxazolebutanamide;

4-[(4-aminosulfonyl)phenyl]-N-hydroxy-N-methyl-5-phenyl-2-oxazolepropanamide;

4-[(4-aminosulfonyl)phenyl]-5-(4-chlorophenyl)-N-hydroxy-N-methyl-2-oxazolepropanamide;

5-[(4-aminosulfonyl)phenyl]-N-hydroxy-N-methyl-4-phenyl-2-oxazolepropanamide;

5-[(4-aminosulfonyl)phenyl]-4-(4-chlorophenyl)-N-hydroxy-N-methyl-2-oxazolepropanamide;

5-[(4-aminosulfonyl)phenyl]-4-(4-fluorophenyl)-N-hydroxy-N-methyl-2-oxazolepropanamide;

5-[(4-aminosulfonyl)phenyl]-4-(4-methoxyphenyl)-N-hydroxy-N-methyl-2-oxazolepropanamide;

5-[(4-aminosulfonyl)phenyl]-4-(3-chloro-4-methoxyphenyl)-N-hydroxy-N-methyl-2-oxazolepropanamide;

5-[(4-aminosulfonyl)phenyl]-4-(3-fluoro-4-methoxyphenyl)-N-hydroxy-N-methyl-2-oxazolepropanamide;

5-[(4-aminosulfonyl)phenyl]-4-(3-chloro-4-fluorophenyl)-N-hydroxy-N-methyl-2-oxazolepropanamide;

N-hydroxy-N-methyl-4-[(4-methylsulfonyl)phenyl]-5-phenyl-2-oxazolepropanamide;

5-(4-chlorophenyl)-N-hydroxy-N-methyl-4-[(4-methylsulfonyl)phenyl]-2-oxazolepropanamide;

5-[(4-methylsulfonyl)phenyl]-N-hydroxy-N-methyl-4-phenyl-2-oxazolepropanamide;

4-(4-chlorophenyl)-5-[(4-methylsulfonyl)phenyl]-N-hydroxy-N-methyl-2-oxazolepropanamide;

4-[(4-aminosulfonyl)phenyl]-N-hydroxy-N-methyl-5-phenyl-2-oxazole-ethanamide;

4-[(4-aminosulfonyl)phenyl]-5-(4-chlorophenyl)-N-hydroxy-2-oxazole-ethanamide;

5-[(4-aminosulfonyl)phenyl]-N-hydroxy-N-methyl-4-phenyl-2-oxazole-ethanamide;

5-[(4-aminosulfonyl)phenyl]-4-(4-chlorophenyl)-N-hydroxy-2-oxazole-ethanamide;

5-[(4-aminosulfonyl)phenyl]-4-(4-fluorophenyl)-N-hydroxy-2-oxazole-ethanamide;

5-[(4-aminosulfonyl)phenyl]-4-(4-methoxyphenyl)-N-hydroxy-2-oxazole-ethanamide;

5-[(4-aminosulfonyl)phenyl]-4-(3-chloro-4-methoxyphenyl)-N-hydroxy-2-oxazole-ethanamide;

5-[(4-aminosulfonyl)phenyl]-4-(3-fluoro-4-methoxyphenyl)-N-hydroxy-2-oxazole-ethanamide;

5-[(4-aminosulfonyl)phenyl]-4-(3-chloro-4-fluorophenyl)-N-hydroxy-2-oxazole-ethanamide;

4-[(4-methylsulfonyl)phenyl]-N-hydroxy-N-methyl-5-phenyl-2-oxazole-ethanamide;

5-(4-chlorophenyl)-4-[(4-methylsulfonyl)phenyl]-N-hydroxy-N-methyl-2-oxazole-ethanamide;

5-[(4-methylsulfonyl)phenyl]-N-hydroxy-N-methyl-4-phenyl-2-oxazole-ethanamide;

4-(4-chlorophenyl)-5-[(4-methylsulfonyl)phenyl]-N-hydroxy-N-methyl-2-oxazole-ethanamide;

1-[4-[(4-aminosulfonyl)phenyl]-5-phenyl-2-oxazolyl]-N-hydroxy-N-methyl-2-propenamide;

1-[4-[(4-aminosulfonyl)phenyl]-5-(4-chlorophenyl)-2-oxazolyl]-N-hydroxy-N-methyl-2-propenamide;

1-[5-[(4-aminosulfonyl)phenyl]-4-phenyl-2-oxazolyl]-N-hydroxy-N-methyl-2-propenamide;

1-[5-[(4-aminosulfonyl)phenyl]-4-(4-chlorophenyl)-2-oxazolyl]-N-hydroxy-N-methyl-2-propenamide;

1-[5-[(4-aminosulfonyl)phenyl]-4-(4-fluorophenyl)-2-oxazolyl]-N-hydroxy-N-methyl-2-propenamide;

1-[5-[(4-aminosulfonyl)phenyl]-4-(4-methoxyphenyl)-2-oxazolyl]-N-hydroxy-N-methyl-2-propenamide;

1-[5-[(4-aminosulfonyl)phenyl]-4-(3-chloro-4-methoxyphenyl)-2-oxazolyl]-N-hydroxy-N-methyl-2-propenamide;

1-[5-[(4-aminosulfonyl)phenyl]-4-(3-fluoro-4-methoxyphenyl)-2-oxazolyl]-N-hydroxy-N-methyl-2-propenamide;

1-[5-[(4-aminosulfonyl)phenyl]-4-(3-chloro-4-fluorophenyl)-2-oxazolyl]-N-hydroxy-N-methyl-2-propenamide;

1-[4-(4-methylsulfonyl)phenyl]-5-phenyl-2-oxazolyl]-N-hydroxy-N-methyl-2-propenamide;

1-[5-(4-chlorophenyl)-4-[(4-methylsulfonyl)phenyl]-2-oxazolyl]-N-hydroxy-N-methyl-2-propenamide;

1-[5-[(4-methylsulfonyl)phenyl]-4-phenyl-2-oxazolyl]-N-hydroxy-N-methyl-2-propenamide;

1-[4-(4-chlorophenyl)-5-[(4-methylsulfonyl)phenyl]-2-oxazolyl]-N-hydroxy-N-methyl-2-propenamide;

1-[4-[(4-aminosulfonyl)phenyl]-5-phenyl-2-oxazolyl]-N-hydroxy-N-methyl-2-propynamide;

1-[4-[(4-aminosulfonyl)phenyl]-5-(4-chlorophenyl)-2-oxazolyl)-N-hydroxy-N-methyl-2-propynamide;

1-[5-[(4-aminosulfonyl)phenyl]-4-phenyl-2-oxazolyl]-N-hydroxy-N-methyl-2-propynamide;

1-[5-[(4-aminosulfonyl)phenyl]-4-(4-chlorophenyl)-2-oxazolyl]-N-hydroxy-N-methyl-2-propynamide;

1-[5-[(4-aminosulfonyl)phenyl)-4-(4-fluorophenyl)-2-oxazolyl]-N-hydroxy-N-methyl-2-propynamide;

1-[5-[(4-aminosulfonyl)phenyl]-4-(4-methoxyphenyl)-2-oxazolyl]-N-hydroxy-N-methyl-2-propynamide;

1-[5-[(4-aminosulfonyl)phenyl]-4-(3-chloro-4-methoxyphenyl)-2-oxazolyl]-N-hydroxy-N-methyl-2-propynamide;

1-[5-[(4-aminosulfonyl)phenyl]-4-(3-fluoro-4-methoxyphenyl)-2-oxazolyl]-N-hydroxy-N-methyl-2-propynamide;

1-[5-[(4-aminosulfonyl)phenyl]-4-(3-chloro-4-fluorophenyl)-2-oxazolyl]-N-hydroxy-N-methyl-2-propynamide;

1-[4-[(4-methylsulfonyl)phenyl]-5-phenyl-2-oxazolyl]-N-hydroxy-N-methyl-2-propynamide;

1-[5-(4-chlorophenyl)-4-[(4-methylsulfonyl)phenyl]-2-oxazolyl]-N-hydroxy-N-methyl-2-propynamide;

1-[5-[(4-methylsulfonyl)phenyl]-4-phenyl-2-oxazolyl]-N-hydroxy-N-methyl-2-propynamide;

1-[4-(4-chlorophenyl)-5-[(4-methylsulfonyl)phenyl)-2-oxazolyl]-N-hydroxy-N-methyl-2-propynamide;

2-methyl-3-[4-[(4-aminosulfonyl)phenyl]-N-hydroxy-N-methyl-5-phenyl-2-oxazolyl]-2-propynamide;

2-methyl-3-[4-[(4-aminosulfonyl)phenyl]-5-(4-chlorophenyl)-N-hydroxy-N-methyl-2-oxazolyl]-2-propynamide;

2-methyl-3-[5-[(4-aminosulfonyl)phenyl]-N-hydroxy-N-methyl-4-phenyl-2-oxazolyl]-2-propynamide;

2-methyl-3-[5-[(4-aminosulfonyl)phenyl]-4-(4-chlorophenyl)-N-hydroxy-N-methyl-2-oxazolyl]-2-propynamide;

2-methyl-3-(5-[(4-aminosulfonyl)phenyl]-4-(4-fluorophenyl)-N-hydroxy-N-methyl-2-oxazolyl]-2-propynamide;

2-methyl-3-[5-[(4-aminosulfonyl)phenyl]-4-(4-methoxyphenyl)-N-hydroxy-N-methyl-2-oxazolyl]-2-propynamide;

2-methyl-3-[5-[(4-aminosulfonyl)phenyl]-4-(3-chloro-4-methoxyphenyl)]-N-hydroxy-N-methyl-2-oxazolyl]-2-propynamide;

2-methyl-3-[5-[(4-aminosulfonyl)phenyl]-4-(3-fluoro-4-methoxyphenyl)-N-hydroxy-N-methyl-2-oxazolyl]-2-propynamide;

2-methyl-3-[5-[(4-aminosulfonyl)phenyl]-4-(3-chloro-4-fluorophenyl)-N-hydroxy-N-methyl-2-oxazolyl]-2-propynamide;

2-methyl-3-[N-hydroxy-N-methyl-4-[(4-methylsulfonyl)phenyl]-5-phenyl-2-oxazolyl]-2-propynamide;

2-methyl-3-[5-(4-chlorophenyl)-N-hydroxy-N-methyl-4-[(4-methylsulfonyl)phenyl]-2-oxazolyl]-2-propynamide;

2-methyl-3-[5-[(4-methylsulfonyl)phenyl]-N-hydroxy-N-methyl-4-phenyl-2-oxazolyl]-2-propynamide;

2-methyl-3-(4-(4-chlorophenyl)-5-[(4-methylsulfonyl)phenyl]-N-hydroxy-N-methyl-2-oxazolyl]-2-propynamide;

[4-[(4-aminosulfonyl)phenyl]-5-phenyl-2-oxazolyl]-N-hydroxy-N-methyl-2-benzamide;

[4-[(4-aminosulfonyl)phenyl]-5-(4-chlorophenyl)-2-oxazolyl]-N-hydroxy-N-methyl-2-benzamide;

[5-[(4-aminosulfonyl)phenyl]-4-phenyl-2-oxazolyl]-N-hydroxy-N-methyl-2-benzamide;

[5-[(4-aminosulfonyl)phenyl]-4-(4-chlorophenyl)-2-oxazolyl]-N-hydroxy-N-methyl-2-benzamide;

[5-[(4-aminosulfonyl)phenyl]-3-(4-fluorophenyl)-2-oxazolyl]-N-hydroxy-N-methyl-2-benzamide;

[5-[(4-aminosulfonyl)phenyl]-3-(4-methoxyphenyl)-2-oxazolyl]-N-hydroxy-N-methyl-2-benzamide;

[5-[(4-aminosulfonyl)phenyl]-3-(3-chloro-4-methoxyphenyl)-2-oxazolyl]-N-hydroxy-N-methyl-2-benzamide;

[5-[(4-aminosulfonyl)phenyl]-4-(3-fluoro-4-methoxyphenyl)-2-oxazolyl]-N-hydroxy-N-methyl-2-benzamide;

[5-[(4-aminosulfonyl)phenyl]-4-(3-chloro-4-fluorophenyl)-2-oxazolyl]-N-hydroxy-N-methyl-2-benzamide;

[4-[(4-methylsulfonyl)phenyl]-5-phenyl-2-oxazolyl]-N-hydroxy-N-methyl-2-benzamide;

[5-(4-chlorophenyl)-4-[(4-methylsulfonyl)phenyl]-2-oxazolyl]-N-hydroxy-N-methyl-2-benzamide;

[5-[(4-methylsulfonyl)phenyl]-4-phenyl-2-oxazolyl]-N-hydroxy-N-methyl-2-benzamide;

[4-(4-chlorophenyl)-5-[(4-methylsulfonyl)phenyl]-2-oxazolyl]-N-hydroxy-N-methyl-2-benzamide;

3-[4-[(4-aminosulfonyl)phenyl]-5-phenyl-2-oxazolyl]-N-hydroxy-N-methyl-3-cyclohexanamide;

3-[4-[(4-aminosulfonyl)phenyl]-5-(4-chlorophenyl)-2-oxazolyl]-N-hydroxy-N-methyl-3-cyclohexanamide;

3-[5-[(4-aminosulfonyl)phenyl]-4-phenyl-2-oxazolyl]-N-hydroxy-N-methyl-3-cyclohexanamide;

4-[5-(4-aminosulfonyl)phenyl]-4-(4-chlorophenyl)-2-oxazolyl]-N-hydroxy-N-methyl-3-cyclohexanamide;

4-[5-[(4-aminosulfonyl)phenyl]-4-(4-fluorophenyl)-2-oxazolyl]-N-hydroxy-N-methyl-3-cyclohexanamide;

4-[5-[(4-aminosulfonyl)phenyl]-4-(4-methoxyphenyl)-2-oxazolyl]-N-hydroxy-N-methyl-3-cyclohexanamide;

4-[5-[(4-aminosulfonyl)phenyl]-4-(3-chloro-4-methoxyphenyl)-2-oxazolyl]-N-hydroxy-N-methyl-3-cyclohexanamide;

4-[5-[(4-aminosulfonyl)phenyl]-4-(3-fluoro-4-methoxyphenyl)-2-oxazolyl]-N-hydroxy-N-methyl-3-cyclohexanamide;

4-[5-[(4-aminosulfonyl)phenyl]-4-(3-chloro-4-fluorophenyl)-2-oxazolyl]-N-hydroxy-N-methyl-3-cyclohexanamide;

4-[5-cyclohexyl-4-[(4-methylsulfonyl)phenyl]-2-oxazolyl]-N-hydroxy-N-methyl-3-cyclohexanamide;

4-[5-(4-chlorophenyl)-4-[(4-methylsulfonyl)phenyl]-2-oxazolyl]-N-hydroxy-N-methyl-3-cyclohexanamide;

3-(4-cyclohexenyl-5-[(4-methylsulfonyl)phenyl]-2-oxazolyl]-N-hydroxy-N-methyl-3-cyclohexanamide;

3-[4-(4-chlorophenyl)-5-[(4-methylsulfonyl)phenyl]-2-oxazolyl]-N-hydroxy-N-methyl-3-cyclohexanamide;

N'-[4-[4 (4-aminosulfonyl)phenyl]-5-phenyl-2-oxazolyl]methyl-N'-hydroxyurea;

N'-[4-[(4-aminosulfonyl)phenyl]-5-(4-chlorophenyl)-2-oxazolyl]methyl-N'-hydroxyurea;

N'-[5-[(4-aminosulfonyl)phenyl]-4-phenyl-2-oxazolyl]methyl-N'-hydroxyurea;

N'-[5-[(4-aminosulfonyl)phenyl]-4-(4-chlorophenyl)-2-oxazolyl]methyl-N'-hydroxyurea;

N'-[5-[(4-aminosulfonyl)phenyl]-4-(4-fluorophenyl)-2-oxazolyl]methyl-N'-hydroxyurea;

N'-[5-[(4-aminosulfonyl)phenyl]-4-(4-methoxyphenyl)-2-oxazolyl]methyl-N'-hydroxyurea;

N'-[5-[(4-aminosulfonyl)phenyl]-4-(3-chloro-4-methoxyphenyl)-2-oxazolyl]methyl-N'-hydroxyurea;

N'-[5-[(4-aminosulfonyl)phenyl]-4-(3-fluoro-4-methoxyphenyl)-2-oxazolyl]methyl-N'-hydroxyurea;

N'-[5-[(4-aminosulfonyl)phenyl]-4-(3-chloro-4-fluorophenyl)-2-oxazolyl]methyl-N'-hydroxyurea;

N'-[4-[(4-methylsulfonyl)phenyl]-5-phenyl-2-oxazolyl]methyl-N'-hydroxyurea;

N'-[5-(4-chlorophenyl)-4-[(4-methylsulfonyl)phenyl]-2-oxazolyl]methyl-N'-hydroxyurea;

N'-[5-[(4-methylsulfonyl)phenyl]-4-phenyl-2-oxazolyl]methyl-N'-hydroxyurea;

N'-[4-(4-chlorophenyl)-5-[(4-methylsulfonyl)phenyl]-2-oxazolyl]methyl-N'-hydroxyurea;

N'-[4-[(4-aminosulfonyl)phenyl]-5-phenyl-2-oxazolyl]ethyl-N'-hydroxyurea;

N'-[4-[(4-aminosulfonyl)phenyl]-5-(4-chlorophenyl)-2-oxazolyl]ethyl-N'-hydroxyurea;

N'-[5-[(4-aminosulfonyl)phenyl]-4-phenyl-2-oxazolyl]ethyl-N'-hydroxyurea;

N'-[5-[(4-aminosulfonyl)phenyl]-4-(4-chlorophenyl)-2-oxazolyl]ethyl-N'-hydroxyurea;

N'-[5-[(4-aminosulfonyl)phenyl]-4-(4-fluorophenyl)-2-oxazolyl]ethyl-N'-hydroxyurea;

N'-[5-[(4-aminosulfonyl)phenyl]-4-(4-methoxyphenyl)-2-oxazolyl]ethyl-N'-hydroxyurea;

N'-[5-[(4-aminosulfonyl)phenyl]-4-(3-chloro-4-methoxyphenyl)-2-oxazolyl]ethyl-N'-hydroxyurea;

N'-[5-[(4-aminosulfonyl)phenyl]-4-(3-fluoro-4-methoxyphenyl)-2-oxazolyl]ethyl-N'-hydroxyurea;

N'-[5-[(4-aminosulfonyl)phenyl]-4-(3-chloro-4-fluorophenyl)-2-oxazolyl]ethyl-N'-hydroxyurea;

N'-[4-[(4-methylsulfonyl)phenyl]-5-phenyl-2-oxazolyl]ethyl-N'-hydroxyurea;

N'-[5-(4-chlorophenyl)-4-[(4-methylsulfonyl)phenyl]-2-oxazolyl]ethyl-N'-hydroxyurea;

N'-[5-[(4-methylsulfonyl)phenyl]-4-phenyl-2-oxazolyl]ethyl-N'-hydroxyurea;

N'-[4-(4-chlorophenyl)-5-[(4-methylsulfonyl)phenyl]-2-oxazolyl]ethyl-N'-hydroxyurea;

3-[N'-[1-[4-[(4-aminosulfonyl)phenyl]-5-phenyl-2-oxazolyl]-2-propenyl]-N'-hydroxyurea;

3-[N'-[1-[4-[(4-aminosulfonyl)phenyl]-5-(4-chlorophenyl)-2-oxazolyl]-2-propynyl]-N'-hydroxyurea;

3-[N'-[1-[5-[(4-aminosulfonyl)phenyl]-4-phenyl-2-oxazolyl]-2-propynyl]-N'-hydroxyurea;

3-[N'-[1-[5-[(4-aminosulfonyl)phenyl]-4-(4-chlorophenyl)-2-oxazolyl]-2-propynyl]-N'-hydroxyurea;
3-[N'-[1-[5-[(4-aminosulfonyl)phenyl]-4-(4-fluorophenyl)-2-oxazolyl]-2-propynyl]-N'-hydroxyurea;
3-[N'-[1-[5-[(4-aminosulfonyl)phenyl]-4-(4-methoxyphenyl)-2-oxazolyl]-2-propynyl]-N'-hydroxyurea;
3-[N'-[1-[5-[(4-aminosulfonyl)phenyl]-4-(3-chloro-4-methoxyphenyl)-2-oxazolyl]-2-propynyl]-N'-hydroxyurea;
3-[N'-[1-[5-[(4-aminosulfonyl)phenyl]-4-(3-fluoro-4-methoxyphenyl)-2-oxazolyl]-2-propynyl]-N'-hydroxyurea;
3-[N'-[1-[5-[(4-aminosulfonyl)phenyl]-4-(3-chloro-4-fluorophenyl)-2-oxazolyl]-2-propynyl]-N'-hydroxyurea;
3-[N'-[1-[4-[(4-methylsulfonyl)phenyl]-5-phenyl-2-oxazolyl]-2-propynyl]-N'-hydroxyurea;
3-[N'-[1-[5-(4-chlorophenyl)-4-[(4-methylsulfonyl)phenyl]-2-oxazolyl]-2-propynyl]-N'-hydroxyurea;
3-[N'-[1-[5-[(4-methylsulfonyl)phenyl]-4-phenyl-2-oxazolyl]-2-propynyl]-N'-hydroxyurea;
3-[N'-[1-[4-(4-chlorophenyl)-5-[(4-methylsulfonyl)phenyl]-2-oxazolyl]-2-propynyl]-N'-hydroxyurea;
3-[N'-[4-[(4-aminosulfonyl)phenyl]-5-phenyl-2-oxazolyl]-2-propynyl]-N'-hydroxyurea;
3-[N'-[4-[(4-aminosulfonyl)phenyl]-5-(4-chlorophenyl)-2-oxazolyl]-2-propynyl]-N'-hydroxyurea;
3-[N'-[1-[5-(4-aminosulfonyl)phenyl]-4-phenyl-2-oxazolyl]-2-propynyl]-N'-hydroxyurea;
3-[N'-[1-[5-[(4-aminosulfonyl)phenyl]-4-(4-chlorophenyl)-2-oxazolyl]-2-propynyl]-N'-hydroxyurea;
3-[N'-[1-[5-[(4-aminosulfonyl)phenyl]-4-(4-fluorophenyl)-2-oxazolyl]-2-propynyl]-N'-hydroxyurea;
3-[N'-[1-[5-[(4-aminosulfonyl)phenyl]-4-(4-methoxyphenyl)-2-oxazolyl]-2-propynyl]-N'-hydroxyurea;
3-[N'-[1-[5-[(4-aminosulfonyl)phenyl]-4-(3-chloro-4-methoxyphenyl)-2-oxazolyl]-2-propynyl]-N'-hydroxyurea;
3-[N'-[1-[5-[(4-aminosulfonyl)phenyl]-4-(3-fluoro-4-methoxyphenyl)-2-oxazolyl]-2-propynyl]-N'-hydroxyurea;
3-[N'-[1-[5-[(4-aminosulfonyl)phenyl]-4-(3-chloro-4-fluorophenyl)-2-oxazolyl]-2-propynyl]-N'-hydroxyurea;
3-[N'-[1-[4-[(4-methylsulfonyl)phenyl]-5-phenyl-2-oxazolyl]-2-propynyl]-N'-hydroxyurea;
3-[N'-[1-[5-(4-chlorophenyl)-4-[(4-methylsulfonyl)phenyl]-2-oxazolyl]-2-propynyl]-N'-hydroxyurea;
3-[N'-[1-[5-[(4-methylsulfonyl)phenyl]-4-phenyl-2-oxazolyl]-2-propynyl]-N'-hydroxyurea;
3-[N'-[1-[4-(4-chlorophenyl)-5-[(4-methylsulfonyl)phenyl]-2-oxazolyl]-2-propynyl]-N'-hydroxyurea;
3-[N'-[1-[4-[(4-aminosulfonyl)phenyl]-5-phenyl-2-oxazolyl]-1-methyl-2-propynyl]-N'-hydroxyurea;
3-[N'-[1-[4-[(4-aminosulfonyl)phenyl]-5-(4-chlorophenyl)-2-oxazolyl]-1-methyl-2-propynyl]-N'-hydroxyurea;
3-[N'-[1-[5-[(4-aminosulfonyl)phenyl]-4-phenyl-2-oxazolyl]-1-methyl-2-propynyl]-N'-hydroxyurea;
3-[N'-[1-[5-[(4-aminosulfonyl)phenyl]-4-(4-chlorophenyl)-2-oxazolyl]-1-methyl-2-propenyl]-N'-hydroxyurea;
3-[N'-[1-[5-[(4-aminosulfonyl)phenyl]-4-(4-fluorophenyl)-2-oxazolyl]-1-methyl-2-propenyl]-N'-hydroxyurea;
3-[N'-[1-[5-[(4-aminosulfonyl)phenyl]-4-(4-methoxyphenyl)-2-oxazolyl]-1-methyl-2-propenyl]-N'-hydroxyurea;
3-[N'-[1-[5-[(4-aminosulfonyl)phenyl]-4-(3-chloro-4-methoxyphenyl)-2-oxazolyl]-1-methyl-2-propenyl]-N'-hydroxyurea;
3-[N'-[1-[5-[(4-aminosulfonyl)phenyl]-4-(3-fluoro-4-methoxyphenyl)-2-oxazolyl]-1-methyl-2-propenyl]-N'-hydroxyurea;
3-[N'-[1-[5-[(4-aminosulfonyl)phenyl]-4-(3-chloro-4-fluorophenyl)-2-oxazolyl]-1-methyl-2-propenyl]-N'-hydroxyurea;
3-[N'-[1-[4-[(4-methylsulfonyl)phenyl]-5-phenyl-2-oxazolyl]-1-methyl-2-propenyl]-N'-hydroxyurea;
3-[N'-[1-[5-(4-chlorophenyl)-4-[(4-methylsulfonyl)phenyl]-2-oxazolyl]-1-methyl-2-propenyl]-N'-hydroxyurea;
3-[N'-[1-[5-[(4-methylsulfonyl)phenyl]-4-phenyl-2-oxazolyl]-1-methyl-2-propenyl]-N'-hydroxyurea;
3-[N'-[1-[4-(4-chlorophenyl)-5-[(4-methylsulfonyl)phenyl]-2-oxazolyl]-1-methyl-2-propenyl]-N'-hydroxyurea;
N'-[3-[4-[(4-aminosulfonyl)phenyl]-5-phenyl-2-oxazolyl]phenyl]]-N'-hydroxyurea;
N'-[3-[4-[(4-aminosulfonyl)phenyl]-5-(4-chlorophenyl)-2-oxazolyl]phenyl]]-N'-hydroxyurea;
N'-[3-[5-[(4-aminosulfonyl)phenyl]-4-phenyl-2-oxazolyl]phenyl]]-N'-hydroxyurea;
N'-[3-[5-[(4-aminosulfonyl)phenyl]-4-(4-chlorophenyl)-2-oxazolyl]phenyl]]-N'-hydroxyurea;
N'-[3-[5-[(4-aminosulfonyl)phenyl]-4-(4-fluorophenyl)-2-oxazolyl]phenyl]]-N'-hydroxyurea;
N'-[3-[5-[(4-aminosulfonyl)phenyl]-4-(4-methoxyphenyl)-2-oxazolyl]phenyl]]-N'-hydroxyurea;
N'-[3-[5-[(4-aminosulfonyl)phenyl]-4-(3-chloro-4-methoxyphenyl)-2-oxazolyl]phenyl]]-N'-hydroxyurea;
N'-[3-[5-[(4-aminosulfonyl)phenyl]-4-(3-fluoro-4-methoxyphenyl)-2-oxazolyl]phenyl]]-N'-hydroxyurea;
N'-[3-[5-[(4-aminosulfonyl)phenyl]-4-(3-chloro-4-fluorophenyl)-2-oxazolyl]phenyl]]-N'-hydroxyurea;
N'-[3-[4-[(4-methylsulfonyl)phenyl]-5-phenyl-2-oxazolyl]phenyl]]-N'-hydroxyurea;
N'-[3-[5-(4-chlorophenyl)-4-[(4-methylsulfonyl)phenyl]-2-oxazolyl]phenyl]]-N'-hydroxyurea;
N'-[3-[5-[(4-methylsulfonyl)phenyl]-4-phenyl-2-oxazolyl]phenyl]]-N'-hydroxyurea;
N'-[3-[4-(4-chlorophenyl)-5-[(4-methylsulfonyl)phenyl]-2-oxazolyl]phenyl]]-N'-hydroxyurea;
N'-[3-[4-[(4-aminosulfonyl)phenyl]-5-phenyl-2-oxazolyl]cyclohexyl]-N'-hydroxyurea;
N'-[3-[4-[(4-aminosulfonyl)phenyl]-5-(4-chlorophenyl)-2-oxazolyl]cyclohexyl]-N'-hydroxyurea;
N'-[3-[5-[(4-aminosulfonyl)phenyl]-4-phenyl-2-oxazolyl]cyclohexyl]-N'-hydroxyurea;

N'-[3-[5-[(4-aminosulfonyl)phenyl]-4-(4-chlorophenyl)-2-oxazolyl]cyclohexyl]-N'-hydroxyurea;

N'-[3-[5-[(4-aminosulfonyl)phenyl]-4-(4-fluorophenyl)-2-oxazolyl]cyclohexyl]-N'-hydroxyurea;

N'-[3-[5-[(4-aminosulfonyl)phenyl]-4-(4-methoxyphenyl)-2-oxazolyl]cyclohexyl]-N'-hydroxyurea;

N'-[3-[5-[(4-aminosulfonyl)phenyl]-4-(3-chloro-4-methoxyphenyl)-2-oxazolyl]cyclohexyl]-N'-hydroxyurea;

N'-[3-[5-[(4-aminosulfonyl)phenyl]-4-(3-fluoro-4-methoxyphenyl)-2-oxazolyl]cyclohexyl]-N'-hydroxyurea;

N'-[3-[5-[(4-aminosulfonyl)phenyl]-4-(3-chloro-4-fluorophenyl)-2-oxazolyl]cyclohexyl]-N'-hydroxyurea;

N'-[3-[4-[(4-methylsulfonyl)phenyl]-5-phenyl-2-oxazolyl]cyclohexyl]-N'-hydroxyurea;

N'-[3-[5-(4-chlorophenyl)-4-[(4-methylsulfonyl)phenyl]-2-oxazolyl]cyclohexyl]-N'-hydroxyurea;

N'-[3-[5-[(4-methylsulfonyl)phenyl]-4-phenyl-2-oxazolyl]cyclohexyl]-N'-hydroxyurea;

N'-[3-[4-(4-chlorophenyl)-5-[(4-methylsulfonyl)phenyl]-2-oxazolyl]cyclohexyl]-N'-hydroxyurea; and 4-(4-fluorophenyl)-N-hydroxy-N-methyl-5-[(4-methylsulfonyl)phenyl]-2-oxazolepropanamide.

5. A pharmaceutical composition comprising a therapeutically-efffective amount of a compound of claim 1, or a pharmaceutically-acceptable salt thereof, and at least one pharmaceutically-acceptable carrier, adjuvant or diluent.

\* \* \* \* \*

UNITED STATES PATENT AND TRADEMARK OFFICE
CERTIFICATE OF CORRECTION

PATENT NO.      : 6,875,785 B2
APPLICATION NO. : 10/254701
DATED           : April 5, 2005
INVENTOR(S)     : John J. Talley et al.

It is certified that error appears in the above-identified patent and that said Letters Patent is hereby corrected as shown below:

Column 79, claim 1
    Line 13, "alkoxycarbonyl, and cycloalkyl;" should read -- alkoxycarbonyl, carboxalkyl, cyanoalkyl and hydroxyalkyl; --.
    Line 18, "cycloalkyl, cycloalkylalkyl, and heterocycloalkyl;" should read --cycloalkyl, and cycloalkylalkyl; --.
    Line 20, delete "heterocyclo,".

Column 81, claim 4
    Lines 1 and 18, that portion reading "[5-(4-" should read -- [5-[(4- --.

Column 84, claim 4
    Line 17, that portion reading "phenyl-2-" should read -- phenyl]-2- --.
    Lines 31 and 38, that portion reading "hydroxy-N-methyl-2-" should read -- hydroxy-2- --.

Column 85, claim 4
    Line 66, that portion reading "1-[4-(4-" should read -- 1-[4-[(4- --

Column 86, claim 4
    Line 16, that portion reading "phenyl)-4-" should read -- phenyl]-4- --.
    Line 37, that portion reading "phenyl)-2-" should read -- phenyl]-2- --.

Column 87, claim 4
    Line 6, that portion reading "-3-(4-(4-" should read -- -3-[4-(4- --.

Column 88, claim 4
    Line 1, that portion reading "3-(4- " should read -- 3-[4- --.
    Line 5, that portion reading "N'-[4-[4" should read -- N'-[4[(4- --.
    Lines 64, 67, that portion reading "2-propynyl]" should read -- 2-propenyl] --.

Column 89, claim 4
    Lines 2, 5, 8, 11, 15, 18, 21, 23, 25 and 27, that portion reading "2-propynyl]" should read -- 2-propenyl] --.
    Lines 29 and 31, that portion reading "3-[N'-[4-[(4-" should read -- 3-[N'-[1 -[4-[(4- --.
    Line 33, that portion reading "3-[N'-[1-[5-(4-" should read -- 3-[N'-[1-[5-[(4- --.

UNITED STATES PATENT AND TRADEMARK OFFICE
CERTIFICATE OF CORRECTION

PATENT NO. : 6,875,785 B2
APPLICATION NO. : 10/254701
DATED : April 5, 2005
INVENTOR(S) : John J. Talley et al.

It is certified that error appears in the above-identified patent and that said Letters Patent is hereby corrected as shown below:

<u>Column 90, claim 4</u>
      Lines 4, 7, 11, 13, 17, 20, 23, 26, 29, 31, that portion reading "2-propenyl]" should read -- 2-propynyl] --.
      Line 43, that portion reading "2-oxazolyl)phenyl]]" should read -- 2-oxazolyl]phenyl]] --.

Signed and Sealed this

Fifth Day of December, 2006

JON W. DUDAS
*Director of the United States Patent and Trademark Office*